United States Patent
Shusta et al.

(10) Patent No.: US 12,371,468 B2
(45) Date of Patent: Jul. 29, 2025

(54) VARIABLE LYMPHOCYTE RECEPTORS THAT TARGET THE BLOOD BRAIN BARRIER AND METHODS OF USE

(71) Applicants: WISCONSIN ALUMNI RESEARCH FOUNDATION, Madison, WI (US); EMORY UNIVERSITY, Atlanta, GA (US)

(72) Inventors: Eric V. Shusta, Madison, WI (US); Jason M. Lajoie, Madison, WI (US); Brantley R. Herrin, Madison, WI (US)

(73) Assignees: WISCONSIN ALUMNI RESEARCH FOUNDATION, Madison, WI (US); EMORY UNIVERSITY, Atlanta, GA (US)

( * ) Notice: Subject to any disclaimer, the term of this patent is extended or adjusted under 35 U.S.C. 154(b) by 992 days.

(21) Appl. No.: 17/429,602

(22) PCT Filed: Feb. 11, 2020

(86) PCT No.: PCT/US2020/017624
§ 371 (c)(1),
(2) Date: Aug. 9, 2021

(87) PCT Pub. No.: WO2020/167735
PCT Pub. Date: Aug. 20, 2020

(65) Prior Publication Data
US 2022/0204583 A1 Jun. 30, 2022

Related U.S. Application Data

(60) Provisional application No. 62/804,003, filed on Feb. 11, 2019.

(51) Int. Cl.
C07K 14/725 (2006.01)
A61K 39/00 (2006.01)
A61K 47/68 (2017.01)
C07K 16/28 (2006.01)

(52) U.S. Cl.
CPC .......... *C07K 14/7051* (2013.01); *A61K 47/68* (2017.08); *C07K 16/2881* (2013.01); *A61K 2039/505* (2013.01); *C07K 2317/565* (2013.01); *C07K 2317/569* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | |
|---|---|---|
| 8,039,588 B2 | 10/2011 | Pancer et al. |
| 8,212,018 B2 | 7/2012 | Pancer et al. |
| 9,127,087 B2 | 9/2015 | Pancer et al. |
| 10,036,747 B2 | 7/2018 | Pancer et al. |
| 2017/0081385 A1 | 3/2017 | Herrin et al. |

FOREIGN PATENT DOCUMENTS

| | | | |
|---|---|---|---|
| WO | 2006083275 A2 | 8/2006 | |
| WO | WO2006/083275 | * 8/2006 | ........... C07K 14/705 |
| WO | 2013078425 A1 | 5/2013 | |
| WO | 2015168469 A1 | 11/2015 | |
| WO | 2015174869 A1 | 11/2015 | |
| WO | 2020132301 A1 | 6/2020 | |

OTHER PUBLICATIONS

Bhattacharya et al., PLoS One 12(3): e0171355. https://doi.org/10.1371/journal.pone.0171355; 22 pages total (Year: 2017).*
Fenton et al., Medicinal Chemistry Research (2020) 29:1133-1146 (Year: 2020).*
Alder et al., Science (2005) 310, 1970-1973 (Year: 2005).*
Abbott, N. J., A. A. K. Patabendige, D. E. M. Dolman, S. R. Yusof, D. J. Begley, Structure and function of the blood-brain barrier. Neurobiol. Dis. 37, 13-25 (2010).
Brown, B. Badie, M. E. Barish, L. Weng, J. R. Ostberg, W.-C. Chang, A. Naranjo, R. Starr, J. Wagner, C. Wright, Y. Zhai, J. R. Bading, J. A. Ressler, J. Portnow, M. D'Apuzzo, S. J. Forman, M. C. Jensen, Bioactivity and safety of IL13Rα2-redirected chimeric antigen receptor CD8+ T cells in patients with recurrent glioblastoma. Clin. Cancer Res. 21, 4062-4072 (2015).
Brown, Peptidic tumor targeting agents: The road from phage display peptide selections to clinical applications. Curr. Pharm. Des. 16, 1040-1054 (2010).
Burns, T. M. Malott, K. J. Metcalf, B. J. Hackel, J. R. Chan, E. V. Shusta, Directed evolution of brain-derived neurotrophic factor for improved folding and expression in *Saccharomyces cerevisiae*. Appl. Environ. Microbiol. 80, 5732-5742 (2014).
Calabria, A. R. & Shusta, E. V. A genomic comparison of in vivo and in vitro brain microvascular endothelial cells. J. Cereb. Blood Flow Metab. 28, 135-48 (2008).
Castaldo, C. et al. Cardiac fibroblast-derived extracellular matrix (biomatrix) as a model for the studies of cardiac primitive cell biological properties in normal and pathological adult human heart. Biomed Res. Int. (2013).
Chao, G. et al. Isolating and engineering human antibodies using yeast surface display. Nat. Protoc. 1, 755-768 (2006).
Chia, P. Z. C., Gunn, P. & Gleeson, P. A. Cargo trafficking between endosomes and the trans-Golgi network. Histochem. Cell Biol. 140, 307-15 (2013).
Clark et al. "Neurovascular-targeting antibodies discovered using yeast biopanning enhance drug delivery and improve survival for glioblastoma," Cancer Res (2018) 78 (13_Supplement): 1764. (Abstract).
Collins, B. C. et al. Structural Insights into VLR Fine Specificity for Blood Group Carbohydrates. Structure 25, 1-12 (2017).

(Continued)

*Primary Examiner* — Christina M Borgeest
(74) *Attorney, Agent, or Firm* — Quarles & Brady, LLP

(57) ABSTRACT

The present disclosure provides isolated polypeptides comprising variable lymphocyte receptors that specifically bind the blood brain barrier, compositions, and methods of use.

22 Claims, 12 Drawing Sheets
(11 of 12 Drawing Sheet(s) Filed in Color)
Specification includes a Sequence Listing.

(56) References Cited

OTHER PUBLICATIONS

Crapo, T. W. Gilbert, S. F. Badylak, An overview of tissue and whole organ decellularization processes. Biomaterials 32, 3233-3243 (2011).
Daneman, R. The blood-brain barrier in health and disease. Ann. Neurol. 72, 648-72 (2012).
Gadkar, K. et al. Mathematical PKPD and safety model of bispecific TfR/BACE1 antibodies for the optimization of antibody uptake in brain. Eur. J. Pharm. Biopharm. 101, 53-61 (2016).
Gray, M. J. McGuire, K. C. Brown, A liposomal drug platform overrides peptide ligand targeting to a cancer biomarker, irrespective of ligand affinity or density. PLOS One 8, e72938 (2013).
Gunn, R. J., Herrin, B. R., Acharya, S., Cooper, M. D. & Wilson, I. A. VLR Recognition of TLR5 Expands the Molecular Characterization of Protein Antigen Binding by Non-Ig based Antibodies. J. Mol. Biol. 430, 1350-1367 (2018).
Gupta, V. P. Torchilin, Monoclonal antibody 2C5-modified doxorubicin-loaded liposomes with significantly enhanced therapeutic activity against intracranial human brain U-87 MG tumor xenografts in nude mice. Cancer Immunol. Immunother. 56, 1215-1223 (2007).
Herrin et al., "Structure and specificity of lamprey monoclonal antibodies," Proc Natl Acad Sci U S A Feb. 12, 2008;105(6):2040-5.
Herrin, M. D. Cooper, Alternative adaptive immunity in jawless vertebrates. J. Immunol. 185, 1367-1374 (2010).
Holodinsky, A. Y. X. Yu, Z. A. Assis, A. S. Al Sultan, B. K. Menon, A. M. Demchuk, M. Goyal, M. D. Hill, History, evolution, and importance of emergency endovascular treatment of acute ischemic stroke. Curr. Neurol. Neurosci. Rep. 16, 42 (2016).
Hong, M. Z. Ma, J. C. Gildersleeve, S. Chowdhury, J.J. BarchiJr., R. A. Mariuzza, M. B. Murphy, L. Mao, Z. Pancer, Sugar-binding proteins from fish: Selection of high affinity "lambodies" that recognize biomedically relevant glycans. ACS Chem. Biol. 8, 152-160 (2013).
Hwang, J.-H. Ryou, J. R. Oh, J. W. Han, T. K. Park, H.-S. Kim, Anti-human VEGF repebody effectively suppresses choroidal neovascularization and vascular leakage. PLOS One 11, e0152522 (2016).
Iacopetta, B. J. & Morgan, E. H. The kinetics of transferrin endocytosis and iron uptake from transferrin in rabbit reticulocytes. J. Biol. Chem. 258, 9108-15 (1983).
Kasahara et al., "Two Forms of Adaptive Immunity in Vertebrates: Similarities and Differences." Adv in Immunol. (2014).
Kumar, P. et al. Macromolecularly crowded in vitro microenvironments accelerate the production of extracellular matrix-rich supramolecular assemblies. Sci. Rep. 5, 8729 (2015).
Kuznetsov, R. K. Puri, Kinetic analysis of high affinity forms of interleukin (IL)-13 receptors: Suppression of IL-13 binding by IL-2 receptor gamma chain. Biophys. J. 77, 154-172 (1999).
Lajoie, J. M. & Shusta, E. V. Targeting receptor-mediated transport for delivery of biologics across the blood-brain barrier. Annu. Rev. Pharmacol. Toxicol. 55, 613-31 (2015).
Lamsam, E. Johnson, I. D. Connolly, M. Wintermark, M. Hayden Gephart, A review of potential applications of MR-guided focused ultrasound for targeting brain tumor therapy. Neurosurg. Focus 44, E10 (2018).
Lee, H. J. Kim, C.-S. Yang, H.-H. Kyeong, J.-M. Choi, D.-E. Hwang, J.-M. Yuk, K. Park, Y. J. Kim, S.-G. Lee, D. Kim, E.-K. Jo, H.-K. Cheong, H.-S. Kim, A high-affinity protein binder that blocks the IL-6/STAT3 signaling pathway effectively suppresses non-small cell lung cancer. Mol. Ther. 22, 1254-1265 (2014).
Lidinsky, W. A. & Drewes, L. R. Characterization of the Blood-Brain Barrier: Protein Composition of the Capillary Endothelial Cell Membrane. J. Neurochem. 41, 1341-1348 (1983).
Lockman, R. K. Mittapalli, K. S. Taskar, V. Rudraraju, B. Gril, K. A. Bohn, C. E. Adkins, A. Roberts, H. R. Thorsheim, J. A. Gaasch, S. Huang, D. Palmieri, P. S. Steeg, Q. R. Smith, Heterogeneous blood—tumor barrier permeability determines drug efficacy in experimental brain metastases of breast cancer. Clin. Cancer Res. 16, 5664-5678 (2010).
Mann, P. Scodeller, S. Hussain, J. Joo, E. Kwon, G. B. Braun, T. Mölder, Z.-G. She, V. R. Kotamraju, B. Ranscht, S. Krajewski, T. Teesalu, S. Bhatia, M. J. Sailor, E. Ruoslahti, A peptide for targeted, systemic delivery of imaging and therapeutic compounds into acute brain injuries. Nat. Commun. 7, 11980 (2016).
McCaffrey,G., T. P. Davis, Physiology and pathophysiology of the blood-brain barrier: P-glycoprotein and occludin trafficking as therapeutic targets to optimize central nervous system drug delivery. J. Invest. Med. 60, 1131-1140 (2012).
Michel, C. C. Transport of macromolecules through microvascular walls. Cardiovasc. Res. 32, 644-53 (1996).
Minagar, J. S. Alexander, Blood-brain barrier disruption in multiple sclerosis. Mult. Scler. 9, 540-549 (2003).
Moos, T. & Morgan, E. H. Restricted transport of anti-transferrin receptor antibody (OX26) through the blood-brain barrier in the rat. J. Neurochem. 79, 119-29 (2001).
Murugandam, A., Tanha, J., Narang, S. & Stanimirovic, D. Selection of phage displayed llama single-domain antibodies that trans-migrate across human blood-brain barrier endothelium. FASEB J. 16 (2002).
Nance, K. Timbie, G. W. Miller, J. Song, C. Louttit, A. L. Klibanov, T.-Y. Shih, G. Swaminathan, R. J. Tamargo, G. F. Woodworth, J. Hanes, R. J. Price, Non-invasive delivery of stealth, brain-penetrating nanoparticles across the blood-brain barrier using MRI-guided focused ultrasound. J. Control. Release 189, 123-132 (2014).
Nico, D. Ribatti, Morphofunctional aspects of the blood-brain barrier. Curr. Drug Metab. 13, 50-60 (2012).
Niewoehner, J. et al. Increased Brain Penetration and Potency of a Therapeutic Antibody Using a Monovalent Molecular Shuttle. Neuron 81, 49-60 (2014).
Nitta et al., Size-selective loosening of the blood-brain barrier in claudin-5-deficient mice. J Cell Biol 161(3):653-60 (2003).
Obermeier, A. Verma, R. M. Ransohoff, The blood-brain barrier. Handb. Clin. Neurol. 133, 39-59 (2016).
Oh, S. Fakurnejad, E. T. Sayegh, A. J. Clark, M. E. Ivan, M. Z. Sun, M. Safaee, O. Bloch, C. D. James, A. T. Parsa, Immunocompetent murine models for the study of glioblastoma immunotherapy. J. Transl. Med. 12, 107 (2014).
Ostrom, H.Gittleman, J. Fulop, M. Liu, R. Blanda, C. Kromer, Y. Wolinsky, C. Kruchko, J. S. Barnholtz-Sloan, CBTRUS statistical report: Primary brain and central nervous system tumors diagnosed in the united states in 2008-2012. Neuro Oncol. 17 Suppl 4, iv1-iv62 (2015).
Pardridge, W. M. The blood-brain barrier: bottleneck in brain drug development. NeuroRx 2, 3-14 (2005).
Pasqualini, R. & Ruoslahti, E. Organ targeting in vivo using phage display peptide libraries. Nature 380, 364-6 (1996).
Pellegatta, B. Savoldo, N. Di Ianni, C. Corbetta, Y. Chen, M. Patané, C. Sun, B. Pollo, S. Ferrone, F. DiMeco, G. Finocchiaro, G. Dotti, Constitutive and TNF☐-inducible expression of chondroitin sulfate proteoglycan 4 in glioblastoma and neurospheres: Implications for CAR-T cell therapy. Sci. Transl. Med. 10, eaao2731 (2018).
Piatesi, A. et al. Directed evolution for improved secretion of cancer-testis antigen NY ESO-1 from yeast. Protein Expr. Purif. 48, 232-242 (2006).
Ponsel, D., Neugebauer, J., Ladetzki-Baehs, K. & Tissot, K. High affinity, developability and functional size: the holy grail of combinatorial antibody library generation. Molecules 16, 3675-700 (2011).
Preusser, M. Lim, D. A. Hafler, D. A. Reardon, J. H. Sampson, Prospects of immune checkpoint modulators in the treatment of glioblastoma. Nat. Rev. Neurol. 11, 504-514 (2015).
Requirement for Restriction for U.S. Appl. No. 17/414,581, mailed Apr. 20, 2023.
Saito G, Swanson J A, Lee K D. Drug delivery strategy utilizing conjugation via reversible disulfide linkages: role and site of cellular reducing activities, Adv Drug Deliv Rev. Feb. 10, 2003; 55(2):199-215.
Sata, T et al., "Dectection of the Neu5Ac (a2,3) Gal (b1,4) GlcNAc Sequence within the Leukoagglutinin from Maackia amurensis: Light and Electron Microscopic Demonstration of Differential Tissue Expression of t Terminal Sialic Acid in a2,3- and a2,6 linkage." The Journal of Histochemistry and Cytochemistry, Nov. 1989, vol. 37, No. 11, pp. 1577-1588.

(56) References Cited

OTHER PUBLICATIONS

Scott, D. W. & Patel, R. P. Endothelial heterogeneity and adhesion molecules N-glycosylation: implications in leukocyte trafficking in inflammation. Glycobiology 23, 622-33 (2013).
Shi et al., "Rapid endothelial cytoskeletal reorganization enables early blood-brain barrier disruption and long-term ischaemic reperfusion brain injury," Nat Commun . Jan. 27, 2016;7:10523.
Shusta, E, "Using Lamprey Antibodies to Profile the Blood-Brain Barrier", National Institute of Health (2015).
Siegel, K. D. Miller, A. Jemal, Cancer statistics, 2015. CA Cancer J. Clin. 65, 5-29 (2015).
Silber, P. M., Gandolfi, A. J. & Brendel, K. Adaptation of a gamma-glutamyl-transferase transpeptidase assay to microtiter plates. Anal. Biochem. 158, 68-71 (1986).
Steiner, P. Forrer, A. Plückthun, Efficient selection of DARPins with sub-nanomolar affinities using SRP phage display. J. Mol. Biol. 382, 1211-1227 (2008).
Stern, L. A. et al. Geometry and expression enhance enrichment of functional yeast displayed ligands via cell panning. Biotechnol. Bioeng. (2016). doi:10.1002/bit.26001.
Stutz, C. C., et al. Identifying blood-brain-barrier selective single-chain antibody fragments. Biotechnol J. 9, 664-74 (2014).
Stutz, C. C., Zhang, X. & Shusta, E. V. Combinatorial approaches for the identification of brain drug delivery targets. Curr. Pharm. Des. 20, 1564-76 (2014).
Sugano et al., Antibody Targeting of Doxorubicin-loaded Liposomes Suppresses the Growth and Metastatic Spread of Established Human Lung Tumor Xenografts in Severe Combined Immunodeficient Mice Cancer Research 60, 6942-6949, Dec. 15, 2000.
Sukhanova et al., "Oriented conjugates of single-domain antibodies and quantum dots: toward a new generation of ultrasmall diagnostic nanoprobes," Nanomedicine 8(4): 516-525, 2012.
Swanson, P. A. Clark, R. R. Zhang, I. K. Kandela, M. Farhoud, J. P. Weichert, J. S. Kuo, Fluorescent cancer-selective alkylphosphocholine analogs for intraoperative glioma detection. Neurosurgery 76, 115-124 (2015).
Tillotson, B. J., Cho, Y. K. & Shusta, E. V. Cells and cell lysates: A direct approach for engineering antibodies against membrane proteins using yeast surface display. Methods 60, 27-37 (2013).
Tillotson, B. J., de Larrinoa, I. F., Skinner, C. A., Klavas, D. M. & Shusta, E. V. Antibody affinity maturation using yeast display with detergent-solubilized membrane proteins as antigen sources. Protein Eng. Des. Sel. 26, 101-112 (2013).
Trail P A, King H D, Dubowchik G M, Monoclonal antibody drug immunoconjugates for targeted treatment of cancer, Cancer Immunol Immunother. May 2003; 52(5):328-37.
Ueno, M. et al. Transporters in the brain endothelial barrier. Curr. Med. Chem. 17, 1125-38 (2010).

Umlauf, "Identification and Development of Variable Lymphocyte Targeting Ligands for Glioblastoma," PEGS Boston, 2018 (Presentation).
Umlauf, BJ et al., "Identification of variable lymphocyte receptors that can target therapeutics to pathologically exposed brain extracellular matrix." Science Advances, May 15, 2019, vol. 5, No. eaau4245, pp. 1-12.
Umlauf, K. A. Mix, V. A.Grosskopf, R. T. Raines, E. V. Shusta, Site-specific antibody functionalization using tetrazine-styrene cycloaddition. Bioconjug. Chem. 29, 1605-1613 (2018).
Van De Broek et al., "Specific cell targeting with nanobody conjugated branched gold nanoparticles for photothermal therapy," ACS Nano 5(6): 4319-4328, 2011.
Van Den Berg, B. M., Vink, H. & Spaan, J. A. E. The endothelial glycocalyx protects against myocardial edema. Circ. Res. 92, 592-4 (2003).
Venkataraman, M., Sasisekharan, R. & Raman, R. Glycan Array Data Management at Consortium for Functional Glycomics. in Methods in molecular biology (Clifton, N.J.) 1273, 181-190 (2015).
Vogel, J. et al. Influence of the endothelial glycocalyx on cerebral blood flow in mice. J. Cereb. Blood Flow Metab. 20, 1571-8 (2000).
Wang, E. V. Shusta, The use of scFv-displaying yeast in mammalian cell surface selections. J. Immunol. Methods 304, 30-42 (2005).
Wang, X. X., Cho, Y. K. & Shusta, E. V. Mining a yeast library for brain endothelial cell binding antibodies. Nat. Methods 4, 143-145 (2007).
Waters and Shusta. "The variable lymphocyte receptor as an antibody alternative." Curr Opin Biotechnol. Aug. 2018; 52:74-79.
Whitehead et. al. "Artificial Membrane Fusion Triggered by Strain-Promoted Alkyne-Azide Cycloaddition" Bioconjugate Chem. Apr. 28, 2017, 923-932 DOI: 10.1021/acs.bioconjchem.6b00578.
Williams, R. L. et al. Endothelioma cells expressing the polyoma middle T oncogene induce hemangiomas by host cell recruitment. Cell 57, 1053-63 (1989).
Woodworth, G. P. Dunn, E. A. Nance, J. Hanes, H. Brem, Emerging insights into barriers to effective brain tumor therapeutics. Front. Oncol. 4, 126 (2014).
Wu A M, Senter P D, Arming antibodies: prospects and challenges for immunoconjugates, Nat Biotechnol. Sep. 2005; 23(9):1137-46.
Yu, C. et al. Identification of human plasma cells with a lamprey monoclonal antibody. JCI Insight 1 (2016).
Yu, Y. J. et al. Boosting brain uptake of a therapeutic antibody by reducing its affinity for a transcytosis target. Sci. Transl. Med. 3 (2011).
Yu, Y. J. et al. Therapeutic bispecific antibodies cross the blood-brain barrier in nonhuman primates. Sci. Transl. Med. 6 (2014).
Zhou, H., Zhang, Y.-L., Lu, G., Ji, H. & Rodi, C. P. Recombinant antibody libraries and selection technologies. N. Biotechnol. 28, 448-52 (2011).

\* cited by examiner

Table 2: Glycan binding measurements and glycan descriptions for the top 10 glycans recognized by VLR-Fcs-11, -30, and -46 in the CFG glycan microarray analysis

VARIABLE LYMPHOCYTE RECEPTORS THAT TARGET THE BLOOD BRAIN BARRIER AND METHODS OF USE

CROSS-REFERENCE TO RELATED APPLICATIONS

This application is a national stage filing under 35 U.S.C. § 371 of International Application No. PCT/US2020/017624, filed on Feb. 11, 2020, which claims priority to U.S. Provisional Application No. 62/804,003, filed on Feb. 11, 2019, the contents of which is incorporated by reference in its entirety.

STATEMENT REGARDING FEDERALLY SPONSORED RESEARCH

This invention was made with government support under NS091851 and NS099158 awarded by the National Institutes of Health. The government has certain rights in the invention.

SEQUENCE LISTING

A Sequence Listing accompanies this application and is submitted as an ASCII text file of the sequence listing named "2020-01-30_960296.03994_ST25" which is 19.0 kb in size and was created on Jan. 30, 2020. The sequence listing is electronically submitted via EFS-Web with the application and is incorporated herein by reference in its entirety.

BACKGROUND OF THE INVENTION

The field of the invention is related to polypeptides and antibodies specific to the blood brain barrier. More particularly, the invention relates to variable lymphocyte receptors that can bind the blood brain barrier in vivo, and polypeptides and compositions comprising them.

The brain vasculature, also known as the blood-brain barrier (BBB), is substantially more impermeable to blood-borne constituents than the peripheral vasculature. Continuous paracellular tight junctions between brain endothelial cells (BECs) combine with a low level of pinocytosis to restrict the nonspecific brain uptake of molecules, proteins and cells, while a host of drug efflux transporters serve to actively pump molecules that do enter the BECs back into the bloodstream[1]. While these barrier functions are essential in health, they present a significant challenge when attempting to treat neurological disorders because the majority of small molecule therapeutics, and essentially all gene and protein-based drugs do not appreciably cross the BBB[2]. Therefore, effective non-invasive drug delivery strategies that can overcome this barrier are critical for the successful development of central nervous system (CNS) therapeutics.

As a result of the prominent barrier function, the BBB endothelia express numerous transport systems to facilitate brain uptake of key nutrients such as glucose and amino acids as well as proteins such as transferrin and insulin[3]. Importantly, it is possible to coopt certain endogenous receptor-mediated transport systems, such as the transferrin receptor (TfR), and insulin receptor (IR), for the delivery of drug payloads across the BBB using receptor-targeting antibodies or ligand mimics[4]. Although pharmacologic amounts of drug can be successfully delivered to the brain by targeting these receptors, several factors combine to limit their efficiency. Ubiquitous expression of TfR and IR throughout the body results in mistargeting to peripheral organs, limiting brain uptake and increasing the potential of off-target effects[5,6]. Furthermore, affinity- and avidity-based interactions can result in lysosomal degradation of antibodies within the BECs, further limiting access to the brain[7,8]. While efforts to engineer the binding properties of TfR targeting antibodies have shown some success[9-12], typically less than 1% of the injected dose of therapeutic antibody reaches the brain parenchyma requiring high concentration dosing (up to 50 mg/kg). Thus, there remains a significant need for discovery and development of novel BBB receptor-targeting antibodies.

Genomic and proteomic profiling of BECs is one approach that has been implemented to identify new BBB transport systems. For example, this approach was recently used to identify highly expressed proteins, basigin and CD98 heavy chain, as potential drug carriers[13]. However, it is often difficult to determine what BBB receptors are actually capable of transport simply from sequence data, as non-canonical transporters have been identified[13-15]. An alternative approach involves phenotypic screening of large combinatorial antibody or peptide repertoires both in vitro and in vivo to identify BBB targeting molecules[16]. However, despite considerable screening efforts, few new targeting reagents have been generated[16]. For example, there has been limited success using in vivo screening approaches, such as the systemic injection of phage libraries[17], likely due to high phage background binding and significant phage uptake by peripheral organs.

Furthermore, promising clones identified from in vitro screening platforms, such as phage and yeast display biopanning on cultured cells, often do not cross-react with in vivo antigens' as a result of altered expression profiles of BECs in the petri dish[19,20]. To date, the antibody repertoires employed have been limited to naïve mammalian antibody fragments[21,22], while application of immunization-based approaches in the BBB field have been confined to proteomic profiling efforts[23,24]. Therefore, the search for new BBB targets would benefit from the development and application of innovative screening platforms with the ability to more broadly and efficiently sample the in vivo-relevant BBB antigen landscape.

SUMMARY OF THE INVENTION

The present invention overcomes the aforementioned drawbacks by providing polypeptides, nucleic acids encoding the polypeptides, and compositions comprising the polypeptides, wherein the polypeptides comprises variable lymphocyte receptors specific for in vivo binding to the blood brain barrier.

In one aspect, the present disclosure provides an isolated polypeptide or antigen-binding fragment thereof able to specifically bind to the blood brain barrier in vivo comprising an amino acid sequence of a variable lymphocyte receptor (VLR) comprising two or more of the following regions:
  (i) EVRCESRSLASVPA (SEQ ID NO:5) or an amino acid sequence having at least 90% identity to SEQ ID NO:5, TVDCSGKSLASVPT (SEQ ID NO:13) or an amino acid sequence having at least 90% identity to SEQ ID NO:13, or TVDCSGKSLASVPT (SEQ ID NO:16) or an amino acid sequence having at least 90% identity to SEQ ID NO:16;
  (ii) RRLHLHR (SEQ ID NO:6) or an amino acid sequence having at least 90% identity to SEQ ID NO:6, QILRLYRNQI (SEQ ID NO: 14) or an amino acid sequence having at least 90% identity to SEQ ID NO:14, or RWLHLHR (SEQ ID NO: 17) or an amino acid sequence having at least 90% identity to SEQ ID NO:17,
(iii) YLNLGG (SEQ ID NO:7) or an amino acid sequence having at least 90% identity to SEQ ID NO:7,
(iv) ELKLYS (SEQ ID NO:8) or an amino acid sequence having at least 90% identity to SEQ ID NO:8,
(v) HLDLSK (SEQ ID NO:9) or an amino acid sequence having at least 90% identity to SEQ ID NO:9,
(vi) HAYLFG (SEQ ID NO:10) or an amino acid sequence having at least 90% identity to SEQ ID NO:10, and
(vii) SIVMRWDGKAVNDPDSAK (SEQ ID NO:11) or an amino acid sequence having at least 90% identity to SEQ ID NO:11, wherein the isolated peptide or antigen-binding fragment thereof is able to specifically bind to the blood brain barrier in vivo. In some embodiments, the In some aspects, isolated peptide or antigen-binding fragment thereof comprises two or more of i-vii regions, alternatively three or more of i-vii regions, alternatively four or more of i-vii regions, alternatively five or more of i-vii regions, alternatively six or more of i-vii regions, alternatively all seven (i-vii) regions. In some aspects, the isolated polypeptide or antigen-binding fragment thereof is directly or indirectly linked to an agent.

In another aspect, the disclosure provides a method of targeting an agent to the blood brain barrier (BBB), the method comprising (a) administering to the subject an isolated polypeptide or antigen-binding fragment described herein, wherein the isolated polypeptide is directly or indirectly linked to the agent.

In yet another aspect, the present disclosure provides a method of detecting or labeling the blood brain barrier endothelial cells (BMECs), the method comprising: contacting the blood brain barrier endothelial cells with an isolated polypeptide or antigen-binding fragment described herein wherein the isolated polypeptide is directly or indirectly linked to a detecting or imaging agent, and detecting or imaging the BMECs.

In yet another aspect, the disclosure provides an isolated polypeptide or antigen-binding fragment thereof able to specifically bind to the blood brain barrier in vivo comprising an amino acid sequence of a variable lymphocyte receptor (VLR) capable of binding the glycan antigen targets on the blood brain barrier.

The foregoing and other aspects and advantages of the invention will appear from the following description. In the description, reference is made to the accompanying drawings, which form a part hereof, and in which there are shown, by way of illustration, preferred embodiments of the invention. Such embodiments do not necessarily represent the full scope of the invention, however, and reference is made therefore to the claims and herein for interpreting the scope of the invention.

LIST OF ABBREVIATIONS

The following list of abbreviations are used in the understanding of the present invention: blood-brain barrier (BBB), brain endothelial cell (BEC), brain microvessel plasma membrane (BMPM), central nervous system (CNS), Consortium for Functional Glycomics (CFG), extracellular matrix (ECM), fluorescence activated cell sorting (FACS), gamma-glutamyl transpeptidase (GGT), glial fibrillary acidic protein (GFAP), glucose transporter (GLUT-1), insulin receptor (IR), intravenous (IV), low-density lipoprotein receptor (rLDLR), magnetic activated cell sorting (MACS), mouse brain endothelial cell (MBEC), Plasma membranes (PM), transferrin receptor (TfR), variable lymphocyte receptor (VLR), yeast display immunoprecipitation (YDIP), yeast surface display (YSD).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figures 1A, 1B, 1C, 1D:
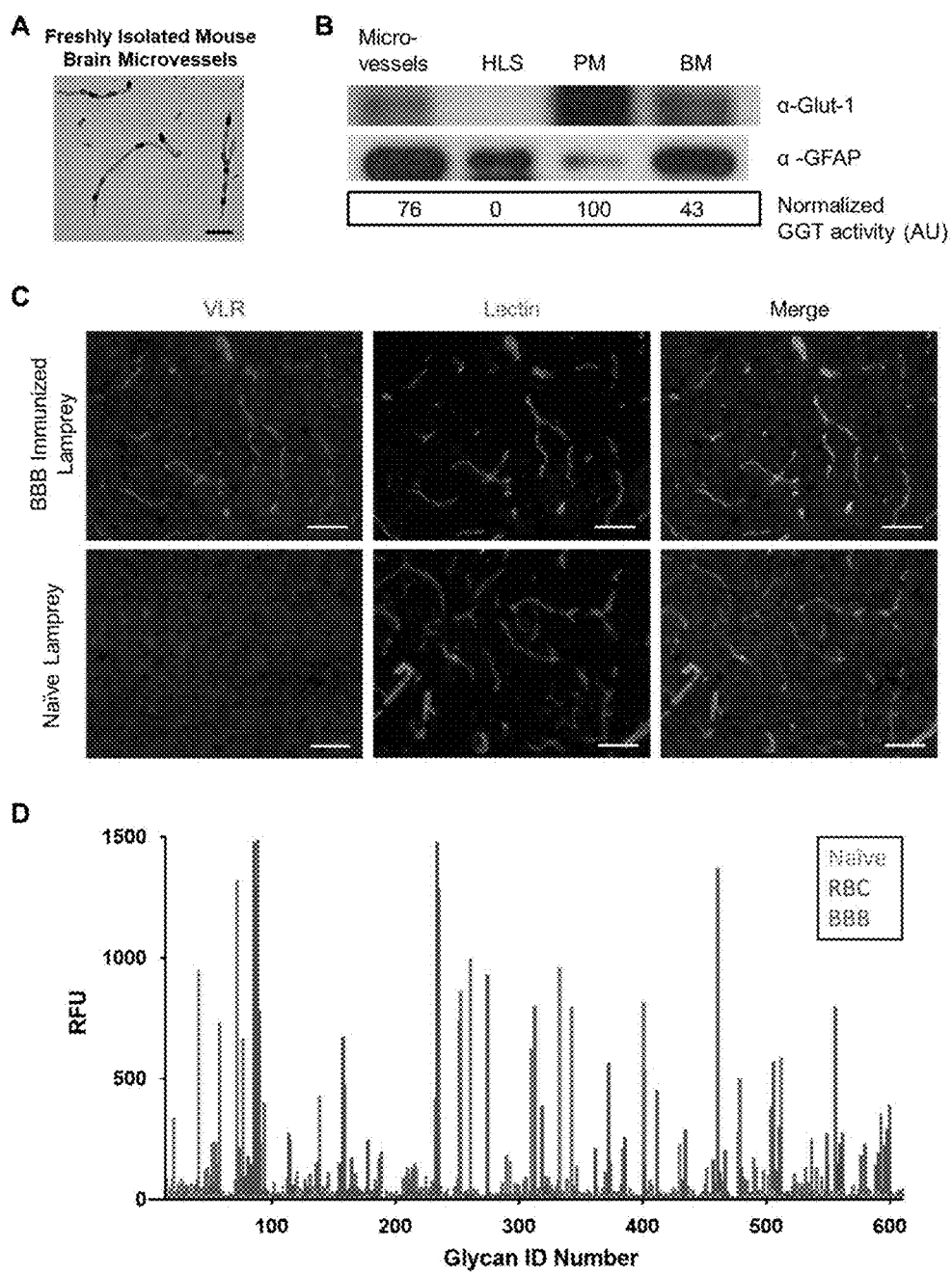
FIGS. 1A-1D. Brain microvessel plasma membrane (BMPM) isolation and lamprey immunization validation. (A) Isolated mouse brain microvessels were stained with trypan blue. Scale bar=25 µm. (B) Western blotting for Glut-1 and GFAP along with normalized GGT activity for the various fractions generated during BMPM isolation. Hypotonic lysis is used to disrupt the isolated brain microvessels. Following centrifugation, the supernatant (HLS) is separated from the lysed microvessel fragments. Sonication of the microvessel fragments and centrifugation separates the plasma membranes (PM) from the basement membrane pellet (BM). (C) Pooled plasma from BBB immunized lampreys or a plasma sample from a naïve lamprey were used to immunolabel mouse brain sections (red) and brains were counterstained with fluorescent IB4-lectin (green) to identify brain microvessels. Scale bar=50 µm. (D) Glycan microarray analysis. Plasma samples from a naïve lamprey (Naïve, gray), lamprey immunized with human erythrocytes (RBC, blue), or BMPM immunized lamprey (BBB, red) were used to probe the CFGv5.2 glycan microarray. RFU=relative fluorescenceunits.

The present invention has been described in terms of one or more preferred embodiments, and it should be appreciated that many equivalents, alternatives, variations, and modifications, aside from those expressly stated, are possible and within the scope of the invention. Before the present invention is described, it is understood that this invention is not limited to the particular methodology, protocols, and reagents described, as these may vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

The present invention provides polypeptides that specifically/selectively bind to the blood brain barrier (BBB) in vivo and compositions, method and kits for uses thereof. A new screening platform was used to address many of the aforementioned challenges of creating specific molecules that target in vivo the blood brain barrier. A recently discovered family of highly diverse leucine-rich repeat proteins termed Variable Lymphocyte Receptors (VLRs) that function as antigen receptors in the adaptive immune system of lamprey[25] were used to produce novel polypeptides comprising VLRs that are specific to the blood brain barrier in vivo. VLRs possess diversity, specificity, affinity, and stability comparable to traditional Ig-based antibodies[26,27]. Lampreys last shared a common ancestor with mammals greater than 500 million years ago. This tremendous phylogenetic distance, combined with the unique crescent-shaped geometry of the antigen-binding site, may enable VLRs to recognize new antigenic targets, including highly conserved proteins and carbohydrates that may not be well recognized by mammalian antibodies[28-33]. For example, the BBB glycocalyx has been shown to play significant roles at the BBB in health and disease[34-37], and yet has not been exploited as an antigenic source for BBB targeting.

In an attempt to leverage these potential advantages for BBB targeting, lampreys were immunized with BEC plasma membranes fractionated from mouse brain microvessels to create a library of VLRs against in vivo-relevant BBB antigens, and the immune VLR repertoire was subsequently imported into the yeast surface display (YSD) platform for screening. The immune VLR library was first screened against detergent-solubilized versions of the same brain microvessel plasma membrane preparations used for immunization to ensure enrichment of clones against in vivo antigens. Subsequently, biopanning of this enriched pool on cultured mouse BECs was used to enrich VLRs targeting extracellular epitopes. In vitro cell-binding and internalization assays revealed a subset of VLRs capable of internalization and trafficking within BECs. Three lead VLRs with prominent glycan-binding signatures were identified and shown to target and traffic within BECs in vivo.

In certain embodiments, the disclosure relates to isolated polypeptides or antigen-binding fragments thereof able to specifically and selectively bind to the BBB. By "selectively" or "specifically" we mean a polypeptide capable of binding the surface of brain vessels but does not bind other vasculature, for example, does not bind to lung, liver, or kidney tissue vasculature. By "binding", we mean that the antibodies are capable of detection at a given tissue's endothelium by standard methods (e.g., tissue section immunofluorescence assays.)

In one embodiment, the present disclosure provides an isolated polypeptide or fragment thereof able to specifically bind to the blood brain barrier in vivo comprising an amino acid sequence of a variable lymphocyte receptor (VLR) selected from the group consisting of VLR 11 (SEQ ID NO:1), VLR30 (SEQ ID NO:2), VLR46 (SEQ ID NO:3) and an amino acid sequence with at least 75%, preferably at least 80%, at least 90% or at least 95%, sequence identity to SEQ ID NO:1, SEQ ID NO:2 or SEQ ID NO:3.

In one embodiment, the present disclosure provides an isolated polypeptide or antigen-binding fragment thereof able to specifically bind to the blood brain barrier in vivo comprising an amino acid sequence of a variable lymphocyte receptor (VLR) comprising two or more of the following regions (i)-(vii):
  (i) EVRCESRSLASVPA (SEQ ID NO:5) or an amino acid sequence having at least 90% identity to SEQ ID NO:5, TVDCSGKSLASVPT (SEQ ID NO:13) or an amino acid sequence having at least 90% identity to SEQ ID NO:13, or TVDCSGKSLASVPT (SEQ ID NO:16) or an amino acid sequence having at least 90% identity to SEQ ID NO:16;
  (ii) RRLHLHR (SEQ ID NO:6) or an amino acid sequence having at least 90% identity to SEQ ID NO:6, QILRLYRNQI (SEQ ID NO: 14) or an amino acid sequence having at least 90% identity to SEQ ID NO:14, or RWLHLHR (SEQ ID NO: 17) or an amino acid sequence having at least 90% identity to SEQ ID NO:17,
  (iii) YLNLGG (SEQ ID NO:7) or an amino acid sequence having at least 90% identity to SEQ ID NO:7,
  (iv) ELKLYS (SEQ ID NO:8) or an amino acid sequence having at least 90% identity to SEQ ID NO:8,
  (v) HLDLSK (SEQ ID NO:9) or an amino acid sequence having at least 90% identity to SEQ ID NO:9,
  (vi) HAYLFG (SEQ ID NO:10) or an amino acid sequence having at least 90% identity to SEQ ID NO:10, and
  (vii) SIVMRWDGKAVNDPDSAK (SEQ ID NO:11) or an amino acid sequence having at least 90% identity to SEQ ID NO:11,
wherein the isolated peptide or antigen-binding fragment thereof is able to specifically bind to the blood brain barrier in vivo. In some embodiments, the isolated polypeptide or antigen-binding fragment thereof comprises three or more of the regions (i)-(vii), preferably four or more of the regions (i)-(vii), alternatively five or more of the regions (i)-(vii), alternatively six regions of (i)-(vii), alternatively seven of the regions (i)-(vii). Suitable sequences between the regions can be determined by one skilled in the art to provide the proper folding and conformation for maintaining the binding to the BBB, as discussed more herein.

In another embodiment, the present disclosure provides an isolated polypeptide or antigen-binding fragment thereof able to specifically bind to the blood brain barrier in vivo comprising an amino acid sequence of a variable lymphocyte receptor (VLR) comprising two or more of the following regions (i)-(vii): (i) EVRCESRSLASVPA (SEQ ID NO:5), TVDCSGKSLASVPT (SEQ ID NO:13), or TVDCSGKSLASVPT (SEQ ID NO:16); (ii) RRLHLHR (SEQ ID NO:6), QILRLYRNQI (SEQ ID NO: 14), or RWLHLHR (SEQ ID NO: 17), (iii) YLNLGG (SEQ ID NO:7), (iv) ELKLYS (SEQ ID NO:8), (v) HLDLSK (SEQ ID NO:9), (vi) HAYLFG (SEQ ID NO:10), and (vii) SIVMRWDGKAVNDPDSAK (SEQ ID NO:11), wherein the isolated peptide or antigen-binding fragment thereof is able to specifically bind to the blood brain barrier in vivo. In one example, the isolated polypeptide or antigen-binding fragment is able to be internalized and cross the blood brain barrier, wherein the polypeptide or antigen-binding fragment thereof comprises (a) EVRCESRSLASVPA (SEQ ID NO:5), RRLHLHR (SEQ ID NO:6), YLNLGG (SEQ ID NO:7), ELKLYS (SEQ ID NO:8), HLDLSK (SEQ ID NO:9), HAYLFG (SEQ ID NO:10), and SIVMRWDGKAVNDPDSAK (SEQ ID NO:11), or (b) TVDCSGKSLASVPT (SEQ ID NO:16); RWLHLHR (SEQ ID NO: 17), YLNLGG (SEQ ID NO:7), ELKLYS (SEQ ID NO:8), HLDLSK (SEQ ID NO:9), HAYLFG (SEQ ID NO:10), and SIVMRWDGKAVNDPDSAK (SEQ ID NO:11), wherein the isolated peptide or antigen-binding fragment thereof is able to specifically bind to the blood brain barrier in vivo and be internalized and cross the blood brain barrier.

In one embodiment, the isolated polypeptide or antigen-binding fragment thereof is able to be internalized and cross the blood brain barrier, wherein the polypeptide or antigen-binding fragment thereof comprises (a) EVRCESRSLASVPA (SEQ ID NO:5), RRLHLHR (SEQ ID NO:6), YLNLGG (SEQ ID NO:7), ELKLYS (SEQ ID NO:8), HLDLSK (SEQ ID NO:9), HAYLFG (SEQ ID NO:10), and SIVMRWDGKAVNDPDSAK (SEQ ID NO:11), or (b) TVDCSGKSLASVPT (SEQ ID NO:16); RWLHLHR (SEQ ID NO: 17), YLNLGG (SEQ ID NO:7), ELKLYS (SEQ ID NO:8), HLDLSK (SEQ ID NO:9), HAYLFG (SEQ ID NO:10), and SIVMRWDGKAVNDPDSAK (SEQ ID NO:11), wherein the isolated peptide or antigen-binding fragment thereof is able to specifically bind to the blood brain barrier in vivo and be internalized and cross the blood brain barrier.

In another embodiment, the isolated polypeptide or antigen-binding fragment thereof is able to bind to bind the BMEC surface, the polypeptide or antigen-binding fragment thereof comprising the regions: (i) TVDCSGKSLASVPT (SEQ ID NO:13), (ii) QILRLYRNQI (SEQ ID NO: 14), (iii) YLNLGG (SEQ ID NO:7), (iv) ELKLYS (SEQ ID NO:8), (v) HLDLSK (SEQ ID NO:9), (vi) HAYLFG (SEQ ID NO:10), and (vii) SIVMRWDGKAVNDPDSAK (SEQ ID NO:11), wherein the isolated peptide or antigen-binding fragment thereof is able to specifically bind to the BMEC surface in vivo.

In another embodiment, the isolated polypeptide or antigen-binding fragment thereof comprises a VLR comprising
(a) $(X)_{11}$EVRCESRSLASVPA$(X)_6$RRLHLHR$(X)_{18}$YLNLGG$(X)_{18}$ELKLYS $(X)_{18}$HLDLSK$(X)_{18}$HAYLFG$(X)_{21}$SIVMRWDGKAVNDPDSAK$(X)_{27}$ (SEQ ID NO: 4), wherein each X is selected from any amino acid;
(b) $(X)_{11}$TVDCSGKSLASVPT$(X)_6$QILRLYRNQI$(X)_{15}$YLNLGG$(X)_{18}$ELKLYS$(X)_{18}$HLDLSK$(X)_{18}$HAYLFG$(X)_{21}$SIVMRWDGKAVNDPDSAK$(X)_{27}$ (SEQ ID NO: 12), wherein each X is selected from any amino acid; or
(c) $(X)_{11}$TVDCSGKSLASVPT$(X)_6$RWLHLHR$(X)_{18}$YLNLGG$(X)_{18}$ELKLYS$(X)_{18}$ HLDLSK$(X)_{18}$HAYLFG$(X)_{21}$SIVMRWDGKAVNDPDSAK$(X)_{27}$ (SEQ ID NO: 15),
wherein each X is selected from any amino acid. Amino acids are known in the art, and each X can be a different amino acid as long as the isolated polypeptide or antigen-binding fragment thereof is able to maintain its ability to bind the BBB.

As used herein, the terms "proteins" and "polypeptides" are used interchangeably herein to designate a series of amino acid residues connected to the other by peptide bonds between the alpha-amino and carboxy groups of adjacent residues. The terms "protein" and "polypeptide" refer to a polymer of protein amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to an encoded gene product and fragments thereof. Thus, exemplary polypeptides or proteins include gene products, homologs, orthologs, paralogs, fragments and other equivalents, variants, fragments, and analogs of the foregoing. The isolated polypeptides of the present invention are non-naturally occurring peptides that specifically bind the blood brain barrier in vivo.

Figure 13:
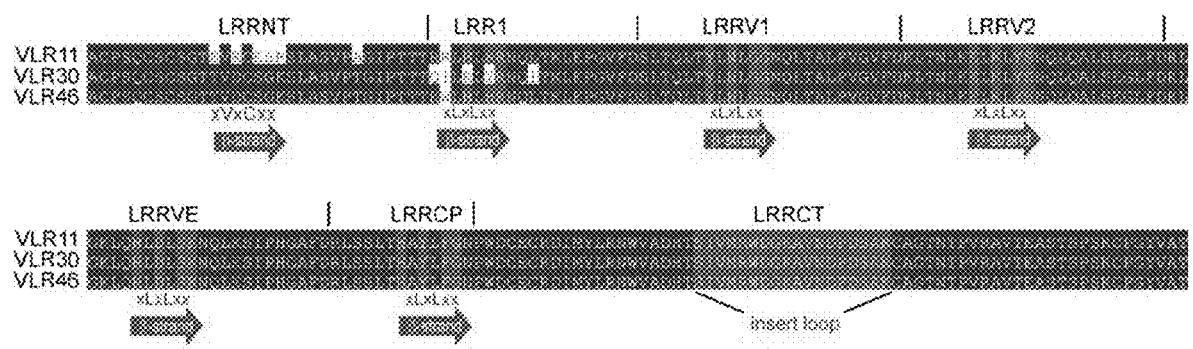
FIG. 13. Annotated sequence alignment of VLR 11 (SEQ ID NO:1), VLR 30 (SEQ ID NO:2), and VLR 46 (SEQ ID NO:3). LRR domain designations are indicated above the sequences. Sequence regions corresponding to the β-strands that form the concave antigen-binding surface of the VLR are indicated below the sequences along with conserved amino acid positions in capital letters and variable positions indicated with a red x. Amino acid positions that are conserved between clones are indicated by blue or red highlight with sequence differences denoted by lack of highlight.

Variable lymphocyte receptors, or VLRs, belong to the Leucine-rich repeat (LRR) family and mediate adaptive immune responses in jawless vertebrates, lamprey and hagfish. The VLR are often referred to as the antibodies of jawless fish. The VLRs are assembled in lymphocytes by DNA rearrangements and are as diverse as the conventional antibodies of jawed vertebrates, with the potential to make over $10^{14}$ unique receptors. VLRs are derived from the assembly of leucine-rich repeat (LRR) gene segments as opposed to the immunoglobulin V, D, and J gene subunits utilized by jawed vertebrates. The VLR consists of a set of LRR modules, each with a highly variable sequence, a 27-34-residue N-terminal LRR (LRRNT), one 25-residue LRR (LRR1), up to nine 24-residue LRRs (VRRVs, the terminal one designated LRRVe), a truncated LRR designated as a connecting peptide (LLRCP) and a 48- to 63-residue C-terminal LRR (LRRCT) as depicted in FIG. 13. Amino acid sequences of VLRs that bind the BBB are shown in the Examples. FIG. 13 depicts in red the variable regions of the LRRs.

By "antigen-binding fragment thereof" or "fragment thereof", we refer to a portion of the polypeptide that retains its ability to specifically and selectively bind to the blood brain barrier. In this application, the antigen is the blood brain barrier (e.g., blood brain membrane endothelial cells (BMECs). Suitably, the antigen-binding fragment thereof will contain the antigen-binding regions of the VLR in order to maintain its ability to selectively and specifically bind to the blood brain vasculature. One skilled in the art, using the methods described in the examples below, will readily be able to determine suitable antigen-binding fragments which are able to bind to the blood brain barrier and which do not bind to other vasculature.

The VLRs described in the present disclosure were produced by administering fractionated human blood brain barrier (e.g., blood brain barrier endothelial cells (BMEC)) plasma membranes to a lamprey wherein the lamprey produced VLRs that bind specifically to the blood brain barrier. This antigen (BMEC plasma membrane fractions) is an antigen to which lampreys are not naturally exposed, and as such, the isolated polypeptides derived from the methods are non-naturally occurring sequences.

In some embodiments, the isolated polypeptide is a recombinant polypeptide comprising a VLR sequence that is humanized. Suitably, in some embodiments, the polypeptide amino acid sequence is altered to reduce the likelihood of being seen as a foreign antigen and eliciting an immune response when administered to a human subject. Suitable methods to humanize a polypeptide are known in the art. For example, chimeric recombinant polypeptides may be created by swapping in regions of a human protein outside of the antigen-binding regions of the VLR.

In one embodiment, a VLR is humanized using the method described in U.S. patent application Ser. No. 15/308,535 ("Variable Lymphocyte Receptors (VLR) Modifications and Compositions and Uses Related Thereto", hereafter "the '535 application"), the contents of which are incorporated by reference in its entirety. For example, in one embodiment, the VLR11, VLR30 or VLR46 described herein are placed into the Slit2-D2 human scaffold (from human leucine-rich repeat receptors) as described in the '535 application. In another embodiment, the VLR may be humanized by linking the VLR to a portion of a human antibody, for example, the human Fc region of a human IgG antibody, as described in the '535 application. The antibodies disclosed in the present invention may be modified to be humanized antibodies, which include the constant region from a human germline immunoglobulin sequences. The term "recombinant human antibody" includes all human antibodies that are prepared, expressed, created or isolated by recombinant means to include the specific binding regions of the VLRs, such as antibodies isolated from a host cell such as an SP2-0, NS0 or CHO cell (like CHO K1) or from an animal (e.g., a mouse) that is transgenic for human immunoglobulin genes or polypeptides expressed using a recombinant expression vector transfected into a host cell. Such recombinant human antibodies have constant regions derived from human germline immunoglobulin sequences in a rearranged form.

In some embodiments, the isolated polypeptide has substantial identity to the polypeptide found in SEQ ID NO:1. In some embodiments, the isolated polypeptides have at least 75% sequence identity to SEQ ID NO:1, alternatively at least 80% sequence identity, alternatively at least 85% sequence identity, alternatively at least 90% sequence identity, alternatively at least 95% sequence identity, alternatively at least 97% sequence identity, alternatively at least 98% sequence identity, alternatively at least 99% sequence identity, alternatively at least 100% sequence identity. In some embodiments, the isolated polypeptide has at least 100% sequence identity within the antigen-binding regions of the VLR11.

In some embodiments, the isolated polypeptide has substantial identity to the polypeptide found in SEQ ID NO:2. In some embodiments, the isolated polypeptides have at least 75% sequence identity to SEQ ID NO:2, alternatively at least 80% sequence identity, alternatively at least 85% sequence identity, alternatively at least 90% sequence identity, alternatively at least 95% sequence identity, alternatively at least 97% sequence identity, alternatively at least 98% sequence identity, alternatively at least 99% sequence identity, alternatively at least 100% sequence identity. In some embodiments, the isolated polypeptide has at least 100% sequence identity within the antigen-binding regions of the VLR30.

In some embodiments, the isolated polypeptide has substantial identity to the polypeptide found in SEQ ID NO:3. In some embodiments, the isolated polypeptides have at least 75% sequence identity to SEQ ID NO:3, alternatively at least 80% sequence identity, alternatively at least 85% sequence identity, alternatively at least 90% sequence identity, alternatively at least 95% sequence identity, alternatively at least 97% sequence identity, alternatively at least 98% sequence identity, alternatively at least 99% sequence identity, alternatively at least 100% sequence identity. In some embodiments, the isolated polypeptide has at least 100% sequence identity within the antigen-binding regions of the VLR46.

The term "substantial identity" of polynucleotide sequences means that a polynucleotide comprises a sequence that has at least 75% sequence identity to the polynucleotide encoding the polypeptide of interest described herein. Alternatively, percent identity can be any integer from 75% to 100%. In one embodiment, the sequence identity is at least 90%, alternatively at least 95%. More preferred embodiments include at least: 75%, 80%, 85%, 86%, 87%, 88%, 89%, 90%, 91%, 92%, 93%, 94%, 95%, 96%, 97%, 98% or 99% compared to a reference sequence using the programs described herein; preferably BLAST using standard parameters, as described. These values can be appropriately adjusted to determine corresponding identity of proteins encoded by two nucleotide sequences by taking into account codon degeneracy, amino acid similarity, reading frame positioning and the like.

In some preferred embodiments, the term "substantial identity" of amino acid sequences for purposes of this invention means polypeptide sequence identity of at least 75%. Preferred percent identity of polypeptides can be any integer from 75% to 100%. More preferred embodiments include at least 75%, 80%, 85%, 86%, 87%, 88%, 89%, 90%, 91%, 92%, 93%, 94%, 95%, 96%, 97%, 98%, %, or 99%. In one embodiment, the sequence identity is at least 90%, alternatively at least 95%.

In one embodiment, polypeptides able to be internalized and cross the BBB are provided. For example, in one embodiment, the polypeptide comprises VLR11 (SEQ ID NO:1) or antigen-binding fragments thereof. In another example, the polypeptide comprises VLR46 (SEQ ID NO:3) or antigen-binding fragments thereof.

In another embodiment, isolated polypeptides able to bind the BMEC surface are provided. In one example, the polypeptide comprises VLR30 (SEQ ID NO:2) or antigen-binding fragments thereof. In another embodiment, a polypeptide able to bind brain parenchymal cells is provided, particularly, in one suitable example, the polypeptide comprises VLR30 (SEQ ID NO:2) or antigen-binding fragments thereof.

Figures 6A, 6B, 6C:
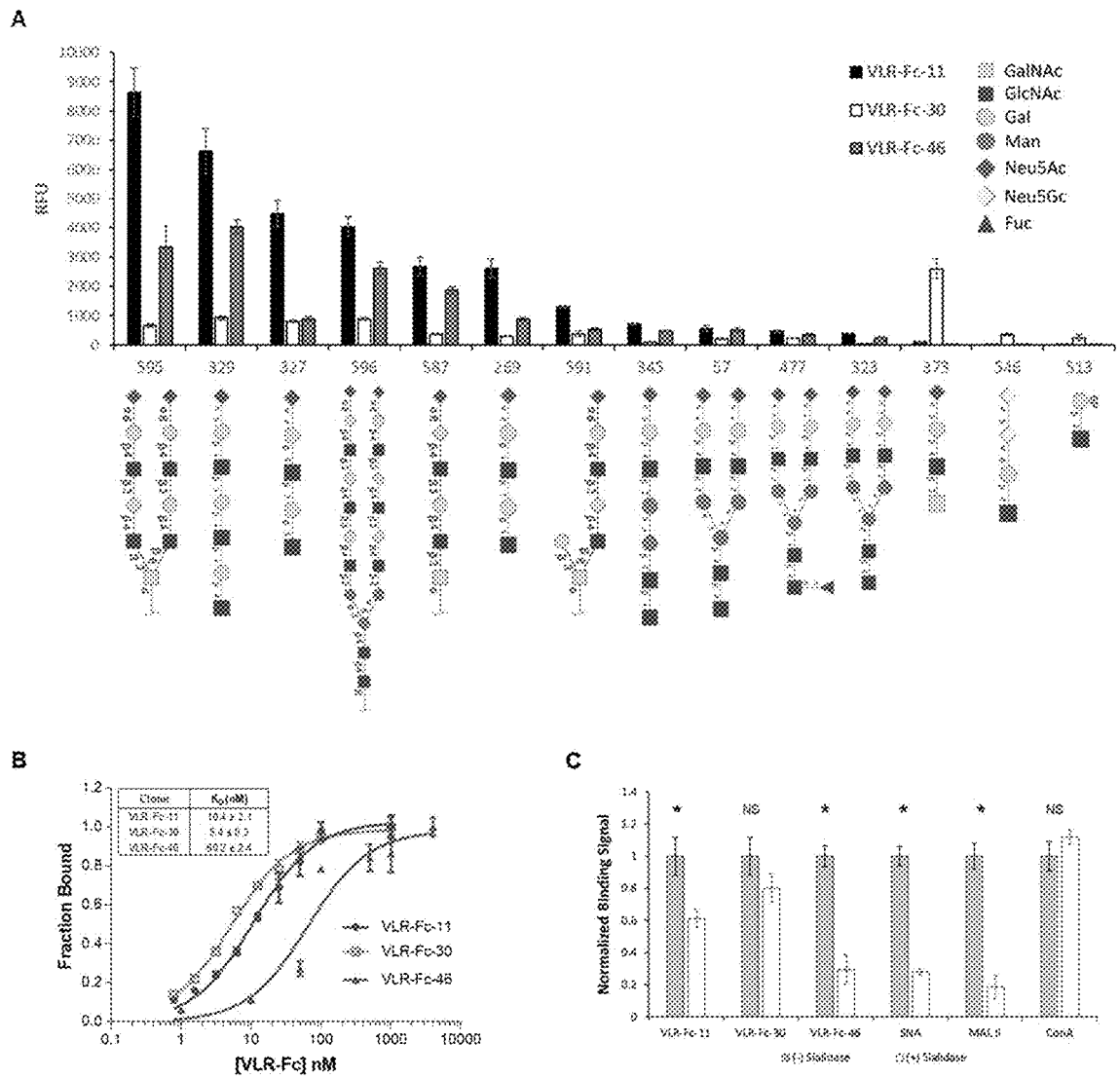
FIGS. 6A-6C. Antigen-binding characterization of lead VLR-Fc clones. (A) VLR-Fc binding to glycans on the CFGv5.3 mammalian glycan array. Comparison of binding strength of the top 10 glycans recognized by each VLR-Fc is shown and rank ordered by VLR-Fc-11 binding intensity. The glycan ID number and structure are shown along the x-axis. RFU (relative fluorescence units) is plotted as mean±S.D. (B) Apparent affinity of each VLR-Fc was measured via equilibrium titration on cultured MBECs. The mean fitted equilibrium dissociation constant (KD)±the 95% confidence interval calculated from n=3 independent titrations is reported. (C) VLR-Fc or lectin binding to MBEC monolayers with and without sialidase pre-treatment. For each protein tested, the background-subtracted binding signal is normalized to MBEC binding without sialidase pre-treatment. VLR-Fc are compared to lectins that bind α2-3 (MAL II) or α2-6 (SNA) linked sialic acids and ConA which binds to α-linked core mannose residues. The mean±S.D. is plotted. A students t-test on n=6 replicates was used to determine statistical significance *=p<0.05, NS=not significant. SNA=*Sambucus nigra* lectin, MAL II=*Maackia amurensis* lectin 2, ConA=Concanavalin A.

In some embodiments, the present disclosure provides an isolated polypeptide or antigen-binding fragment thereof able to specifically bind to the blood brain barrier in vivo comprising an amino acid sequence of a variable lymphocyte receptor (VLR) capable of binding glycan antigen targets on the blood brain barrier, the glycan targets found in Table 2 (FIG. 9) and FIG. 6A. For example, the glycan antigen target on the blood brain barrier endothelium can be selected from Neu5Aca2-6Galb1-4GlcNAcb1-3Galb1-4GlcNAcb1-6(Neu5Aca2-6Galb 1-4GlcNAcb1-3Galb 1-4GlcNAcb 1 3)G alNAca-Sp 14, Neu5Aca2-6Galb1-4GlcNAcb1-3Galb1-4GlcNAcb1-3G alb 1-4 GlcNAcb-S pO, Neu5Aca2-6Galb1-4GlcNAcb 1-3 Galb 1-3 GlcNAcb-SpO, Neu5Aca2-6Galb 1-4GlcNAcb 1-3 Galb 1-4GlcNAcb 1-3Galb 1-4GlcNAcb 1-2M ana1-6(Neu5Aca2-6Galb1-4GlcNAcb1-3Galb 1-4GlcNAcb1-3Galb 1-4GlcNAcb 1-2M ana 1-3)M anb 1-4 GI cNAcb 1-4 GI cNAcb-S p 1 2, Neu5Aca2-6Galb1-4GlcNAcb1-3Galb1-4GlcNAcb1-3G alNAca-Sp 14, Neu5Aca2-6Galb1-4GlcNAcb1-3Galb1-4GlcNAcb-SpO, as depicted in Table 2. In one example, the isolated polypeptide or antigen-binding fragment thereof binds glycan antigen target of the blood brain barrier, wherein the glycan target is a Neu5Aca2-6Galβ1-4GlcNAcβ1-3Gal motif. These polypeptides or fragments thereof are able to be internalized and cross the BBB (e.g., engage and traffic within the BBB), for example, the VRL11 or VRL46, as described above. VLR-Fcs-11 and -46 exhibited a similar rank ordering of binding to glycan targets in FIGS. 6A-6C and a clear preference for terminal α2-6 linked sialic acid structures having the Neu5Aca2-6Galβ1-4GlcNAc motif with a preference for a β1-3Gal linkage after the GlcNac residue.

In another embodiment, the isolated polypeptide or antigen-binding fragment thereof is capable of binding the glycan antigen target is Neu5Aca2-6Galβ1-4GlcNAcβ1-3GalNAc motif on the surface of the BBB endothelium. For example, the polypeptide may be VLR-30 or an antigen-binding fragment thereof. The binding profile of VLR-Fc-30 appears to be distinct with a Neu5Aca2-6Galβ1-4GlcNAcβ1-3GalNAc motif not recognized by VLR-Fc-11 or -46 yielding the highest binding signal.

In some embodiments, the isolated polypeptide or antigen-binding fragment thereof is directly or indirectly linked to an agent. In some embodiments, the isolated polypeptide or antigen-binding fragment thereof is covalently or noncovalently linked to an agent. In some embodiments, the isolated polypeptide or antigen-binding fragment thereof is conjugated to the agent. In other embodiments, the agent is a polypeptide, wherein the polypeptide is translated concurrently with the VLR polypeptide sequence.

In some embodiments, the agent is selected from the group consisting of a therapeutic agent, pharmaceutical agent, a diagnostic agent, an imaging agent, a detection agent, an immunological therapeutic construct, and a combination thereof.

The term "agent" as used herein includes any useful moiety that allows for the purification, identification, detection, diagnosing, imaging, or therapeutic use of the polypeptide of the present invention. The term agent includes epitope tags, detection markers and/or imaging moieties, including, for example, enzymatic markers, fluorescence markers, radioactive markers, among others. Additionally, the term agent includes therapeutic agents, pharmaceutical agents and compounds, small molecules, and drugs, among others. The term agent also includes diagnostic agents. The agent to be attached to a polypeptide described herein is selected according to the purpose of the intended application (i.e., treatment of a particular disease). Such agents may include but are not limited to, for example, pharmaceutical agents, biologics, toxins, fragments of toxins, alkylating agents, enzymes, antibiotics, antimetabolites, antiproliferative agents, hormones, neurotransmitters, DNA, RNA, siRNA, oligonucleotides, antisense RNA, aptamers, diagnostics, radioopaque dyes, radioactive isotopes, fluorogenic compounds, magnetic labels, nanoparticles, marker compounds, lectins, compounds which alter cell membrane permeability, photochemical compounds, small molecules, liposomes, micelles, gene therapy vectors, viral vectors, and the like.

The agents may be linked via cleavable or non-cleavable linkers to the polypeptides described herein. Suitable linkers are known in the art.

In some embodiments, the polypeptide is linked to a biologic that can be targeted to the brain or BBB. For example, in one embodiment, the biologics include, but are not limited to, for example, proteinaceous components, for example, other antibody binding domains, trophic factors, neuroactive peptides, among others. For use herein, the term "polypeptide conjugate" includes a polypeptide described above linked directly or indirectly to an agent.

Suitable epitope tags are known in the art and include, but are not limited to, 6-Histidine (His, HHHHHH, SEQ ID NO:18) cMyc (EQKLISEEDL, SEQ ID NO:19), FLAG (DYKDDDDK, SEQ ID NO:20), V5-tag (GKPIPN-PLLGLDST, SEQ ID NO:21), HA-tag (YPYDVPDYA, SEQ ID NO:22), NE-tag (TKENPRSNQEESYDDNES, SEQ ID NO:23), S-tag (KETAAAKFERQHMDS, SEQ ID NO:24), Ty tag (EVHTNQDPLD, SEQ ID NO:25), among others. Epitope tags are commonly used as a purification tag. A purification tag is an agent that allows isolation of the polypeptide from other non-specific proteins.

In one embodiment of the invention, the polypeptide of the invention is linked with an agent, for example, with a detectable marker, preferably a fluorescent, enzymatic or a luminescent marker. Examples of suitable enzymes include, but are not limited to, horseradish peroxidase, alkaline phosphatase, beta-galactosidase, glucose-6-phosphatase, or acetylcholinesterase. Examples of suitable tags comprising prosthetic group complexes include, but are not limited to, streptavidin/biotin and avidin/biotin. Examples of suitable fluorescent materials include, but are not limited to, fluorescein, fluorescein isothiocyanate, rhodamine, dichlorot[pi]azinylamine fluorescein, green fluorescent protein (GFP), red fluorescent protein (RFP), blue fluorescent dyes excited at wavelengths in the ultraviolet (UV) part of the spectrum (e.g. AMCA (7-amino-4-methylcoumarin-3-acetic acid); Alexa Fluor 350), green fluorescent dyes excited by blue light (e.g. FITC, Cy2, Alexa Fluor 488), red fluorescent dyes excited by green light (e.g. rhodamines, Texas Red, Cy3, Alexa Fluor dyes 546, 564 and 594), or dyes excited with infrared light (e.g. Cy5) to be visualized with electronic detectors (CCD cameras, photomultipliers); dansyl chloride, phycoerythrin or the like.

Suitable examples of radioactive material include, but are not limited to, $^{125}$I, $^{131}$I, $^{35}$S or $^{3}$H. In some embodiments, the polypeptide is directly or indirectly linked to a radio-isotope, an NMR or MRI contrast agent or nanoparticles for diagnosing, imaging and treatment. Suitable radioisotopes include, but are not limited to, $^{18}$F, $^{11}$C, $^{13}$N, $^{15}$O, $^{68}$Ga, $^{82}$Rb, $^{44}$Sc, $^{64}$Cu, $^{86}$Y, $^{89}$Zr, $^{124}$I, $^{152}$Tb that can be used for PET imaging or $^{67}$Ga, $^{81m}$Kr, $^{99m}$Tc, $^{111}$In, $^{123}$I, $^{125}$I, $^{133}$Xe, $^{201}$Tl, $^{155}$Tb, $^{195m}$Pt that can be used for SPECT/scintigraphic studies, or $^{14}$C, $^{3}$H, $^{35}$S, $^{32}$P, $^{125}$I that can be used for autoradiography or in situ hybridization, or $^{211}$At—, $^{212}$Bi—, $^{75}$Br—, $^{76}$Br—, $^{131}$I—, $^{111}$In, $^{177}$Lu—, $^{212}$Pb, $^{186}$Re—, $^{188}$Re—, $^{153}$Sm—, $^{90}$Y that can be used to label the polypeptides. Suitable NMR. or MRI contrast agents are known in the art and include, but are not limited to, for example paramagnetic agents gadolinium (Gd), dysprosium (Dy) and manganese (Mn), and the superparamagnetic agents based on iron oxide (such as MION, SPIO or USPIO) or iron platinium (SIPP), and X-nuclei such as $^{18}$F, $^{13}$C, $^{23}$Na, $^{17}$O, $^{15}$N.

Suitable nanoparticles, including metal nanoparticles and other metal chelates, are known in the art and include, but are not limited to, for example, gold nanoparticles (B. Van de Broek et al., ACSNano, Vol. 5, No. 6, 4319-4328, 2011), quantum dots (A. Sukhanova et al., Nanomedicine, 8 (2012) 516-525), magnetic nanoparticles ($Fe_3O_4$), silver nanoparticles, nanoshells and nanocages.

In further embodiments, the agent is a therapeutic agent. As used herein, the term "therapeutic agent" refers to any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, biologics, chemotherapeutics, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, substances used for the treatment, prevention, diagnosis, cure or mitigation of a disease or illness; substances that affect the structure or function of the body, or pro-drugs, which become biologically active or more active after they have been placed in a physiological environment.

As used herein, the term "conjugate" refers to the joining of two entities by covalent bonds. The entities may be covalently bonded directly or through linking groups using standard synthetic coupling procedures. For examples, two polypeptides may be linked together by simultaneous polypeptide expression typically referred to as a fusion or chimeric protein. One or more amino acids may be inserted into polypeptide as a linking group by incorporation of corresponding nucleic acid sequences into the expression vector. Other contemplated linking groups include polyethylene glycols or hydrocarbons terminally substituted with amino or carboxylic acid groups to allow for amide coupling with polypeptides having amino acids side chains with carboxylic acid or amino groups, respectively. Alternatively, the amino and carboxylic acid groups can be substituted with other binding partners such as an azide and an alkyne, which undergo copper catalyzed formation of triazoles.

In another example of conjugation, polypeptides are expressed to contain naturally or non-naturally occurring amino acids containing a thiol group. The thiol group can be substituted for an amino group in coupling reactions with carboxylic acids, or two thiol groups when exposed to oxidative conditions react to form disulfides. Additionally, in some embodiments, non-naturally occurring amino acids are incorporated into the polypeptide, allowing for site-specific conjugation of the polypeptide to one or more agents. For example, in one embodiment, the use of selenocysteine allows for the site-specific conjugation of the polypeptides of the present invention to suitable agents.

In general, methods of conjugating, linking and coupling polypeptides to pharmacologically active compounds are well known in the field. For example, methods of conjugating antibodies can also be used to conjugate polypeptides, see, for example, Wu A M, Senter P D, Arming antibodies: prospects and challenges for immunoconjugates, Nat Biotechnol. 2005 September; 23(9):1137-46 and Trail P A, King H D, Dubowchik G M, Monoclonal antibody drug immunoconjugates for targeted treatment of cancer, Cancer Immunol Immunother. 2003 May; 52(5):328-37; Saito G, Swanson J A, Lee K D. Drug delivery strategy utilizing conjugation via reversible disulfide linkages: role and site of cellular reducing activities, Adv Drug Deliv Rev. 2003 Feb. 10; 55(2):199-215.

Further embodiments contemplated include polypeptide-drug conjugates. For example, suitable drugs may be conjugated to the polypeptides or antigen-binding fragments described herein with a cleavable or non-cleavable linker. Cleavable and non-cleavable linkers are known in the art.

Conventional linking methods of linking a substance of interest to a polypeptide are known in the art (e.g., See Ternynck and Avrameas, 1987, "Techniques immunoenzy-matiques" Ed. INSERM, Paris or G. T. Hermanson, Bioconjugate Techniques, 2010, Academic Press). Many chemical cross-linking methods are also known in the art. Cross-linking reagents may be homobifunctional (i.e., having two functional groups that undergo the same reaction) or heterobifunctional (i.e., having two different functional groups). Numerous cross-linking reagents are commercially available. Detailed instructions for their use are readily available from the commercial suppliers. For a general reference on polypeptide cross-linking and conjugate preparation, see WONG, Chemistry of protein conjugation and cross-linking, CRC Press (1991).

In some embodiments, the polypeptides may be provided in combination with liposome, nanoparticles or other analogous carriers loaded with a pharmaceutically active compound. Methods of preparing such compositions are known in the field (see, for example, Sugano et al., Antibody Targeting of Doxorubicin-loaded Liposomes Suppresses the Growth and Metastatic Spread of Established Human Lung Tumor Xenografts in Severe Combined Immunodeficient Mice Cancer Research 60, 6942-6949, Dec. 15, 2000 and Martin et al., Nanomaterials in Analytical Chemistry, Analytical Chemistry News &Features, May 1, 1998; pp. 322 A-327 A). As used herein, the phrase "isolated polypeptide in combination with a pharmaceutically active compound" shall not be limited by the method of manufacture and such compositions may be produced by, but not limited to, techniques of conjugating, linking, coupling and decorating known in the art.

In some embodiments, the agent can be a portion or fraction of an immunoglobulin (i.e., antibody). For example, in one embodiment, the agent can be an Fc portion of an antibody. The Fc regions define the class (or isotype) of antibody (e.g., IgG) and are responsible for binding a number of natural proteins to elicit important biochemical events. The Fc region of an antibody interacts with a number of ligands including Fc receptors and other ligands, imparting an array of important effector functions. In one embodiment, the agent is the Fc of a human IgG. Other portions of antibodies may also be used to create recombinant antibodies and are known in the art. Suitably, the Fc portion of the Ig may be from a mammalian immunoglobulin (e.g., rabbit, rat, human, etc), preferably in one embodiment, from a human Ig.

One may wish to express the isolated polypeptide as a fusion protein with a pharmacologically or therapeutically relevant peptide. For example, one may wish to express the VLR with a protein linker and a protein therapeutic. Standard molecular biology techniques (e.g., restriction enzyme based subcloning, or homology based subcloning) could be used to place the DNA sequence encoding a protein therapeutic in frame with the VLR within the targeting vector (usually a protein linker is also added to avoid steric hindrance). The fusion protein is then produced as one peptide in a host cell (e.g., yeast, bacteria, insect, or mammalian cell) and purified before use. Note the therapeutic does not need to be a whole protein. (For example, it can be a single peptide chain as a subunit in a protein with more than one peptide. The other peptides can be co-expressed with the vector fusion and allowed to associate in the host cell or after secretion). For example, in one embodiment, the fusion protein may be the amino acid sequence comprising the VLR and the amino acid sequence of human Fc IgG.

In some embodiments, the present disclosure provides compositions comprising the isolated polypeptide and a pharmaceutical acceptable carrier.

The present disclosure provides compositions comprising a polypeptide specific for BBB in vivo described above. In some embodiments, the composition is a pharmaceutical composition comprising the polypeptide specific for BBB and a pharmaceutically acceptable carrier. Compositions are provided that include one or more of the disclosed polypeptides that bind BBB. Compositions comprising polypeptides that are conjugated to and/or directly or indirectly linked to an agent are also provided. The compositions can be prepared in unit dosaged forms for administration to a subject. The amount and timing of administration are at the discretion of the treating clinician to achieve the desired outcome. The polypeptide can be formulated in the composition for systemic or local (such as intravenous, intrathecal, intracranial) administration depending on the specific method for use (e.g., detection, diagnostic, treatment (e.g., administered with a therapeutic or pharmaceutical agent). In one example, the polypeptide is formulated for parenteral administration, such as intravenous administration.

In some embodiments, the composition comprises effective amounts of the polypeptide and a pharmaceutical agent together with a pharmaceutically acceptable carrier.

"Pharmaceutically acceptable" carriers are known in the art and include, but are not limited to, for example, suitable diluents, preservatives, solubilizers, emulsifiers, liposomes, nanoparticles and adjuvants. Pharmaceutically acceptable carriers are well known to those skilled in the art and include, but are not limited to, 0.01 to 0.1M and preferably 0.05M phosphate buffer or 0.9% saline. Additionally, such pharmaceutically acceptable carriers may be aqueous or non-aqueous solutions, suspensions, and emulsions. Examples of nonaqueous solvents are propylene glycol, polyethylene glycol, vegetable oils such as olive oil, and injectable organic esters such as ethyl oleate. Aqueous carriers include isotonic solutions, alcoholic/aqueous solutions, emulsions or suspensions, including saline and buffered media. Water is not contemplated as a suitable physiologically acceptable carrier. In some embodiments, additional components may be add to preserve the structure and function of the viruses, vectors or polypeptides of the present invention, but are physiologically acceptable for administration to a subject.

Compositions of the present disclosure may include liquids or lyophilized or otherwise dried formulations and may include diluents of various buffer content (e.g., Tris-HCl, acetate, phosphate), pH and ionic strength, additives such as albumin or gelatin to prevent absorption to surfaces, detergents (e. g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the polypeptide, complexation with metal ions, or incorporation of the material into or onto particulate preparations of polymeric compounds such as polylactic acid, polyglycolic acid, hydrogels, etc., or onto liposomes, microemulsions, micelles, milamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

In some embodiments, the compositions comprise a pharmaceutically acceptable carrier, for example, buffered saline, and the like. The compositions can be sterilized by conventional, well-known sterilization techniques. The compositions may contain pharmaceutically acceptable additional substances as required to approximate physiological conditions such as a pH adjusting and buffering agent, toxicity adjusting agents, such as, sodium acetate, sodium chloride, potassium chloride, calcium chloride, sodium lactate, and the like.

In some embodiments, the polypeptides are provided in lyophilized form and rehydrated with sterile water or saline solution before administration.

Further embodiments provide an isolated nucleic acid sequence that encodes for the polypeptides described above. Some embodiments provide an isolated polynucleotide encoding the polypeptide described herein. In some embodiments, the isolated polynucleotide encodes the VLR comprising SEQ ID NO:1, SEQ ID NO:2 or SEQ ID NO:3. In some embodiments, the isolated nucleic acid sequence encoding the isolated polypeptide or antigen-binding fragments thereof described herein is provided.

A recombinant expression cassette comprising a polynucleotide encoding the polypeptide of the present invention is also contemplated. The polynucleotide may be under the control of a transcriptional promoter allowing the regulation of the transcription of said polynucleotide in a host cell.

The present invention also provides a recombinant expression cassette comprising a polynucleotide according to the present invention under the control of a transcriptional promoter allowing the regulation of the transcription of said polynucleotide in a host cell. Said polynucleotide can also be linked to appropriate control sequences allowing the regulation of its translation in a host cell.

The present invention also provides a recombinant vector (e.g., a recombinant expression vector) comprising a polynucleotide according to the present invention. Advantageously, said recombinant vector is a recombinant expression vector comprising an expression cassette according to the present invention.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors". Vectors, including expression vectors, comprise the nucleotide sequence encoding for the polypeptides described herein and a heterogeneous sequence necessary for proper propagation of the vector and expression of the encoded polypeptide. The heterogeneous sequence is sequence from a difference species than the polypeptide.

The present invention also provides a host cell containing a recombinant expression cassette or a recombinant expression vector according to the present invention. The host cell is either a prokaryotic or eukaryotic host cell. The host cell is capable of expressing the polypeptides of the present invention. Suitable host cells include, but are not limited to, mammalian cells and yeast cells. In some embodiments, the host cell may be a eukaryotic cell. The terms "host cell" refers to a cell into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The present invention contemplates methods of delivering an agent, for example, but not limited to, a pharmaceutically active or otherwise therapeutic compound to and/or across the blood-brain barrier into a subject's brain. Such a method includes administering a composition comprising the isolated polypeptide described herein and an agent, for example, a pharmaceutically active or therapeutic compound to a subject. The isolated polypeptide directs delivery of the agent to and/or across the blood brain barrier into the subject's brain. As described in more detail above, the agent may be directly or indirectly linked to the isolated polypeptide specific for the BBB. In one embodiment, the polypeptide is able to be internalized by BMECs and cross the blood brain barrier. Suitable peptides able to cross the BBB include, for example, polypeptide comprising VLR11 (SEQ ID NO:1) or polypeptide comprising VLR46 (SEQ ID NO:3).

Another embodiment of the present invention provides a method of detecting and labeling brain vasculature within a subject. The method comprises administering to the subject an isolated polypeptide specific to BBB as described herein. In some instances, the method can be performed before brain surgery to assess the blood brain barrier. In some embodiments, the isolated polypeptide may be conjugated to an imaging or fluorescent or other visualizable agent that can be used to detect the brain vasculature within the brain. Methods of imaging are known in the art and include, but are not limited to, for example, PET scan, MRI scan, CT scan, NMR, among others.

The present invention also contemplates methods of detecting or imaging the brain vasculature within a subject. The method comprises, administering to the patient a suitable amount of the isolated polypeptide directly or indirectly linked with a diagnostic or detecting agent.

Another embodiment provides a method of imaging BBB in a subject comprising (a) administering to the subject an isolated polypeptide comprising a VLR described herein conjugated to an imaging agent, and (b) visualizing the localization of the polypeptide in the subject. Methods of visualizing the polypeptide are known in the art, and will depend on the imaging agent attached to the polypeptide, as described above. Suitable methods of visualization of the BBB within the subject include, but are not limited to, PET scan, MRI scan, CT scan, among others. In some embodiments, the visualization occurs in the brain of the subject.

The polypeptides or antigen fragments thereof can be used as a diagnostic tool, both in the clinical and laboratory setting (e.g., in vitro and in vivo). Suitable diagnostic uses include, but are not limited to, for example, detection, labeling and imaging of BBB using the polypeptides or antigen-binding fragments thereof described herein. In one embodiment, the present disclosure provides a method of detecting BBB in a sample, the method comprising contacting the sample with the polypeptide or antigen-binding fragment thereof and detecting the polypeptide or antigen-binding fragment thereof within the sample. Suitable methods of detection include, but are not limited to, for example, visualization or imaging of a labeled polypeptide or antigen-binding fragment thereof. In vitro methods of visualization can be by microscope (e.g., fluorescence microscopy), flow cytometry, cryo-imaging, 3-D imaging, and the like. Suitable methods of in vivo visualization include, but are not limited to, for example, PET scan, MM scan, CT scan, NMR, among others.

In some embodiments, the isolated polypeptide is administered directly to brain of a subject, or via intrathecal injection, or intravenously to the subject.

As used herein, "subject" or "patient" refers to mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex. In one specific embodiment, a subject is a mammal, preferably a human.

As used herein, the terms "administering" and "administration" refer to any method of providing a pharmaceutical preparation or composition to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, intradermal administration, intrathecal administration and subcutaneous administration. Administration can be continuous or intermittent. In various aspects, a preparation can be administered therapeutically; that is, administered to treat an existing disease or condition. In a preferred embodiment, the administration is intracerebral administration or intravenous administration.

Another embodiment provides methods and kits of assaying the presence of brain vasculature cells within a sample. The method comprises contacting the sample with the polypeptide specific to BBB, and detecting the presence of binding. In some embodiments, the detecting is done by flow cytometry. In other embodiments, magnetic beads are used to isolate and quantify the cells that are able to bind to the antibody from within a sample. In other embodiments, methods of using ELISA are used to confirm the presence of brain vasculature cells within a sample. In another embodiment, the method or kit is used for in vivo detection wherein a detection agent is used. For in vivo detection, the polypeptide is administered to the subject, either systemically (e.g., intravenously) or locally (e.g., intracranially).

For purposes of the present invention, "treating" or "treatment" describes the management and care of a subject for combating the disease, condition, or disorder. Treating includes the administration of a polypeptide of present invention in combination with a therapeutic or pharmaceutical agent for preventing the onset of the symptoms or complications, alleviating the symptoms or complications, or eliminating the disease, condition, or disorder.

In some embodiments, kits for carrying out the methods described herein are provided. The kits provided may contain the necessary components with which to carry out one or more of the above-noted methods.

The present invention has been described in terms of one or more preferred embodiments, and it should be appreciated that many equivalents, alternatives, variations, and modifications, aside from those expressly stated, are possible and within the scope of the invention.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. For example, with regard to sequences "consisting of" refers to the sequence listed in the SEQ ID NO. and does refer to larger sequences that may contain the SEQ ID as a portion thereof.

The invention will be more fully understood upon consideration of the following non-limiting examples.

The present invention has been described in terms of one or more preferred embodiments, and it should be appreciated that many equivalents, alternatives, variations, and modifications, aside from those expressly stated, are possible and within the scope of the invention.

The invention will be more fully understood upon consideration of the following non-limiting examples.

EXAMPLES

Example 1: Development of Variable Lymphocyte Receptors (VLRs) Specific for the Blood Brain Barrier A new screening platform was used to address many of the challenges of producing BBB specific antibodies. We deployed a recently discovered family of highly diverse leucine-rich repeat proteins termed VLRs. Lampreys were immunized with BEC plasma membranes fractionated from mouse brain microvessels to create a library of VLRs against in vivo-relevant BBB antigens, and the immune VLR repertoire was subsequently imported into the yeast surface display (YSD) platform for screening. The immune VLR library was first screened against detergent-solubilized versions of the same brain microvessel plasma membrane preparations used for immunization to ensure enrichment of clones against in vivo antigens. Subsequently, biopanning of this enriched pool on cultured mouse BECs was used to enrich VLRs targeting extracellular epitopes. In vitro cell-binding and internalization assays revealed a subset of VLRs capable of internalization and trafficking within BECs. Three lead VLRs with prominent glycan-binding signatures were identified and shown to target and traffic within BECs in vivo.

Results

Lamprey Immunization and Yeast Display Library Construction

Brain microvessels were isolated from mice cortices using mechanical homogenization and filtration techniques (FIG. 1A). Plasma membranes (PM) were fractionated from the basement membranes of the microvessels via hypotonic lysis, sonication and centrifugation as previously described[38]. Assessment of the preparations indicated that the endothelial PM-resident glucose transporter (Glut-1) and gamma-glutamyl transpeptidase (GGT) enzyme were enriched in the PM fraction while the astrocyte marker, glial fibrillary acidic protein (GFAP), was de-enriched (FIG. 1B). Such a brain microvessel PM (BMPM) antigen preparation has been previously used as an appropriate immunogen for multiplex expression cloning of BBB membrane proteins[23], and was used here as a representative in vivo-relevant BBB protein source for lamprey immunization and VLR library screening.

Three lampreys were immunized with 50 μg of BMPM protein and boosted two additional times over 6 weeks to elicit a VLR immune response against mouse BBB antigens. Two weeks after the final immunization, lamprey plasma and lymphocytes were harvested. Mouse brain cryosections were labeled using pooled plasma from the BBB immunized lampreys to determine if the lampreys responded to the immunization. Brain microvessels were clearly labeled with the polyclonal VLR-containing plasma pooled from all three immunized lampreys (FIG. 1C), whereas plasma from naïve lamprey did not elicit a vascular-specific signature. These results indicated that the lamprey immune system generated a specific response against BMPM antigens. In addition, when the VLRB-containing plasma was used to probe a glycan microarray, there was a distinct glyco-signature for the BMPM immunized lampreys compared to human red blood cell immunized lampreys or naïve lampreys (FIG. 1D). To efficiently screen for monoclonal BBB-binding VLRs present in the immune repertoire, a YSD library termed BBBVLR, was constructed (FIG. 2i). VLR genes were recovered by PCR of total lymphocyte cDNA with VLRB-specific primers and assembled by homologous recombination with the YSD vector to create an immune VLR YSD library of 7.5×10$^6$ VLR clones (See Materials and Methods for details).

Screening of VLR Library

Figure 2:
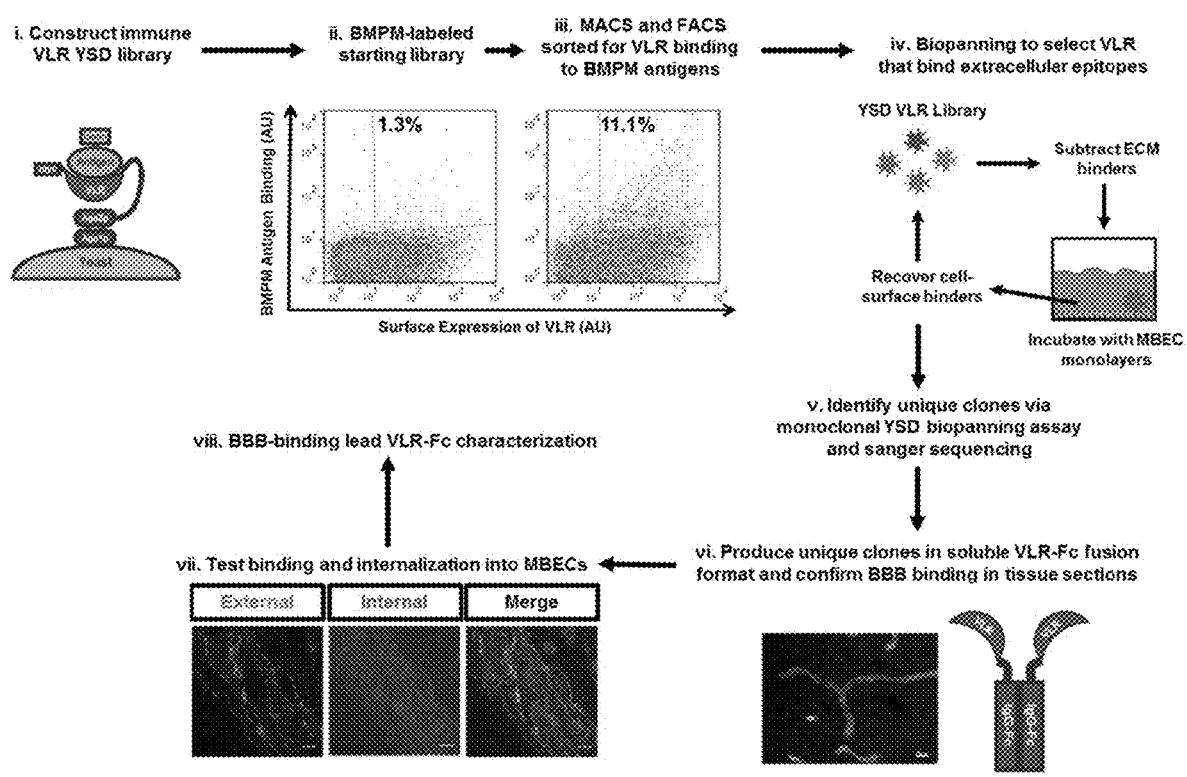
FIG. 2. BBBVLR library screening and characterization workflow. i) Immunized lamprey. BBBVLR libraries are expressed on the yeast surface by fusion to the C-terminus of the Aga2p protein. Each yeast cell displays thousands of copies of a single VLR clone on its surface. ii) and iii) The immune, unsorted library is enriched for binders to BBB antigens expressed in vivo via MACS and FACS with detergent-solubilized BMPMs. The percentage of antigen-binding yeast clones before ii) and after iii) sorting are reported. iv) The FACS-enriched BMPM-binding pool is next screened for VLRs that bind extracellular domains of BMPM epitopes via biopanning against a murine brain microvessel endothelial cell line (MBEC) while also employing negative selection against ECM in each round. v) Unique MBEC binding clones are identified via a monoclonal biopanning and sequencing workflow. vi) Unique VLRs are reformatted as rabbit IgG-Fc fusion proteins, secreted from HEK293 cells, and used to immunolabel brain sections to verify binding to relevant BBB antigens in the mouse brain. vii) VLR capability for BBB transport is assessed in vitro with an internalization assay using cultured MBECs. viii) Lead VLR-Fcs coming out of this pipeline are further characterized in various in vitro and in vivo assays.
Figures 3A, 3B, 3C:
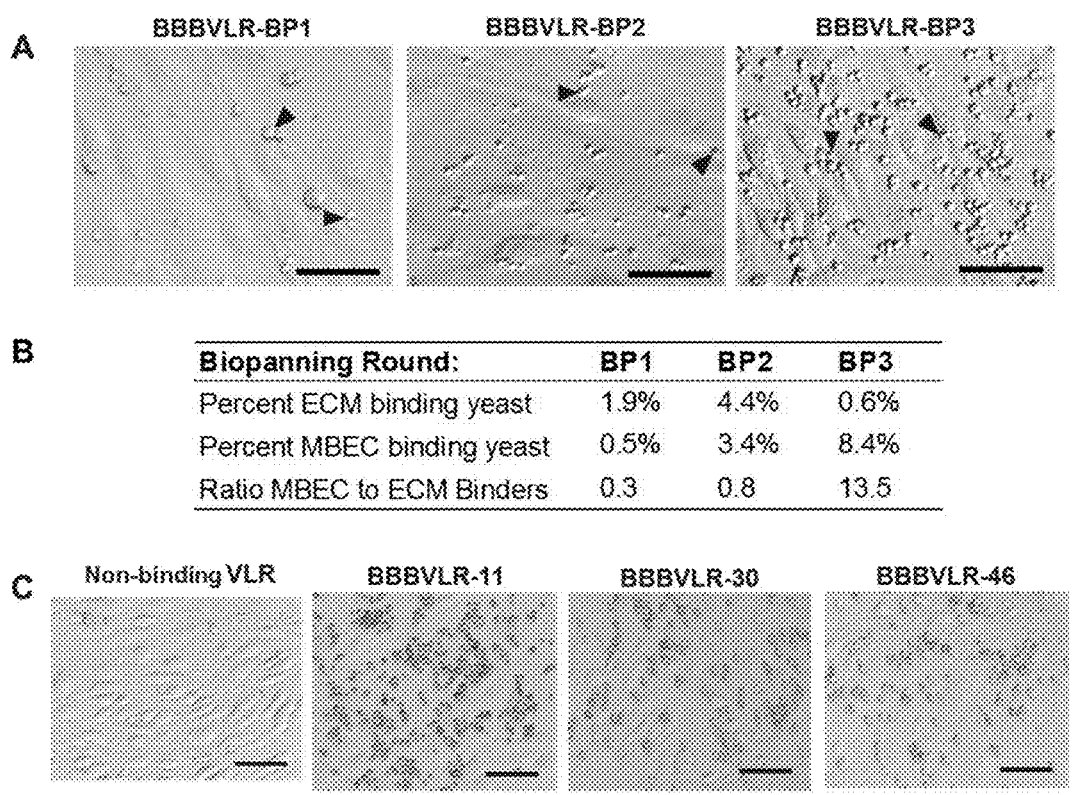
FIGS. 3A-3C. YSD screening of the BBBVLR library. (A) Representative brightfield images of yeast binding to confluent MBEC monolayers at the end of each biopanning round. Yeast are the small round cells and examples are indicated by black arrowheads. (B) Percentage of applied yeast that were recovered by binding to ECM and MBEC during each round of biopanning. (C) After the third round of biopanning, MBEC-binding VLR clones were identified via a 96-well biopanning assay using yeast displaying RBC36 VLR as a non-binding VLR control. Scale bars=50 µm.
Figures 9, 10:
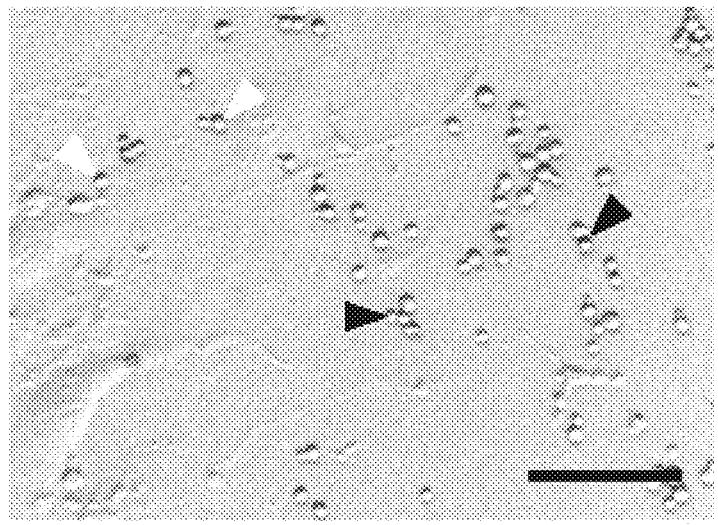
FIG. 9. Table 2 showing glycan binding measurements and glycan descriptions for the top 10 glycans recognized by VLR-Fcs-11, -30, and -46 in the CFG glycan microarray analysis.
FIG. 10. Biopanning experiment on sub-confluent MBECs reveals presence of a substantial population of ECM binding VLR in the library. Yeast (round phase dark cells) are found binding to both MBEC cells (white arrowheads), and ECM (black arrowheads). Scale bar=50 µm.
Figure 11:
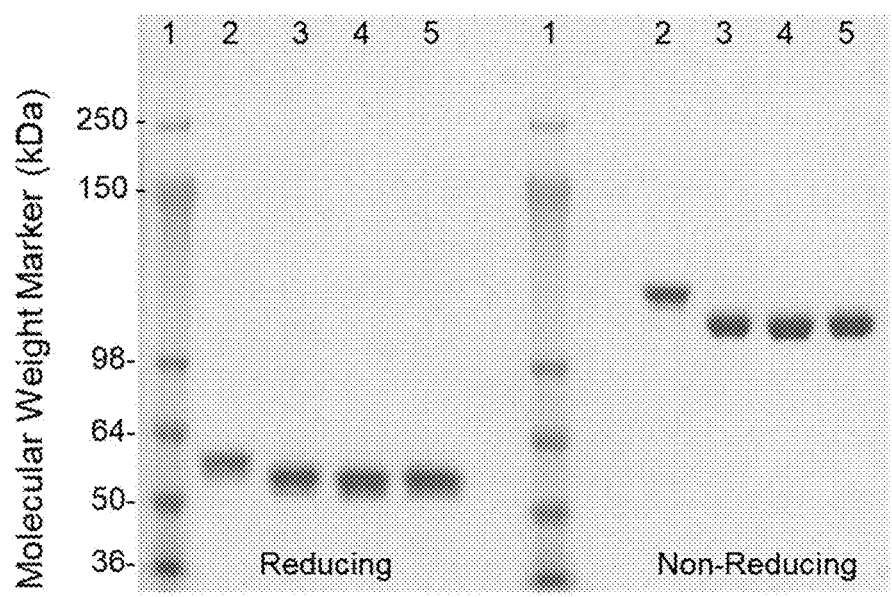
FIG. 11. Coomassie-stained SDS-PAGE gel demonstrating that secreted and purified VLR-Fc having the expected monomeric (Reducing) and dimeric (Non-reducing) molecular weights. Lane 1: molecular weight marker, Lane 2: VLR-Fc-RBC36, Lane 3: VLR-Fc-11, Lane 4: VLR-Fc-30, Lane 5: VLR-Fc-46.

A two-tiered screening strategy was designed and implemented to isolate VLRs from the BBBVLR library that bind to in vivo BBB cell-surface antigens (FIG. 2). The library was initially screened for binding to in vivo antigens via a modified yeast display immunoprecipitation (YDIP) method[39,40] using biotinylated, detergent-solubilized mouse BMPM proteins as the source of antigens for library sorting (FIG. 2ii-iii). Subsequently, YSD biopanning[18] on an immortalized mouse brain endothelial cell (MBEC) line, bEnd.3[41], was carried out to recover VLRs that bind to extracellular epitopes as required for BBB targeting (FIG. 2iv). In more detail, two rounds of YDIP screening with freshly isolated BMPM antigen preparations were carried out, with one round of magnetic activated cell sorting (MACS) followed by one round of fluorescence activated cell sorting (FACS). The resultant library had an approximately 10-fold enrichment in the percentage of BMPM antigen-binding yeast over the starting library (FIG. 2ii-iii). Next, three rounds of YSD biopanning were carried out (FIG. 2iv and FIGS. 3A-3B). Given the nature of the BMPM preparations, there existed VLR clones in the FACS-enriched pool that bound to BBB extracellular matrix (ECM) (FIG. 10). Therefore, each biopanning round included a subtraction panning step to remove ECM binders from the library. Yeast pools were first incubated on decellularized ECM derived from confluent MBEC cultures to subtract ECM binders from the library. Subsequently, non-ECM binding yeast were recovered and immediately applied to intact MBEC monolayers. After washing steps, clones that remained bound to the MBEC cell surface were recovered and regrown for subsequent rounds of biopanning or monoclonal analysis. The biopanning approach enriched for MBEC cell surface binding yeast and de-enriched for ECM binders over three rounds as shown in FIGS. 3A-3B. Initially, there was a significant over-representation of ECM binders compared to MBEC binders as shown by the 0.3 MBEC:ECM binder ratio in the BBBVLR-BP1 pool (FIG. 3B). By the final round of biopanning a very small percentage of the library bound to the ECM plate (0.6%, FIG. 3B) relative to the MBEC binding population (8.4%) representing a nearly 50-fold enrichment in MBEC specific binders over ECM binders. Subsequently, individual clones were tested in a 96-well biopanning assay and 204 out of 240 clones were found to specifically interact with MBEC cells by light microscopy as shown for a select group of clones in FIG. 3C. Sequencing of the VLR genes revealed that 33 of the 204 cell-binding clones represented unique VLR amino-acid sequences.

VLR Clones Bind to In Vivo-Relevant BBB Antigens

Figures 4A, 4B, 4C:
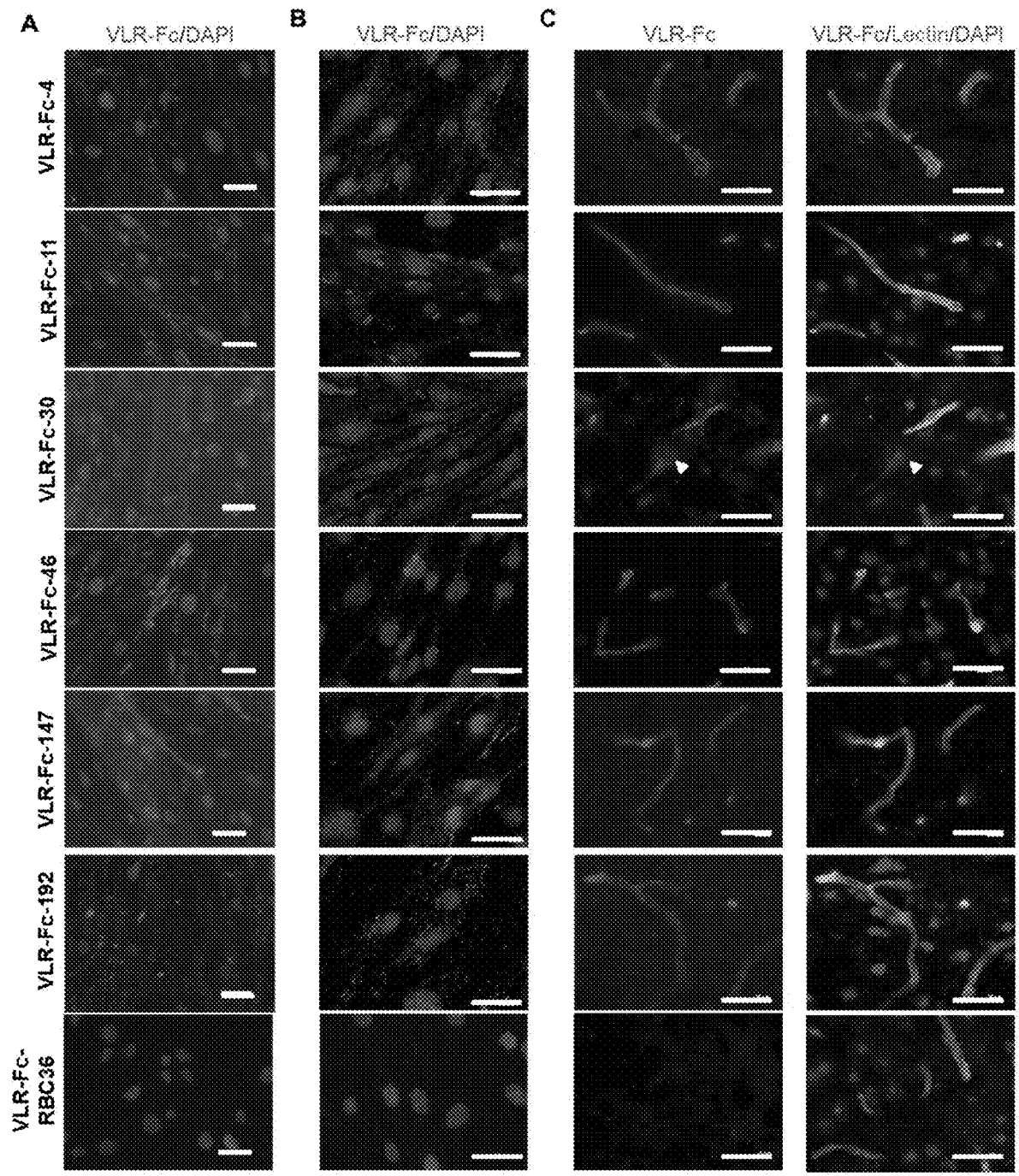
FIGS. 4A-4C. BBB binding profiles for individual VLR clones. VLRs were produced as VLR-Fc fusions and used for immunolabeling (red) of (A) Live MBECs, (B) Fixed and permeabilized MBECs, (C) Mouse brain cryosections. Labeling with IB4-lectin is used to denote the location of microvessels (green). VLR-Fc-RBC36 was used as an isotype control. A white arrowhead highlights binding of VLR-Fc-30 to parenchymal cells. In panels A-C, DAPI (blue) is employed as a nuclear counterstain. Scale bars=25 µm.

To validate that the screening strategy described above yielded MBEC-targeting VLRs that also bound to antigens expressed at the in vivo BBB, the 33 unique VLR clones were analyzed for MBEC and BBB binding. VLRs were produced in transiently transfected HEK293 cells as dimeric, recombinant Fc fusion proteins (VLR-Fc) (FIGS. 2vi and 11). Of the 33 clones, 26 bound to the surface of live MBEC cells (FIG. 4A and Table 1). The remaining 7 clones were either produced at insufficient levels or binding was not detected. Fixed and permeabilized MBEC cells were also labeled with VLR-Fc clones to reveal subcellular localization patterns, of which several VLRs bound differentially to prominent intracellular antigen pools (FIG. 4B), suggestive of internalizing receptors. Next, mouse brain cryosections were labeled with VLR-Fcs to evaluate binding to antigens expressed in vivo (FIG. 4C). Notably, the majority of the MBEC binding VLR clones (19 of 26) were shown to bind antigens in mouse brain. In terms of brain localization, 14 of 19 VLR-Fcs appeared to be selective for the brain vasculature (Table 1 and FIG. 4C, e.g. VLR-Fc-4, 11, 46, 147, and 192), whereas 2 bound both vascular and parenchymal antigens (Table 1 and FIG. 4C, e.g. VLR-Fc-30 white arrowhead). Finally, 3 VLR bound only parenchymal antigens (Table 1, e.g. VLR-Fc-5). In summary, a rather large set of 16 VLRs displaying diverse MBEC surface and intracellular binding patterns as well as brain section binding were identified using this screening strategy.

A Subset of VLRs are Internalized by MBECs In Vitro

Figures 5A, 5B, 5C:
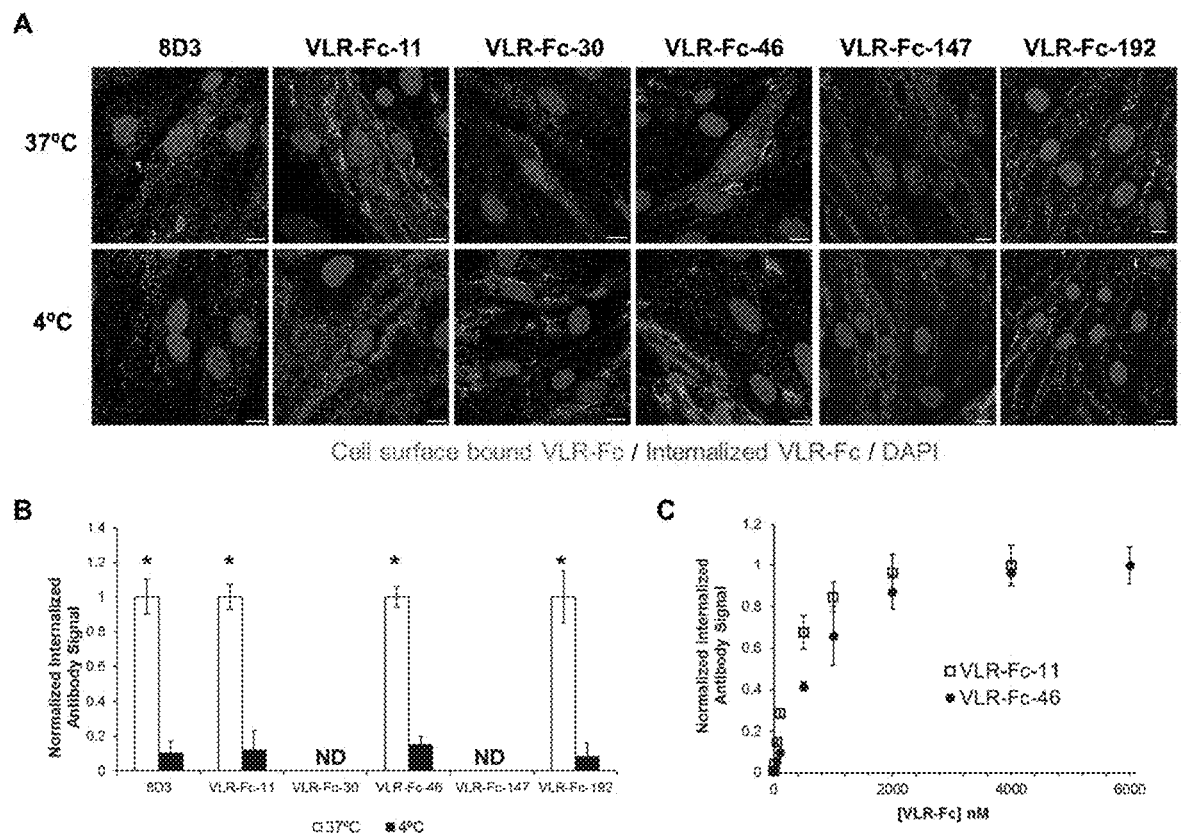
FIGS. 5A-5C. MBEC internalization of VLR-Fcs. (A) MBEC monolayers were incubated with either anti-TfR antibody (8D3) or the indicated VLR-Fc for 30 minutes at 37° C. or 4° C. Surface bound (green) and internalized (red) antibody pools were differentially labeled. Representative confocal Z-slices are shown. DAPI (blue) was employed as a nuclear counterstain. Scale bars=10 µm. (B) Per cell VLR-Fc internalization at 37° C. and 4° C. was quantified using a LiCor scanner and normalized to the 37° C. signal for each clone. ND=Not Detected. (C) Saturability of the internalization pathway was evaluated by titrating VLR-Fc concentrations and quantifying MBEC internalization as in (B). Data in B and C represent the mean±S.D. of 3 independent internalization or saturation experiments. A students t-test on n=3 replicates was used to determine statistical significance *=p<0.05.
Figure 12:
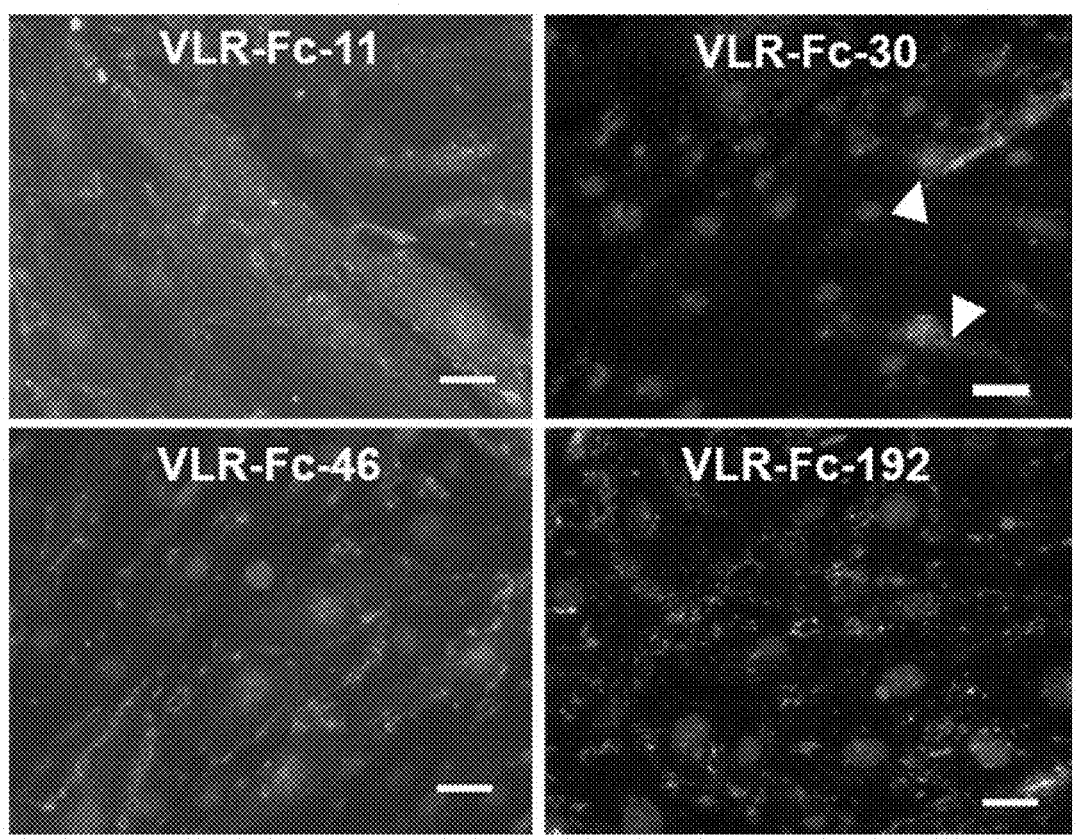
FIG. 12. Fluorescence microscopy analysis of MBEC binding (green) and internalization (red). VLR-Fc-11, 46, and 192 are internalized by the majority of cells. On the other hand, only a small sub-population of MBECs are capable of internalization of VLR-Fc-30 (white arrowheads) while surface binding signal is seen throughout the plate. Red=internalized VLR-Fc, Green=Surface-bound VLR-Fc, Blue=DAPI. Scale bars=25 µm.

Next, in vitro internalization assays were used to further characterize the 16 VLR-Fc clones described above for properties compatible with brain drug delivery applications (FIG. 2vii). Initially, the VLR-Fc were subjected to a temperature-based internalization assay employing a two-color labeling procedure to differentiate cell surface versus internalized VLR-Fc (See Materials and Methods for details). Endocytosis requires membrane fluidity and is inhibited at 4° C.; thus, comparison of internalization of VLR-Fc at 4 or 37° C. provided evidence for a membrane-dependent endocytosis process. Using this approach, 4 out of 16 VLR-Fc tested were shown to internalize via a temperature-dependent process (FIGS. 5A-5B). VLR-Fc-11, VLR-Fc-30, VLR-Fc-46, and VLR-Fc-192 were endocytosed at 37° C. evidenced by intracellular VLR-Fc signal; whereas, VLR-Fc-147 only bound to the cell surface (FIG. 5A). Furthermore, internalization was inhibited at 4° C. for the 4 VLR-Fcs as only surface-bound antibodies were detected (FIG. 5A). In all cases, the internalized VLR-Fc signal was observed in punctate structures within the cytoplasm, indicative of endocytic vesicle trafficking and similar to punctate structures observed for a positive control anti-transferrin receptor antibody, 8D3. While VLR-Fcs-11, -46 and -192 were internalized into nearly all the cells on the plate, VLR-Fc-30 only internalized into a small subset of cells despite exhibiting a cell surface binding signal throughout the plate (FIG. 12). Antibody internalization was also quantified via labeling and detection of intracellular antibody after an acid wash to remove surface bound proteins, and the results agreed with the confocal analysis with roughly 10-fold higher amounts of internalized antibody at 37° C. (FIG. 5B). Another hallmark of receptor-mediated endocytosis is saturability. Given a finite number of cellular receptors and associated trafficking machinery, the amount of ligand internalized will saturate with increasing ligand concentration. Indeed, saturation of the internalization pathway was observed for VLR-Fc-11 and VLR-Fc-46 at antibody concentrations around 204 (FIG. 5C), values similar to that for saturation of the transferrin receptor system[42]. Based on their ability to bind to and traffic within MBECs in a temperature dependent and saturable manner, VLR-Fc-11, -30, and -46 were selected as lead candidates for additional in vitro antigen-binding characterization and in vivo analysis. As described later, the in vivo analysis indicated that VLR-Fc-192 did not target the brain vasculature after systemic administration so it was dropped from further characterization.

TABLE 1

Summary of in vitro and in vivo characterization for select clones from the BBBVLR-BP3 pool

| | Binds bEnd.3 cell surface in YSD format | Binds bEnd.3 cell surface in soluble format | Binds antigen in mouse brain capillaries | Binds antigen in mouse brain parenchyma | Temperature-dependent internalization in bend.3 cells | Binds luminal antigen in vivo |
|---|---|---|---|---|---|---|
| BBBVER-BP3 | 33/204 | 26/33 | 16/26 | 5/26 | 4/16 | 3/4 |
| VLR-Fc-4 | Yes | Yes | Yes | No | No | — |
| VLR-Fc-5 | Yes | Yes | No | Yes | — | — |
| VLR-Fc-11 | Yes | Yes | Yes | No | Yes | Yes |
| VLR-Fc-30 | Yes | Yes | Yes | Yes | Yes | Yes |
| VLR-Fc-46 | Yes | Yes | Yes | No | Yes | Yes |
| VLR-Fc-147 | Yes | Yes | Yes | No | No | — |
| VLR-Fc-192 | Yes | Yes | Yes | No | Yes | No |

Antigen-Binding Characterization Reveals a Role for Glyco-Recognition in Cell Binding Given that VLRs have proven robust in their capability to specifically bind glycan structures[28,29,43], the potential role of glyco-recognition in the binding of VLR-Fc-11, -30, and -46 was investigated. First, the glycan binding specificities for the VLR-Fcs were evaluated using the Consortium for Functional Glycomics (CFG) glycan microarray, which comprises 600 validated mammalian glycans[44], and there was a clear glycan binding signature for each of the VLRs. A comparison of binding profiles for the top 10 glycans recognized by each of the VLR-Fcs is shown along with their respective glycan structures (FIG. 6A and Table 2 (FIG. 9)). VLR-Fcs-11 and -46 exhibited a similar rank ordering and a clear preference for terminal α2-6 linked sialic acid structures having the Neu5Aca2-6Galβ1-4GlcNAc motif with a preference for a β1-3Gal linkage after the GlcNac residue. On the other hand, the binding profile of VLR-Fc-30 appears to be distinct with a Neu5Aca2-6Galβ1-4GlcNAcβ1-3GalNAc motif not recognized by VLR-Fc-11 or -46 yielding the highest binding signal. In addition, VLR-Fc-30 displayed weaker binding (5- to 10-fold decrease in signal intensity versus VLR-Fc-11, Table 2 (FIG. 9)) to the Neu5Aca2-6Galβ1-4GlcNAcβ1-3Gal motif preferred by VLR-Fcs-11 and -46. The similarities in glyco-specificity were supported by an examination of the VLR sequences, which indicated high homology between VLRs 11, 30 and 46 with the only differences located in the LRRNT and LRR1 VLR domains (FIG. 13). These differences in VLR amino acid sequence could also contribute to differences in antigen-binding affinity. Thus, the apparent affinity of VLR-Fc-11, -30, and -46 was determined by direct titration of VLR-Fcs onto MBECs. All three clones bound their cell surface antigens with apparent affinities in the nanomolar range (FIG. 6B). Interestingly, VLR-Fc-11 exhibited an approximately 7-fold higher affinity compared to VLR-Fc-46 (KD=10 nM and 68 nM respectively), which correlated with the signal intensities observed in the glycan microarray analysis where VLR-Fc-11 binding was routinely 2- to 5-fold higher than VLR-Fc-46. Taken together, the glycan array and affinity data suggest that the amino acid differences between VLR-Fc-11 and -46 mainly contribute to differences in affinity. On the other hand, the differences in the VLR-Fc-30 sequence may contribute to altered or broadened specificity preferring a Neu5Aca2-6Galβ1-4GlcNAcβ1-3GalNAc motif over Neu5Aca2-6Galβ1-4GlcNAcβ1-3 Gal motif.

Figure 14:
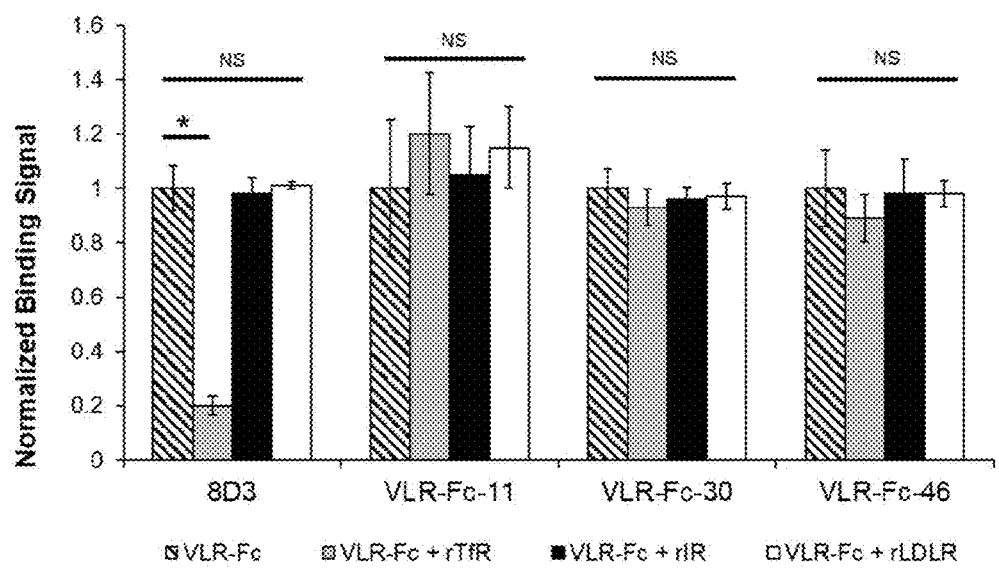
FIG. 14. MBEC binding of VLR-Fcs with or without competition with soluble recombinant receptor ectodomains. VLR-Fcs are compared to the anti-TfR mAb 8D3. The only statistically significant difference is for 8D3 competition with rTFR. The mean±S.D. is plotted. A students t-test on n=3 replicates was used to determine statistical significance *=p<0.05, NS=not significant. rTfR=recombinant transferrin receptor, rIR=recombinant insulin receptor, rLDLR=recombinant low-density lipoprotein receptor.
Figure 15:
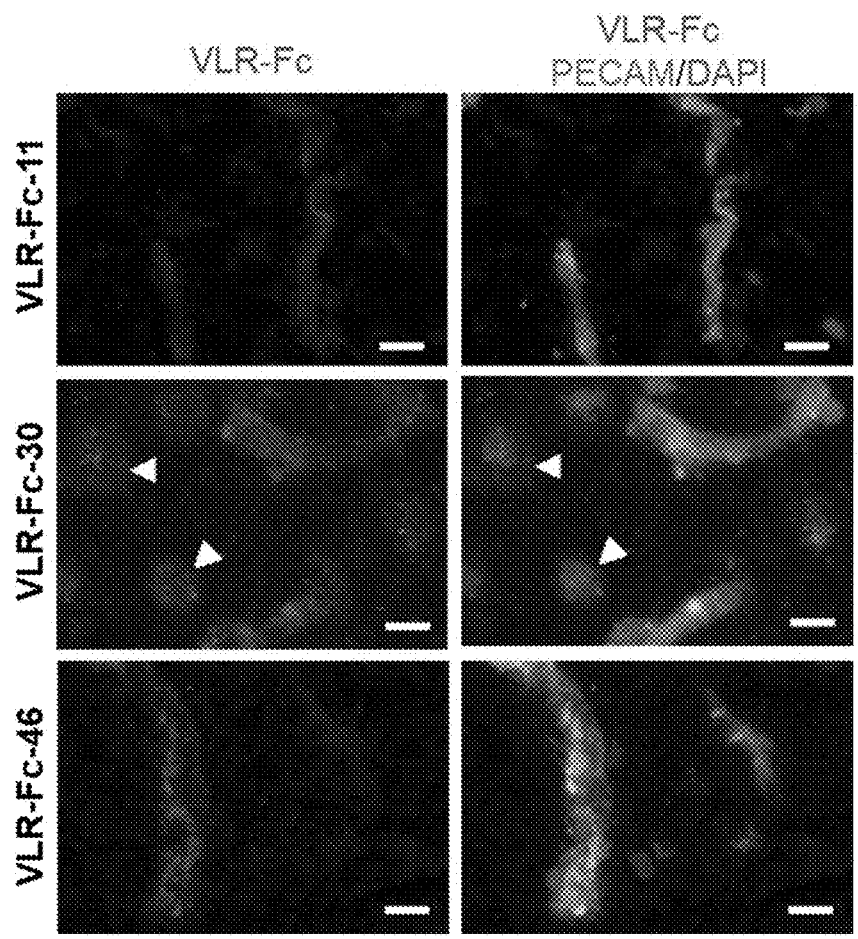
FIG. 15. Immunofluorescence evaluation of VLR-Fc-11, -30, and -46 binding to human cryosections. VLR-Fc (red) and co-localization with PECAM-1 vascular label (green) and DAPI (blue) is shown. VLR-Fc-30 also recognizes antigens in brain parenchymal cells (white arrowheads). Scale bars=15 µm.

To augment the glycan array results and demonstrate that glycan binding is involved in the observed interactions with MBECs, VLR-Fc binding to MBECs was quantified with and without pretreatment of the cells by α2-3,6,8 sialidase which cleaves terminal α2-3, α2-6, or α2-8 linked sialic acid residues from glycans (FIG. 6C). Binding of both VLR-Fc-11 and VLR-Fc-46 to MBECs was significantly decreased after treatment with sialidase. MBEC binding of VLR-Fc-30 upon sialidase treatment was also decreased but to a lesser extent. These results correlated well with the glycoarray results where VLR-Fc-11 and -46 indicated a strong preference for a terminal sialic acid motif whereas the VLR-Fc-30 was less dependent on this motif. Moreover, the decrease in binding for VLR-Fc-11 and -30 upon sialidase treatment was less than that observed for lectins with known sialic acid binding specificity, SNA and MAL II (FIG. 6C), suggesting additional glycan or proteinaceous components to the antigenic epitopes. To rule out VLR-Fc recognition of BBB receptors such as the transferrin receptor (rTfR), Insulin receptor (rIR), and low-density lipoprotein receptor (rLDLR) that have been extensively evaluated for their drug delivery capability, a competitive binding assay was employed. VLR-Fcs were pre-incubated with excess recombinant receptor ectodomains prior to a live MBEC cell surface binding assay. MBEC binding was not affected for any of the VLR-Fcs upon receptor competition (FIG. 14). In contrast and as expected, competition with the rTfR protein reduced the anti-transferrin receptor antibody (8D3) binding signal to ~20% of the non-competition signal, whereas rIR or rLDLR competition did not inhibit 8D3 binding. These results suggest that VLR-Fc-11, -30, and -46 do not bind TfR, IR, or LDLR. Finally, VLR-Fc-11, -30, and -46 also bound the human brain vasculature with VLR-Fc-11 and -46 binding selectively to blood vessels and VLR-Fc-30 binding to blood vessels and parenchymal cells (FIG. 15).

VLRs Target and Traffic the Brain Vasculature after Systemic Administration

Figures 7A, 7B:
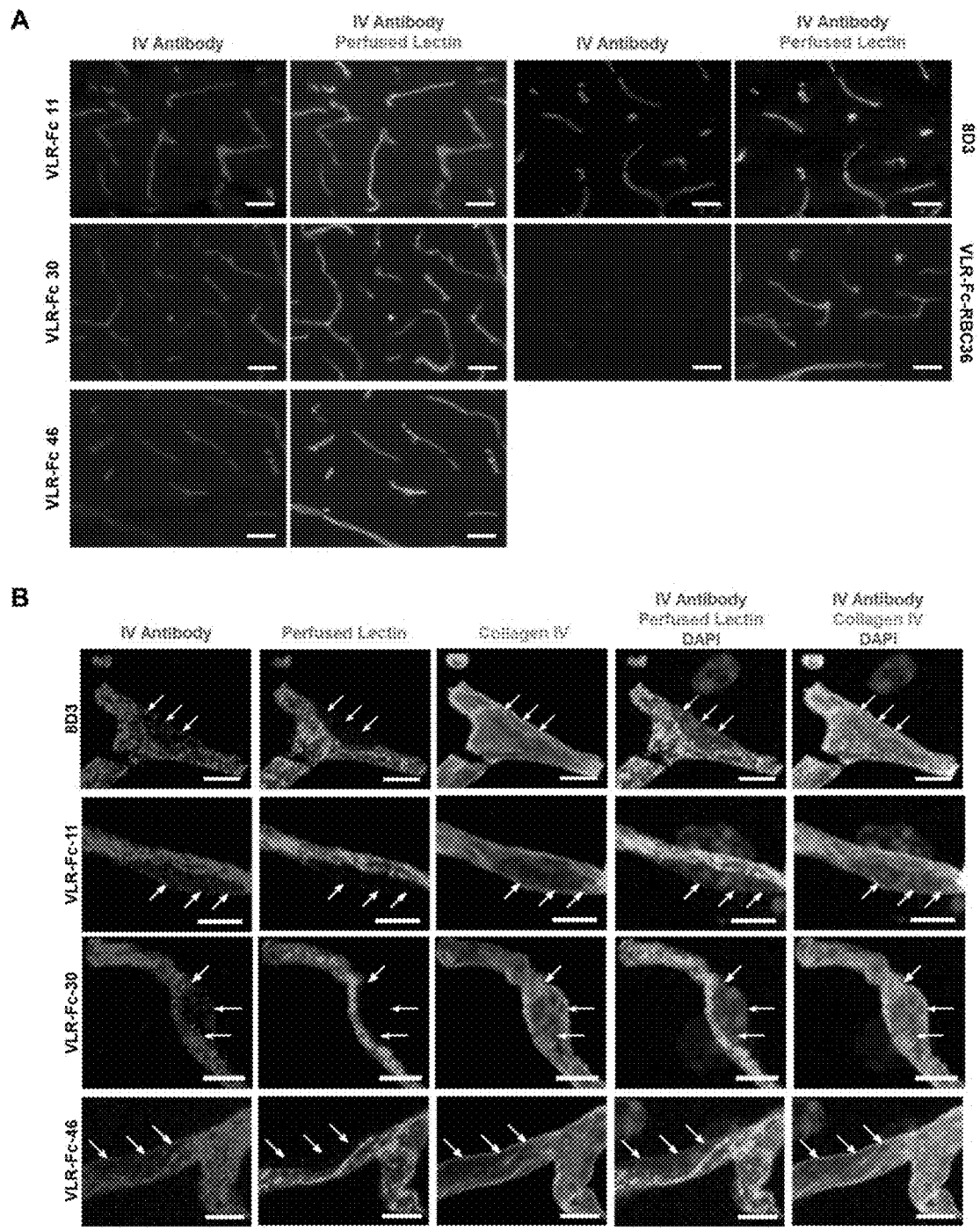
FIGS. 7A-7B. Brain vascular targeting and trafficking of VLR-Fcs after IV injection. Mice were administered 10 mg/kg of the indicated antibody construct (red). After 1 hour of circulation time, mice were perfused with saline containing fluorescently labeled lectin (green) to remove unbound VLR-Fc and label the vascular lumen. (A) Low magnification fluorescence microscopy images from brain cortex. Anti-TfR 8D3 antibody was used as a positive control and VLR-Fc-RBC36 as an isotype control. Scale bars=25 µm. (B) Confocal microscopy analysis showing maximum intensity projections of ~7 µm Z-stacks. Post-labeling with anti-Collagen IV antibody (cyan) was used to delineate the microvessel basement membrane on the abluminal face of the vessels while DAPI (blue) was employed as a nuclear counterstain. VLR-Fc are observed in perinuclear punctate structures and along the abluminal side of the nucleus (white arrows). Representative images from the cortex are shown for n=3 injected animals. Scale bars=5 µm.
Figure 8:
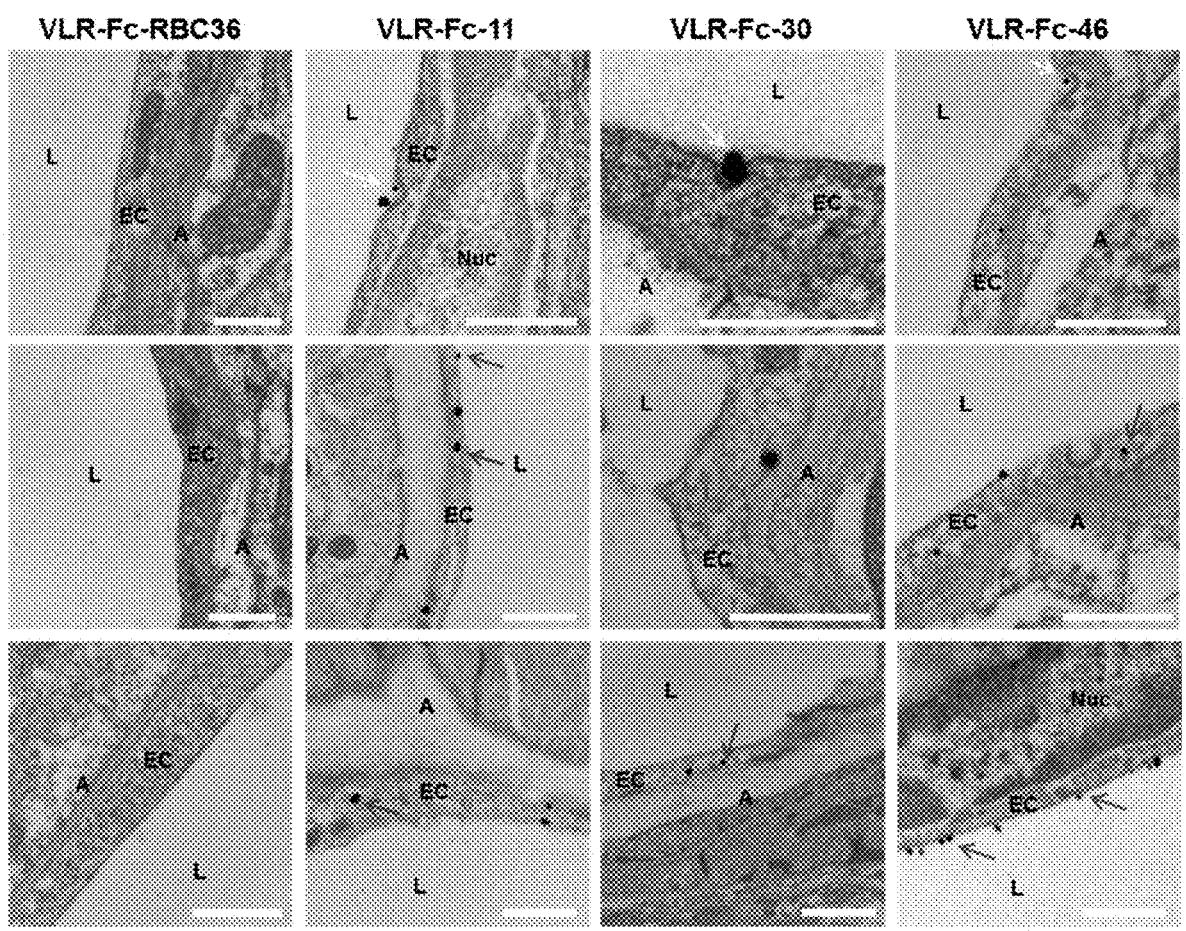
FIG. 8. Immunogold electron microscopy localization of VLR-Fcs in MBECs after IV injection. Anti-rabbit Fc immunogold staining and silver enhancement reveals VLR-Fc localization (black electron dense spheres). VLR-Fc-11, -30, and -46 are observed binding at the luminal face of MBECs (red arrows) and within invaginating endocytic pits (white arrows). VLR-Fc are also observed within MBECs (blue arrows), and at the abluminal membrane (green arrows). VLR-Fc-RBC36 was not observed associated with MBECs. Scale bars=500 nm. EC=brain endothelial cell, L=vessel lumen, Nuc=nucleus, A=abluminal side of brain ECs.

We next sought to determine whether VLR-Fc could target the BBB after systemic administration. To this end, VLR-Fc-11, -30, -46, and -192 were administered intravenously (IV) to mice at a dose of 10 mg/kg and allowed to circulate for 1 hour. The mice were then perfused through the left heart ventricle with saline containing fluorescently labeled lectin to both clear the vasculature of unbound antibody and stain the luminal aspect of microvessels for subsequent imaging analysis. Examination of brain cryosections from VLR-Fc injected animals clearly indicated that all VLR-Fc clones except VLR-Fc-192 (data not shown) bound to the brain vasculature and co-localized with the perfused vascular lectin stain, as did the 8D3 anti-TfR IgG control (FIG. 7A). In contrast, the isotype control VLR-Fc-RBC36 exhibited negligible residual background, despite strong vascular lectin labeling, indicating perfusion was effective in removing any unbound circulating VLR-Fc. Therefore, vascular-localized VLR-Fc signal observed for VLR-Fc-11, -30, and -46 was a result of these VLR-Fc engaging their target antigens on the brain vasculature. At higher magnification, confocal microscopy images indicate a punctate distribution of VLR-Fc co-localized with the luminal vascular lectin stain (FIG. 7B). Given the resolution limits of the confocal techniques used here (~100 nm per pixel) and that the MBECs are very thin (~100 nm), one can only separate the luminal and abluminal signals where the endothelial nuclei spread these two membranes further apart. In these regions, each of the VLR-Fc-11, -30 and -46 could be found in puncta at the abluminal membrane separated from the luminal lectin stain and co-localizing with the basement membrane (FIG. 7B). Similar results were observed with the 8D3, anti-TfR IgG control. These results were suggestive of VLR-Fc trafficking within the MBECs. To further confirm the MBEC trafficking capability of VLR-Fc-11, -30 and -46, immunogold electron microscopy was used to examine the ultrastructural localization of IV injected VLR-Fc at the brain microvasculature. VLR-Fc-11, -30 and -46 were all found localized to the luminal surface, in invaginating endocytic pits, within the cytoplasm of MBECs and at the abluminal membrane (FIG. 8). By contrast, the isotype control VLR-Fc-RBC36 was not observed associated with the brain vasculature. Combined with the confocal microscopy analyses, these data indicate that VLR-Fc-11, -30 and -46 bind to the brain microvasculature and traffic across MBECs after systemic administration.

Discussion

In this work, we have deployed a unique combination of lamprey immunization, yeast display screening and antibody binding characterization techniques to identify a panel of lamprey VLRs that are capable of binding antigens present at the brain microvasculature in vivo, with a subset of these being capable of homing to and trafficking at the BBB after systemic administration. The novel multi-tiered screening strategy developed and applied in this study combined the creation of an immunized library with elements of previously reported YSD screening approaches[18,39,45,46] to rapidly isolate VLRs that target MBECs in vivo. Indeed, since lamprey were immunized with PM fractions prepared from freshly isolated mouse brain microvessels, a robust polyclonal immune response against in vivo-relevant BBB antigens was generated. Porting the immune lamprey VLR repertoire into the YSD platform enabled clonal screening of the immune response to BBB PM antigens. Previous work carried out in our lab has established the YDIP procedure as a platform for discovery and optimization of antibodies against membrane protein targets through screening of combinatorial YSD libraries using detergent solubilized lysates of cultured cells as sources for antigen binding and competition steps[39,47,48].

In this work, we extended the platform by employing detergent-solubilized antigen preparations derived directly from freshly isolated mouse brain microvessels, thereby increasing the in vivo relevance of the antigens presented during VLR library screening. It is well known that expression profiles are altered when BBB cells are cultured out of their natural environment[19,20], therefore, screening with antigens derived from in vitro cultured cells alone often yields a large proportion of antibodies that lack in vivo relevance[18,49]. Consequently, two rounds of YDIP enrichment with in vivo antigen preparations was coupled to downstream biopanning screening to filter the VLRs and identify those that could bind cell surface antigens. YSD biopanning on live MBEC monolayers eliminated the possibility of VLRs interacting with intracellular epitopes of integral membrane proteins or membrane-associated intracellular machinery that were part of the PM preparations used for immunization and YDIP, strongly biasing enrichment towards VLRs targeting cell surface-exposed epitopes. The coupling of YDIP with biopanning was quite successful as non-exhaustive sampling of the biopanning output pool (roughly 200 VLR displaying yeast clones were tested) indicated that around 85% specifically recognized MBEC cell surface antigens, representing 33 unique VLR sequences. Importantly, ~60% (16 out of 26 that could be tested) of those VLRs testing positive in in vitro binding assays also bound their target in mouse brain microvessels (Table 1). This represents a significant improvement over a previous study in which less than 5% of in vitro binding antibodies recognized in vivo antigens when biopanning alone was used to enrich a library for BBB binders[18].

Next, brain microvasculature-binding VLRs were tested for their capacity to target receptor-mediated endocytosis machinery, an important attribute for brain drug delivery applications. Of 16 VLRs shown to bind brain microvessels in tissue sections, 4 of these clones had endocytosis capability. This frequency of cell binders capable of receptor-mediated internalization compares favorably with previous yeast biopanning experiments where approximately 25% of unique cell-surface binders were found to endocytose[18]. Importantly, in vitro internalization behavior was predictive of internalization in vivo as endocytosis and trafficking of IV administered VLR-Fc-11, -30, and -46 was confirmed through confocal and electron microscopy analyses. Although the antigens recognized by the 16 unique microvessel binding VLRs have not yet been fully investigated, differential cell surface binding, intracellular localization and brain section staining patterns, as well as sequence diversity of the VLR clones, suggests that they recognize a varied set of BBB antigens.

One of the main motivations for employing VLRs is that VLRs have proven robust in binding various glycan antigens with desirable affinity and specificity[28,29,31,43,50]. This is especially relevant to BBB-targeting applications as a multitude of known BBB transporters, such as glucose transporter, GLUT 1[34], are glycoproteins, and the BBB glycocalyx has been shown to play important roles at the BBB in health and disease. The BBB glycocalyx is a complex ~100 nm thick structure[51] that has been suggested to serve roles in sieving molecules based on charge and size and therefore contribute to the selective permeability of the BBB[35]. For example, disruption of the BBB glycocalyx by heparinase treatment has been shown to increase BBB permeability and perfusion[36,37]. Moreover, the glycocalyx can play a mechanosensing role that can drive BBB responses to shear stress[52]. Accordingly, heterogeneity in adhesion molecule glycosylation has been suggested as a vascular and disease-specific molecular zip code for inflammatory responses[53]. Despite the established importance of the BBB glycocalyx, the discovery and development of BBB-targeting reagents recognizing BBB glyco-epitopes has been underpursued, perhaps because of the suboptimal glyco-recognition of Ig-based binding scaffolds that have been used in BBB screens[18,54]. However, there exists some evidence that targeting of glycostructures may be an effective epitope space for BBB targeting and delivery. For instance, the FC5 camelid antibody that is currently under development for brain delivery applications[55] was found to be partially dependent on glycan binding[15]. In the current study, not only was the polyclonal lamprey serum shown to bind a whole host of glycans, the three lead VLRs, VLR-Fc-11, VLR-Fc-30 and VLR-Fc-46, all displayed a demonstrable glyco-signature. VLR-Fc-11 and VLR-Fc-46 recognize a Neu5Acα2-6Galβ1-4GlcNAcβ1-3Gal motif whereas VLR-Fc-30 most strongly recognized a Neu5Acα2-6Galβ1-4GlcNAcβ1-3GalNAc motif. Given the sequence similarity in these three VLRs, it is possible that they recognize similar or the same targets. The sialidase data suggest that some binding is retained even after sialic acid removal, suggesting a proteinaceous contribution to the antigenic epitope. Given the novelty of using glycan-binding proteins for BBB targeting, these possibilities warrant further investigation. Interestingly, the glycan motifs recognized by the lead VLRs were not those that were strongly recognized by the polyclonal antiserum, indicating that low abundance VLRs can be enriched and isolated from the polyclonal repertoire using the methods described here.

The unique glyco-recognition attributes and the ability of VLR-Fc-11, -30 and -46 to engage and traffic within mouse BBB endothelium after IV administration indicate that the lead VLRs identified here have potential as novel constructs for applications in targeting therapeutics to the BBB. Significantly for translational considerations, all three VLR demonstrated cross-reactivity to mouse and human antigens. Of course, future work to characterize pharmacokinetics, biodistribution, and the ability to deliver drug payloads to the brain will be necessary to fully assess the translational promise of these novel VLRs. Recently, the engineering of antibody affinity and valency was demonstrated to enhance brain penetration[8-10,12,56,57] and VLR and VLR-based scaffolds have proven amenable to protein engineering techniques aimed at altering binding properties[50,58], so these avenues are available if optimization of brain targeting and trafficking is required. Although VLRs remain underexplored for therapeutic applications, recent studies have demonstrated that Repebodies[59], consensus designed LRR domain proteins based on VLRs, can mediate therapeutic outcomes in animal models motivating further exploration of VLRs as novel alternatives to traditional Ig-based therapeutics[58,60]. Thus, VLR-Fc-11, -30, and -46 are promising lead candidates that may offer unique alternatives for brain drug delivery applications.

Materials and Methods

Cells, Media, and Plasmids

*Saccharomyces cerevisiae* strain EBY100 was used for VLR surface display. The plasmid used for VLR library cloning and display was pCT-ESO61. VLR RBC3628 which specifically recognizes the human blood group type II H trisaccharide (Fucα1,2-Galβ1,4-GlcNAc) was used as an isotype control where indicated. For all yeast surface display experiments, EBY100 yeast were first grown overnight at 30° C. 260 rpm in SD-CAA medium (20 g/L dextrose, 6.7 g/L yeast nitrogen base, 100 mM sodium phosphate buffer pH 6.0, 5.0 g/L bacto-casamino acids without tryptophan and uracil). The day before an experiment all yeast cultures were re-set to an OD600 of ~0.4 and grown for 3-4 hours until reaching an OD600 of 1. Then, surface display was induced via switching to SG-CAA induction medium (same recipe as SD-CAA except galactose is used instead of glucose) and cultures were grown at 20° C., 260 rpm for 16-18 hours. HEK293F cells were purchased from ATCC (CRL-1573) and maintained in Freestyle F17 Medium (Thermo Fisher) at 37° C., 8% $CO_2$, and 135 rpm in a humidified incubator. The plasmid used for production of soluble VLR-Fc was pIRES-VLR-Fc. bEnd.3 cells at passage 22 were purchased from ATCC (CRL-2299) and maintained in complete growth medium (DMEM supplemented with 4 mM L-glutamine, 4500 mg/L glucose, 1 mM sodium pyruvate, 1500 mg/L sodium bicarbonate, and 10% fetal bovine serum) at 37° C., and 5% $CO_2$ in a humidified incubator up to passage 30.

Animals

Male C57BL/6 mice (*Mus musculus*) at 6 to 7 weeks of age were purchased from Envigo and used in terminal experiments. All mouse experiments were approved by the UW-Madison Institutional Animal Care and Use Committee (IACUC). Sea lamprey larvae (*Petromyzon marinus*) captured from the wild by commercial fishermen (Lamprey Services, Ludington, MI) were maintained in sand-lined, aerated aquariums at 16-20° C. and fed brewer's yeast. All lamprey experiments were approved by the Emory University IACUC.

Capillary Isolation, Plasma Membrane Fractionation, and Quality Analysis

Brains were removed from 6-7 week old male C57BL/6 mice (~20 g) and stored in DMEM on ice. Microvessels were isolated and endothelial plasma membranes fractionated essentially as previously described[38]. Briefly, the cerebellum and white matter were dissected away and brains were rolled on Whatman 3 MM chromatography blotting paper to remove the meninges. Up to 15 brains were homogenized in 20 mL DMEM+0.2% BSA in a dounce homogenizer, and the homogenate was passed over a 150 μm nylon mesh to remove large debris. The homogenate was mixed with an equal volume of 40% dextran solution and centrifuged at 5,000×g for 15 minutes at 4° C. The supernatant was discarded, and the crude microvessel pellet was resuspended in DMEM+0.2% BSA. Microvessels were then recovered on 41 μm nylon mesh filters and washed twice with PBS. To prepare biotinylated plasma membrane proteins for yeast display library screening, microvessel membrane proteins were biotinylated prior to plasma membrane fractionation via incubation with 5 mM sulfo-NHS-LC-biotin (Thermo Fisher), which is membrane impermeable, for up to 2 hours at 4° C. Unreacted biotinylation reagent was quenched by addition of glycine to a final concentration of 100 mM and 10 minutes incubation on ice. Biotinylated microvessels were washed twice with PBS+100 mM glycine to ensure complete quenching and removal of unreacted biotinylation reagent. Plasma membranes prepared for lamprey immunization were not biotinylated. Endothelial plasma membranes were fractionated from the purified microvessels via a two-step hypotonic lysis: (1) distilled water at 4° C. for 2 hours and (2) 10 mM Tris-HCl pH 7.4 at 4° C. for 30 minutes. This was followed by sonication in 50 mM Tris-HCl pH 7.4 and centrifugation at 25,000×g. This resulted in a supernatant containing dispersed plasma membrane fragments and a pellet containing the capillary basement membranes. The supernatant fraction is referred to as brain microvessel plasma membranes (BMPM) and used for lamprey immunization and yeast display screening. All buffers contained protease inhibitor cocktail (PIC, Roche, 11836170001) and 2 mM EDTA. Total protein concentration in all fractions was quantified using a BCA assay kit (Thermo Fisher) following the manufacturer's instructions. This isolation procedure yielded 255±35m of BMPM proteins from 15 mice. For quality analysis of the plasma membrane fractionation via western blotting, 10 μg of total protein from each fraction was separated via SDS-PAGE and transferred to nitrocellulose. Western blotting for brain capillary endothelial membrane marker Glut1 was carried out using a 1:1000 diluted rabbit anti-Glut1 (Thermo Fisher, PA1-46152). Western blotting for astrocyte endfoot marker GFAP (astrocyte endfeet are tightly associated with the basement membrane) was achieved with a 1:1000 dilution of mouse-anti-GFAP (BD Biosciences, 556329). Further quality analysis was achieved via γ-glutamyl-transpeptidase (GGT) activity assay as previously described[62].

Lamprey Immunizations

Sea lamprey larvae were sedated with 0.1 g/L tricainemethanesulfonate (Tricaine-S; Western Chemical, Inc.), then injected into the coelomic cavity with 50 μg of BMPMs in 30 μl of PBS. Three lampreys were immunized a total of three times at two week intervals and blood was collected two weeks after the final immunization from lampreys euthanized with 1 g/L Tricaine-S. Approximately 200 μl of blood was collected in 200 μl of PBS containing 30 mM EDTA as an anticoagulant. Blood plasma and leukocytes were separated from erythrocytes by layering the blood on top of 55% Percoll and centrifugation at 400×g for 5 minutes. Erythrocytes pelleted to the bottom of the tube, while leukocytes collected at the 55% Percoll interface and plasma remained above the interface. Buffer was added to the plasma samples to a final concentration of 20 mM MOPS/0.025% sodium azide pH 7.5 and stored at 4° C. Leukocytes were stored in RNAlater™ at −80° C. until needed for VLRB cDNA library cloning.

VLR Library Cloning

RNA isolated from total leukocytes using the Qiagen RNeasy™ kit was reverse transcribed into cDNA using SuperScript III reverse transcriptase (Invitrogen) and oligo-dT priming. VLRB transcripts were amplified from the leukocyte cDNA by nested PCR using KOD high fidelity DNA polymerase (Novagen). The first round of PCR utilized primers to the 5' and 3' untranslated region, (5'-CTCCGC- TACTCGGCCTGCA; SEQ ID NO:26) and (5'-CCGC-CATCCCCGACCTTTG; SEQ ID NO:27), respectively.

The second round of PCR used primers that amplified only the VLRB antigen-binding domain from the LRRNT (5'-GCATGTCCCTCGCAGTG; SEQ ID NO:28) to the LRRCT (5'-CGTGGTCGTAGCAACGTAG; SEQ ID NO:29), and 50 bp of sequence homology to the yeast surface display vector was added to each primer for cloning by in vivo homologous recombination in transfected yeast cells. PCR products were excised from 1% agarose gels, purified using the Promega Wizard™ gel extraction kit and eluted in water. The pCT-ESO-BDNF yeast surface expression plasmid was digested with NheI, BamHI and NcoI to linearize the vector and remove the BDNF insert. Prior to transformation with the VLR library, yeast were grown to log-phase in SD-CAA medium 30° C. until the culture density reached ~1 OD600. The yeast cells were harvested by centrifugation at 1,000×g, washed in Milli-Q water, and then incubated in 10 mM Tris/10 mM DTT/100 mM LiOAC, pH 7.6 at 225 rpm 30° C. for 20 min. After the incubation, the yeast cells were washed in Milli-Q water and resuspended in 1 M sorbitol at 1×10$^9$ cells/ml. 200 µl of yeast cells were mixed with 1 µg of digested vector and 2 µg of the purified VLRB PCR product and added to a 0.2 cm electroporation cuvette on ice. The yeast were electroporated at 2.5 kV (12.5 kV/cm) using a Biorad Micropulser. After electroporation, the yeast cells were incubated in a 1:1 mixture of 1 M sorbitol and YPD media (Fisher Scientific) at 30° C. for 1 hr, then transferred to SD-CAA media. A small aliquot of the electroporated yeast cells was serially diluted in SD-CAA media and plated on SD-CAA agar plates to calculate the total number of transformants. Three electroporated samples were combined resulting in a library of 7.5×10$^6$ VLR clones. Aliquots of the yeast library were stored at −80° C. in 15% glycerol.

YSD Library Screening with Detergent Solubilized BMPM Proteins

VLR display libraries and control yeast displaying VLR-RBC36 were grown and induced as described above for each round of YSD screening. Two rounds of screening via the YDIP method were carried out as previously described[40] with modifications. In each round, ~250 µg freshly isolated biotinylated BMPM proteins were solubilized in a final volume of 1 mL PBS containing protease inhibitor cocktail (Roche), 2 mM EDTA, 1 mM Biotin, 1% w/v BSA, and 1% v/v TritonX-100. To ensure complete solubilization of membrane proteins the mixture was incubated for 15 minutes at 4° C. and insoluble debris was removed via centrifugation. The first round of screening was carried out using a magnetic activated cell sorting (MACS) protocol[64] to recover VLR binding to biotinylated BMPM antigens. Briefly, 2.1×10$^8$ yeast, 30-fold excess of starting library size, were incubated with 1 mL detergent solubilized BMPMs for two hours at 4° C. with rotation. Yeast were then washed twice with 1 mL ice cold PBS+1% TX-100+1% BSA (PBSTXA) and once with ice cold PBS+1% BSA (PBSA). Washed yeast were resuspended in 0.5 mL ice cold PBSA, then 50 µL streptavidin microbeads (Miltenyi, 130-048-102) were added, and the mixture was incubated at 4° C. with rotation for 30 minutes. Microbead-bound yeast were washed once with 1 mL PBSA and resuspended in 0.5 mL PBSA. The 0.5 mL microbead-yeast suspension was applied to an LS column (Miltenyi, 130-042-401) placed within a Midi-MACS separator magnet (Miltenyi, 130-042-302). The column was washed twice with 3 mL ice cold PBSA, removed from the magnet, and yeast were eluted via plunging with 3 mL SD-CAA medium. Dilutions of the eluate were plated to count the number of yeast recovered and the remaining yeast regrown for subsequent screening. In the second round of screening fluorescence activated cell sorting (FACS) was employed to further enrich for BMPM binders. 5×10$^7$ yeast were incubated with 0.5 mL detergent solubilized BMPMs for two hours at 4° C. with rotation. Full length VLR expression was detected via labeling with rabbit-anti-cmyc epitope (Thermo Fisher, PA1-981) followed by a goat anti-rabbit IgG-Alexa488 secondary (Thermo Fisher, A-11008). Binding to biotinylated BMPM antigens was detected by labeling with a mouse-anti-biotin (Labvison, BTN.4) followed by a goat anti-mouse IgG-allophycocyanin (Thermo Fisher, A-865). 3×10$^7$ labeled yeast were sorted on a Becton Dickson SORP FACSAriaII (University of Wisconsin Carbone Cancer Center) to recover yeast double positive for VLR expression and BMPM antigen binding, and the sorted yeast were expanded in SD-CAA.

YSD Library Biopanning

A two-step biopanning method was developed and applied to remove extracellular matrix (ECM) binding VLRs from the FACS-sorted library while enriching for VLRs that bind to extracellular epitopes using the bEnd.3 MBEC line. For each round, two substrates were used for biopanning. One 6-well plate containing decellularized ECM from bEnd.3 culture was prepared by growing cells to ~90% confluence then switching the cells to media supplemented with 5% ~500 kDa dextran sulfate (DxS, Acros Organics, 433240050) to promote robust ECM deposition[65]. After 4-6 days in DxS, cells were washed with PBS and plates were decellularized via a non-enzymatic protocol to leave behind intact ECM[66,67]. This plate was used in the ECM subtraction step. A second plate containing bEnd.3 cells grown to confluence under normal culture conditions was also prepared and used for the MBEC binding step. Prior to incubation with yeast, both ECM and MBEC plates were blocked for 30 minutes with PBSA at 4° C. ECM subtraction was initiated by addition of induced yeast libraries or control yeast expressing VLR RBC36 suspended in PBSA into wells of the ECM plate at a density of 0.85×10$^6$ yeast/cm$^2$. The plate was incubated with gentle rocking for 2 hours at 4° C. Non-binding yeast were recovered from the ECM subtracted plate after 2 washes with ice cold PBSA and immediately applied to the MBEC binding plate for 2 hours at 4° C. with gentle rocking. Non-binding yeast were removed by 3 washes with ice cold PBSA, and MBEC binding yeast were then recovered by scraping the cells into SD-CAA medium. Dilutions of the MBEC binding cells were plated to count the number of yeast recovered and the remainder were expanded for subsequent rounds of biopanning or individual clone analysis.

VLR-Fc Subcloning, Production, and Purification

VLR identified from the YSD screen were cloned into an expression vector, pIRES-VLR-Fc constructed from pIRE-Spuro2 (Clontech, 6937-1), by cloning rabbit IgG-Fc into the AgeI and BamHI sites. The expression vector included the VLRB signal peptide upstream of the multiple cloning site (MCS) to promote secretion of VLR into the culture media and the rabbit IgG-Fc downstream of the MCS to enable simple purification of VLR-Fc fusion proteins via ProteinA/G chromatography. VLR sequences were amplified via PCR with the following primers: VLRB-NT-NheI-F (5'-GAGAGCTAGCTGTCCCTCGCAGTGTTCG; SEQ ID NO:30) and VLRB-CT-AgeI-R (5'-GAGAACCGGTCGTGGTCGTAGCAACGTAG; SEQ ID NO:31). PCR products were digested with NheI and AgeI and ligated into the pIRES-VLR-Fc vector.

Soluble VLR-Fc fusion proteins were expressed by transient transfection of HEK293F suspension cultures. 80 µg pIRES-VLR-Fc plasmid DNA was mixed with 160 PEI (Polysciences, 23966) in 3 mL OptiPRO SFM (Thermo Fisher, 12309019) for 15 minutes and then applied dropwise to 80 mL HEK293F cultures. Transfected cultures were then incubated for 5-7 days at 37° C., 8% $CO_2$, 135 rpm in a humidified incubator and the supernatant containing secreted VLR-Fc was recovered via centrifugation and filtration. VLR-Fcs were purified from the cleared supernatant via gravity-driven chromatography over a packed bed of 100 uL Protein A/G Plus Agarose beads (Thermo Fisher, PI20423). After washing, three 200 µl fractions were eluted from the column with 100 mM Citric Acid pH 3 and neutralized with 1 M Tris-base pH 9, which typically yielded ~0.5 mg purified proteins from an 80 mL transfected culture. Purified proteins were stored for up to 2 months at 4° C.

Immunolabeling of Tissue and Cells with VLR-Fc

14 µm coronal brain cryosections from male C57BL/6 mice were washed in PBS and then blocked and permeabilized with immunolabeling buffer (PBS+10% goat serum+1% BSA+0.05% saponin) for 30 minutes at room temperature. Next, purified VLR-Fcs at 5 µg/mL in labeling buffer were incubated on the brain slices for 1-2 hours at room temperature. After washing, brain sections were incubated with goat anti-rabbit IgG-Alexa555 secondary to detect VLR-Fc binding and Isolectin B4-Alexa488 (Thermo Fisher, 121411) as a brain microvessel marker for 1 hour on ice. After washing, sections were post-fixed with 4% PFA, nuclei labeled with DAPI, and mounted in ProLong Gold antifade reagent (Thermo Fisher, P10144). Cell surface binding on live bEnd.3 cells was carried out by incubation with 5 µg/mL purified VLR-Fc proteins in PBS+10% Goat serum+1% BSA (PBSGA) for 1 hour at 4° C. After washing VLR-Fc binding was detected by staining with goat anti-rabbit IgG-Alexa555 in PBSGA for 30 minutes on ice. After washing, cells were post-fixed with 4% PFA, nuclei labeled with DAPI, and mounted in ProLong Gold antifade reagent. For whole cell labeling, cells were prefixed with 2% PFA, then blocked and permeabilized in immunolabeling buffer prior to incubation with VLR-Fc and detection reagents as described for cell surface binding. In all cases, images were obtained with a Zeiss Imager Z2 Microscope equipped with an AxioCam MRm using 10× or 63× objectives. Human brain samples were obtained with approval from the University of Wisconsin-Madison Institutional Review Board, sectioned and labeled via the methods described above for mouse sections.

Cell-Based Assays

Internalization assays. bEnd.3 cells analyzed by immunofluorescence microscopy were grown to confluence on glass coverslips. bEnd.3 cells used in quantitative internalization assays were grown to confluence in 96-well flat-bottomed plates (Corning, 353948). Cells were serum starved for 1 hour at 37° C. in serum-free complete growth media. Subsequently, purified VLR-Fc diluted in serum-free complete growth media were applied to the cells. Conditions were varied depending on the experiment. For temperature dependent internalization assays one group of cells was incubated with 10 µg/mL VLR-Fc at 37° C. and one group with the same concentration of VLR-Fc at 4° C. Both groups were incubated for 30 minutes prior to subsequent labeling steps. For saturation experiments, all cells were incubated for 20 minutes at 37° C. with varying concentrations of VLR-Fc up to 4 µM. Samples for microscopy analysis were processed as follows. After the VLR-Fc incubation period, bEnd.3 cells were washed 3× with ice cold PBS and incubated with goat anti-rabbit IgG-Alexa488 in PBSGA for 30 minutes on ice to label cell surface bound VLR-Fc. Following washes, cells were fixed in 2% PFA for 10 minutes at room temperature, and then were blocked and permeabilized in immunolabeling buffer for 30 minutes on ice. To differentially label internalized VLR-Fc, the fixed and permeabilized cells were incubated with goat anti-rabbit IgG-Alexa555 in immunolabeling buffer for 30 minutes on ice. After washing, cells were post-fixed with 4% PFA, nuclei labeled with DAPI, and mounted in ProLong Gold Antifade Reagent. Samples were analyzed via widefield and/or confocal microscopy as described below. Samples for quantitative analysis of internalized VLR-Fc were processed as follows. bEnd.3 cells were first acid washed by 5 changes of ice-cold 0.9% w/v saline, pH 2.5 for a total of 25 minutes to remove cell-surface bound VLR-Fc. This stripping procedure routinely resulted in the removal of ~90% of the cell-surface bound VLR-Fc signal. Cells were then fixed with 2% PFA and blocked and permeabilized in Odyssey Blocking Buffer (Li-Cor, 927-40000)+0.1% TX-100 for 30 minutes at room temperature. Internalized VLR-Fc were detected by IRdye800CW goat anti-rabbit IgG (Li-Cor, 925-32211) and cell number in each well estimated with CellTag 700 (Li-Cor, 926-041090) both diluted in Odyssey Blocking Buffer and incubated with cells for 1 hour at room temperature. After extensive washes with ice cold PBS+0.1% Tween-20 and drying of the plate, signal in each well was measured with a Li-Cor Odyssey Imager with a focus offset of 3 mm and resolution of 169 µm. VLR-Fc signal in each well was normalized to a per cell basis by dividing by the CellTag 700 signal.

Equilibrium Binding Measurements. bEnd.3 cells were grown to confluence in 96-well flat-bottomed plates, washed 3× in PBS, and fixed with 2% PFA for 10 minutes at room temperature. Fixed cells were blocked and permeabilized as described above. Equilibrium affinity titration measurements were achieved via incubation of the cells with purified VLR-Fc diluted to a range of concentrations from 800 pM to 4 µM at room temperature for 2 hours. After extensive washing with ice cold PBS+0.1% Tween-20, cells were labeled for detection with the IRDye reagents and analyzed as described above. Fraction of cellular antigen sites bound by VLR-Fc was quantified using background subtracted per-cell binding signal and the data were fit to a bimolecular equilibrium binding model to determine the dissociation constant (KD).

Competition assay. 2 µM recombinant receptor ectodomain proteins, rIR (R&D systems, 7544-MR), rLDLR (R&D systems, 2255-LD), and rTfR (Sino Biologics, 50741-M07H) were incubated with 200 nM VLR-Fc proteins in serum-free complete growth media for 30 minutes and then applied to serum-starved bEnd.3 cells in 96-well plates to allow for VLR-Fc binding to cell surface receptors. Plates were incubated at 4° C. for 2 hours. After extensive washing with ice cold PBS cells were fixed with 2% PFA, permeabilized, labeled with IRDye reagents, and analyzed as described above.

Sialidase pre-treatment assay. bEND.3 cells were grown to confluence in 96-well flat-bottom plate. Cells were fixed in 4% PFA for 20 minutes at room temperature, washed in PBS, then blocked in Odyssey Blocking Buffer for 90 minutes at room temperature. In some cases, cells were pre-incubated with sialidase (P0720L, New England Biolabs) for 30 mins at 37° C. to cleave glycans containing terminal sialic acid motifs. VLR-Fc (15 µg/mL) or biotinylated lectin (15 µg/mL) were added to the cells and incubated for 2 hours at 4° C. to allow for binding. After washing with ice cold PBS+0.1% Tween-20, VLR-Fc were labeled with IRdye800CW goat anti-rabbit IgG (925-32211, Li-Cor), lectin with IRdye800CW Streptavidin (925-32230, Li-Cor), and cell number with CellTag 700 (926-041090, Li-Cor). The plate was washed with ice cold PBS+0.1% Tween-20 and dried. Signal was detected with a Li-Cor Odyssey Imager with a focus offset of 3 mm and resolution of 169 µm. Binding signal in each well was normalized to cell number using the CellTag700 signal.

In Vivo VLR-Fc Brain Targeting Experiments

Male C57BL/6 mice (~20 g) were injected intravenously with 10 mg/kg VLR-Fc or positive control anti-TfR (8D3, AbDSerotec) in PBS. After 1 hour of antibody circulation, mice were deeply anesthetized, the thoracic cavity was opened, and transcardial perfusion was initiated via insertion of a catheter into the left ventricle and clipping of the right atrium. Ice cold wash buffer containing Earle's balanced salts, 20 mM HEPES, 1 g/L glucose, 10 g/L BSA, and 5 mg/L DyLight488 conjugated tomato lectin (LEL, Vector Laboratories, DL-1174) was perfused at 5 mL/min for 5 minutes with a peristaltic pump to wash away unbound antibodies and label the vessel lumen with lectin. Then perfusion fixation with room temperature 4% PFA was carried out at the same flowrate for 10 minutes. Upon completion of perfusion the brain was dissected and stored in ice cold PBS. For immunofluorescence analysis, brains were cryopreserved in OCT (optimal cutting temperature compound, Fisher Scientific) and stored at −80° C. prior to sectioning. For electron microscopic analysis tissue was immediately cut into 150 µm thick coronal sections on a vibratome and stored in fixative containing 4% PFA and 0.01% glutaraldehyde overnight at 4° C. with gentle agitation.

Sample Preparation and Immunofluorescence Microscopy

30 µm thick coronal brain sections were cut on a cryostat, and adhered to positively charged glass slides. Sections were washed with PBS to remove embedding compound and fixed with 2% PFA. Tissue was blocked and permeabilized in immunolabeling buffer for 30 minutes at room temperature. To visualize VLR-Fc in the brain sections, tissue was incubated overnight with goat anti-rabbit IgG Alexa555 in immunolabeling buffer at 4° C. In some cases, a goat anti-collagen IV antibody (AB769, EMD Millipore) diluted in donkey immunolabeling buffer (goat serum replaced by donkey serum) was incubated on the sections for 2 hours at 4° C. Subsequently, sections were incubated with donkey anti-rabbit IgG-Alexa555 conjugate and donkey anti-goat IgG-Alexa647 conjugate in donkey immunolabeling buffer overnight at 4° C. In all cases, sections were post-fixed in 4% PFA, nuclei labeled with DAPI, and mounted in ProLong Gold antifade reagent. Low magnification widefield images were obtained on a Zeiss Imager Z2 Microscope equipped with an AxioCam MRm using the 10× objective. Confocal imaging was performed on a NikonAR1 microscope using a Plan Apo X, 60× oil objective with 1.4 numerical aperture and optical z-sections were obtained with a step size of 250 nm. Z-stacks were typically taken through a thickness of 5-10 µm. Images were 12-bit, 1024×1024 pixels, with a pixel size of 100, 110, or 120 nm. Maximum intensity projections of the Z-stacks were created using the Maximum Intensity Projection tool in NIS Elements (Nikon Metrology).

Sample Preparation and Electron Microscopy

Immunogold labeling of 150 µm vibratome sections from mice injected with VLR-Fc was carried out with reagents purchased from Electron Microscopy Sciences (EMS) essentially following the manufacturers protocols. After aldehyde quenching with 0.1% $NaBH_4$, sections were permeabilized via incubation with 0.1% TritonX-100 in PBS for 30 minutes, and then blocked with AURION Goat Serum Blocking Solution (EMS, 25596) for 1-2 hours at room temperature. Subsequently, sections were incubated with goat anti-rabbit IgG-Ultrasmall Gold conjugate (EMS, 25100) diluted in PBS+0.2% AURION BSA-c (EMS, 25557) overnight at 4° C. with gentle agitation. Following extensive washing sections were fixed in 2% glutaraldehyde for 30 minutes. Silver enhancement was carried out using the R-Gent silver enhancement kit (EMS, 25520) following the manufacturer's instructions to increase the size of the ultrasmall gold particles. Sections were post fixed in 0.5% Osmium Tetroxide, 1% potassium ferrocyanide in 0.1 M sodium phosphate buffer for 1 hour at room temperature. After rinsing, sections were dehydrated through a graded ethanol series (35%, 50%, 70%, 80%, 90% for 5 minutes each, 95% for 10 minutes, and 100% for 30 minutes). The sections were then infiltrated via incubations with increasing concentrations of PolyBed812 in propylene oxide. After infiltration, sections were embedded in 100% PolyBed812 overnight at 60° C. in a drying oven. 100 nm ultrathin sections were cut using a Leica EM UC6 ultramicrotome and captured on Pioloform carbon-coated 1×2 Cu slot grids (EMS) and contrasted with Reynolds lead citrate and uranyl acetate. The sections were examined on a Phillips CM120 transmission electron microscope and images captured with a MegaView III digital camera (Olympus-SIS).

REFERENCES

1. Abbott, N. J., Patabendige, A. A. K., Dolman, D. E. M., Yusof, S. R. & Begley, D. J. Structure and function of the blood-brain barrier. Neurobiol. Dis. 37, 13-25 (2010).
2. Pardridge, W. M. The blood-brain barrier: bottleneck in brain drug development. NeuroRx 2, 3-14 (2005).
3. Daneman, R. The blood-brain barrier in health and disease. Ann. Neurol. 72, 648-72 (2012).
4. Lajoie, J. M. & Shusta, E. V. Targeting receptor-mediated transport for delivery of biologics across the blood-brain barrier. Annu. Rev. Pharmacol. Toxicol. 55, 613-31 (2015).
5. Jones, A. R. & Shusta, E. V. Blood-brain barrier transport of therapeutics via receptor-mediation. Pharm. Res. 24, 1759-1771 (2007).
6. Ueno, M. et al. Transporters in the brain endothelial barrier. Curr. Med. Chem. 17, 1125-38 (2010).
7. Moos, T. & Morgan, E. H. Restricted transport of anti-transferrin receptor antibody (OX26) through the blood-brain barrier in the rat. J. Neurochem. 79, 119-29 (2001).
8. Bien-Ly, N. et al. Transferrin receptor (TfR) trafficking determines brain uptake of TfR antibody affinity variants. J. Exp. Med. (2014). doi:10.1084/jem.20131660
9. Yu, Y. J. et al. Boosting brain uptake of a therapeutic antibody by reducing its affinity for a transcytosis target. Sci. Transl. Med. 3 (2011).
10. Niewoehner, J. et al. Increased Brain Penetration and Potency of a Therapeutic Antibody Using a Monovalent Molecular Shuttle. Neuron 81, 49-60 (2014).
11. Yu, Y. J. et al. Therapeutic bispecific antibodies cross the blood-brain barrier in nonhuman primates. Sci. Transl. Med. 6 (2014).
12. Goulatis, L. I. & Shusta, E. V. Protein engineering approaches for regulating blood-brain barrier transcytosis. Curr. Opin. Struct. Biol. 45, 109-115 (2017).

13. Zuchero, Y. J. Y. et al. Discovery of Novel Blood-Brain Barrier Targets to Enhance Brain Uptake of Therapeutic Antibodies. Neuron 89, 70-82 (2015).
14. Muruganandam, A., Tanha, J., Narang, S. & Stanimirovic, D. Selection of phage-displayed llama single-domain antibodies that transmigrate across human blood-brain barrier endothelium. FASEB J. 16 (2002).
15. Abulrob, A., Sprong, H., Van Bergen en Henegouwen, P. & Stanimirovic, D. The blood-brain barrier transmigrating single domain antibody: mechanisms of transport and antigenic epitopes in human brain endothelial cells. J. Neurochem. 95, 1201-14 (2005).
16. Stutz, C. C., Zhang, X. & Shusta, E. V. Combinatorial approaches for the identification of brain drug delivery targets. Curr. Pharm. Des. 20, 1564-76 (2014).
17. Pasqualini, R. & Ruoslahti, E. Organ targeting in vivo using phage display peptide libraries. Nature 380, 364-6 (1996).
18. Wang, X. X., Cho, Y. K. & Shusta, E. V. Mining a yeast library for brain endothelial cell-binding antibodies. Nat. Methods 4, 143-145 (2007).
19. Calabria, A. R. & Shusta, E. V. A genomic comparison of in vivo and in vitro brain microvascular endothelial cells. J. Cereb. Blood Flow Metab. 28, 135-48 (2008).
20. Lyck, R. et al. Culture-induced changes in blood-brain barrier transcriptome: implications for amino-acid transporters in vivo. J. Cereb. Blood Flow Metab. 29, 1491-502 (2009).
21. Zhou, H., Zhang, Y.-L., Lu, G., Ji, H. & Rodi, C. P. Recombinant antibody libraries and selection technologies. N. Biotechnol. 28, 448-52 (2011).
22. Ponsel, D., Neugebauer, J., Ladetzki-Baehs, K. & Tissot, K. High affinity, developability and functional size: the holy grail of combinatorial antibody library generation. Molecules 16, 3675-700 (2011).
23. Agarwal, N. & Shusta, E. V. Multiplex expression cloning of blood-brain barrier membrane proteins. Proteomics 9, 1099-108 (2009).
24. Agarwal, N., Lippmann, E. S. & Shusta, E. V. Identification and expression profiling of blood-brain barrier membrane proteins. J. Neurochem. 112, 625-35 (2010).
25. Kasahara, M. & Sutoh, Y. Two forms of adaptive immunity in vertebrates: similarities and differences. Adv. Immunol. 122, 59-90 (2014).
26. Herrin, B. R. et al. Structure and specificity of lamprey monoclonal antibodies. Proc. Natl. Acad. Sci. U.S.A. 105, 2040-5 (2008).
27. Herrin, B. R. & Cooper, M. D. Alternative adaptive immunity in jawless vertebrates. J. Immunol. 185, 1367-74 (2010).
28. Han, B. W., Herrin, B. R., Cooper, M. D. & Wilson, I. A. Antigen recognition by variable lymphocyte receptors. Science 321, 1834-7 (2008).
29. Hong, X. et al. Sugar-binding proteins from fish: selection of high affinity lambodies' that recognize biomedically relevant glycans. ACS Chem. Biol. 8, 152-60 (2013).
30. Yu, C. et al. Identification of human plasma cells with a lamprey monoclonal antibody. JCI Insight 1 (2016).
31. Collins, B. C. et al. Structural Insights into VLR Fine Specificity for Blood Group Carbohydrates. Structure 25, 1-12 (2017).
32. Chia, P. Z. C., Gunn, P. & Gleeson, P. A. Cargo trafficking between endosomes and the trans-Golgi network. Histochem. Cell Biol. 140, 307-15 (2013).
33. Gunn, R. J., Herrin, B. R., Acharya, S., Cooper, M. D. & Wilson, I. A. VLR Recognition of TLR5 Expands the Molecular Characterization of Protein Antigen Binding by Non-Ig-based Antibodies. J. Mol. Biol. 430, 1350-1367 (2018).
34. Kumagai, A. K., Dwyer, K. J. & Pardridge, W. M. Differential glycosylation of the GLUT1 glucose transporter in brain capillaries and choroid plexus. Biochim. Biophys. Acta 1193, 24-30 (1994).
35. Michel, C. C. Transport of macromolecules through microvascular walls. Cardiovasc. Res. 32, 644-53 (1996).
36. Weinbaum, S., Tarbell, J. M. & Damiano, E. R. The structure and function of the endothelial glycocalyx layer. Annu. Rev. Biomed. Eng. 9, 121-67 (2007).
37. Vogel, J. et al. Influence of the endothelial glycocalyx on cerebral blood flow in mice. J. Cereb. Blood Flow Metab. 20, 1571-8 (2000).
38. Lidinsky, W. A. & Drewes, L. R. Characterization of the Blood-Brain Barrier: Protein Composition of the Capillary Endothelial Cell Membrane. J. Neurochem. 41, 1341-1348 (1983).
39. Cho, Y. K. & Shusta, E. V. Antibody library screens using detergent-solubilized mammalian cell lysates as antigen sources. Protein Eng. Des. Sel. 23, 567-577 (2010).
40. Tillotson, B. J., Cho, Y. K. & Shusta, E. V. Cells and cell lysates: A direct approach for engineering antibodies against membrane proteins using yeast surface display. Methods 60, 27-37 (2013).
41. Williams, R. L. et al. Endothelioma cells expressing the polyoma middle T oncogene induce hemangiomas by host cell recruitment. Cell 57, 1053-63 (1989).
42. Iacopetta, B. J. & Morgan, E. H. The kinetics of transferrin endocytosis and iron uptake from transferrin in rabbit reticulocytes. J. Biol. Chem. 258, 9108-15 (1983).
43. Luo, M. et al. Recognition of the Thomsen-Friedenreich pancarcinoma carbohydrate antigen by a lamprey variable lymphocyte receptor. J. Biol. Chem. 288, 23597-606 (2013).
44. Venkataraman, M., Sasisekharan, R. & Raman, R. Glycan Array Data Management at Consortium for Functional Glycomics. in Methods in molecular biology (Clifton, N.J.) 1273, 181-190 (2015).
45. Wang, X. X. & Shusta, E. V. The use of scFv-displaying yeast in mammalian cell surface selections. J. Immunol. Methods 304, 30-42 (2005).
46. Stern, L. A. et al. Geometry and expression enhance enrichment of functional yeast-displayed ligands via cell panning. Biotechnol. Bioeng. (2016). doi:10.1002/bit.26001
47. Tillotson, B. J., de Larrinoa, I. F., Skinner, C. A., Klavas, D. M. & Shusta, E. V. Antibody affinity maturation using yeast display with detergent-solubilized membrane proteins as antigen sources. Protein Eng. Des. Sel. 26, 101-112 (2013).
48. Tillotson, B. J., Goulatis, L. I., Parenti, I., Duxbury, E. & Shusta, E. V. Engineering an Anti-Transferrin Receptor ScFv for pH-Sensitive Binding Leads to Increased Intracellular Accumulation. PLoS One 10, e0145820 (2015).
49. Jones, A. R., Stutz, C. C., Zhou, Y., Marks, J. D. & Shusta, E. V. Identifying blood-brain-barrier selective single-chain antibody fragments. Biotechnol. J. 9, 664-74 (2014).
50. Tasumi, S. et al. High-affinity lamprey VLRA and VLRB monoclonal antibodies. Proc. Natl. Acad. Sci. U.S.A. 106, 12891-6 (2009).
51. van den Berg, B. M., Vink, H. & Spaan, J. A. E. The endothelial glycocalyx protects against myocardial edema. Circ. Res. 92, 592-4 (2003).

52. Weinbaum, S., Zhang, X., Han, Y., Vink, H. & Cowin, S. C. Mechanotransduction and flow across the endothelial glycocalyx. Proc. Natl. Acad. Sci. U.S.A. 100, 7988-95 (2003).
53. Scott, D. W. & Patel, R. P. Endothelial heterogeneity and adhesion molecules N-glycosylation: implications in leukocyte trafficking in inflammation. Glycobiology 23, 622-33 (2013).
54. Stutz, C. C., et al. Identifying blood-brain-barrier selective single-chain antibody fragments. Biotechnol J. 9, 664-74 (2015).
55. Farrington, G. K. et al. A novel platform for engineering blood-brain barrier-crossing bispecific biologics. FASEB J. (2014). doi:10.1096/fj.14-253369
56. Gadkar, K. et al. Mathematical PKPD and safety model of bispecific TfR/BACE1 antibodies for the optimization of antibody uptake in brain. Eur. J. Pharm. Biopharm. 101, 53-61 (2016).
57. Calderon, A. J. et al. Optimizing endothelial targeting by modulating the antibody density and particle concentration of anti-ICAM coated carriers. J. Control. Release 150, 37-44 (2011).
58. Lee, J.-J. et al. A high-affinity protein binder that blocks the IL-6/STAT3 signaling pathway effectively suppresses non-small cell lung cancer. Mol. Ther. 22, 1254-65 (2014).
59. Lee, S.-C. et al. Design of a binding scaffold based on variable lymphocyte receptors of jawless vertebrates by module engineering. Proc. Natl. Acad. Sci. U.S.A. 109, 3299-304 (2012).
60. Hwang, D.-E. et al. Anti-Human VEGF Repebody Effectively Suppresses Choroidal Neovascularization and Vascular Leakage. PLoS One 11, e0152522 (2016).
61. Piatesi, A. et al. Directed evolution for improved secretion of cancer-testis antigen NY-ESO-1 from yeast. Protein Expr. Purif. 48, 232-242 (2006).
62. Silber, P. M., Gandolfi, A. J. & Brendel, K. Adaptation of a gamma-glutamyl-transferase transpeptidase assay to microtiter plates. Anal. Biochem. 158, 68-71 (1986).
63. Alder, M. N. et al. Antibody responses of variable lymphocyte receptors in the lamprey. Nat. Immunol. 9, 319-27 (2008).
64. Chao, G. et al. Isolating and engineering human antibodies using yeast surface display. Nat. Protoc. 1, 755-768 (2006).
65. Kumar, P. et al. Macromolecularly crowded in vitro microenvironments accelerate the production of extracellular matrix-rich supramolecular assemblies. Sci. Rep. 5, 8729 (2015).
66. Castaldo, C. et al. Cardiac fibroblast-derived extracellular matrix (biomatrix) as a model for the studies of cardiac primitive cell biological properties in normal and pathological adult human heart. Biomed Res. Int. (2013).
67. Harvey, A., Yen, T.-Y., Aizman, I., Tate, C. & Case, C. Proteomic analysis of the extracellular matrix produced by mesenchymal stromal cells: implications for cell therapy mechanism. PLoS One 8, e79283 (2013).

Each publication, patent, and patent publication cited in this disclosure is incorporated in reference herein in its entirety. The present invention is not intended to be limited to the foregoing examples, but encompasses all such modifications and variations as come within the scope of the appended claims.

The invention claimed is:

1. An isolated polypeptide antigen-binding fragment thereof comprising a variable lymphocyte receptor (VLR) amino acid sequence comprising the following regions:
   (i) EVRCESRSLASVPA (SEQ ID NO:5) and RRLHLHR (SEQ ID NO:6), or TVDCSGKSLASVPT (SEQ ID NO: 13) and QILRLYRNQI (SEQ ID NO:14), or TVDCSGKSLASVPT (SEQ ID NO:16) and RWLHLHR (SEQ ID NO:17),
   (ii) YLNLGG (SEQ ID NO:7),
   (iii) ELKLYS (SEQ ID NO:8),
   (iv) HLDLSK (SEQ ID NO:9),
   (v) HAYLFG (SEQ ID NO: 10), and
   (vi) SIVMRWDGKAVNDPDSAK (SEQ ID NO:11).

2. The isolated polypeptide or antigen-binding fragment thereof of claim 1, wherein the isolated polypeptide or antigen-binding fragment thereof is able to specifically bind to and cross the blood brain barrier in vivo, and wherein the VLR amino acid sequence comprises the regions:
   (a) EVRCESRSLASVPA (SEQ ID NO:5), RRLHLHR (SEQ ID NO:6), YLNLGG (SEQ ID NO:7), ELKLYS (SEQ ID NO:8), HLDLSK (SEQ ID NO:9), HAYLFG (SEQ ID NO:10), and SIVMRWDGKAVNDPDSAK (SEQ ID NO: 11), or
   (b) TVDCSGKSLASVPT (SEQ ID NO: 16); RWLHLHR (SEQ ID NO: 17), YLNLGG (SEQ ID NO:7), ELKLYS (SEQ ID NO:8), HLDLSK (SEQ ID NO:9), HAYLFG (SEQ ID NO:10), and SIVMRWDGKAVNDPDSAK (SEQ ID NO: 11).

3. The isolated polypeptide or antigen-binding fragment thereof of claim 1, wherein the isolated polypeptide or antigen-binding fragment thereof is able to specifically bind to brain microvascular endothelial cells (BMECs) surface, and wherein the VLR amino acid sequence comprises the regions:
   (i) TVDCSGKSLASVPT (SEQ ID NO: 13),
   (ii) QILRLYRNQI (SEQ ID NO: 14), (iii) YLNLGG (SEQ ID NO:7),
(iv) ELKLYS (SEQ ID NO:8),
(v) HLDLSK (SEQ ID NO:9),
(vi) HAYLFG (SEQ ID NO: 10), and
(vii) SIVMRWDGKAVNDPDSAK (SEQ ID NO:11).

4. The isolated polypeptide or antigen-binding fragment thereof of claim 1, wherein the VLR amino acid sequence is selected from the group consisting of VLR 11 (SEQ ID NO:1), VLR30 (SEQ ID NO:2), VLR46 (SEQ ID NO:3), and an amino acid sequence with at least 95% sequence identity to SEQ ID NO:1, SEQ ID NO:2 or SEQ ID NO:3.

5. The isolated polypeptide or antigen-binding fragment thereof of claim 1, wherein the VLR amino acid sequence is directly or indirectly linked to an agent.

6. The isolated polypeptide or antigen-binding fragment thereof of claim 5, wherein the agent is selected from the group consisting of a therapeutic agent, a pharmaceutical agent, a diagnostic agent, an imaging agent, a detection agent, an immunological therapeutic construct, and a combination thereof.

7. The isolated polypeptide or antigen-binding fragment thereof of claim 5, wherein the agent is a polypeptide directly or indirectly fused to the isolated polypeptide as a fusion protein.

8. The isolated polypeptide or antigen-binding fragment thereof of claim 5, wherein the agent is a portion of a fragment crystallizable region (Fc) of an antibody.

9. The isolated peptide or antigen-binding fragment thereof of claim 8, wherein the Fc is from human IgG.

10. A composition comprising the isolated peptide or antigen-binding fragment thereof of claim 1 and a pharmaceutically acceptable carrier.

11. An isolated nucleic acid sequence encoding the isolated polypeptide or antigen-binding fragment thereof of claim 1.

12. A vector comprising the isolated nucleic acid sequence of claim 11.

13. A cell able to express the isolated polypeptide or antigen-binding fragment thereof of claim 1.

14. A method of targeting an agent to the blood brain barrier (BBB) of a subject, the method comprising:
(a) administering to the subject the isolated polypeptide or antigen-binding fragment thereof of claim 5, wherein the VLR amino acid sequence is directly or indirectly linked to the agent.

15. The method of claim 14, wherein the agent is:
(a) delivered to the surface of the BBB after targeting; and/or
(b) able to cross the BBB after targeting.

16. The method of claim 14, wherein the agent is selected from the group consisting of a therapeutic agent, a pharmaceutical agent, a diagnostic agent, an imaging agent, a detection agent, an immunological therapeutic construct, and a combination thereof.

17. A method of detecting or imaging blood brain barrier endothelial cells (BMECs), the method comprising:
(a) contacting the BMECs with the isolated polypeptide or antigen-binding fragment thereof of claim 5, and
(b) detecting or imaging the BMECs.

18. The method of claim 17, wherein the contacting step comprises administering the isolated polypeptide to a subject and wherein the detecting or imaging step is performed in vivo in a subject.

19. The method of claim 18, wherein the isolated polypeptide or antigen-binding fragment thereof is administered to the subject systemically.

20. The method of claim 17, wherein the detecting or imaging step comprises PET or MRI imaging.

21. The isolated polypeptide or antigen-binding fragment thereof of claim 1, wherein the VLR amino acid sequence is capable of binding a Neu5Acα2-6Galβ1-4GlcNAcβ1-3Gal motif or a Neu5Acα2-6Galβ1-4GlcNAcβ1-3GalNAc motif on the BBB.

22. The isolated polypeptide or antigen-binding fragment thereof of claim 21, wherein the isolated polypeptide or antigen-binding fragment thereof is capable of engaging and trafficking within the BBB endothelium.

* * * * *

UNITED STATES PATENT AND TRADEMARK OFFICE
CERTIFICATE OF CORRECTION

PATENT NO. : 12,371,468 B2
APPLICATION NO. : 17/429602
DATED : July 29, 2025
INVENTOR(S) : Eric V. Shusta et al.

Page 1 of 1

It is certified that error appears in the above-identified patent and that said Letters Patent is hereby corrected as shown below:

In the Specification

Column 2, Line 32, "antigens" should be --antigens$^{18}$--.

Column 19, Line 66, "MM scan," should be --MRI scan,--.

Column 24, Line 40, "204" should be --2µM--.

Column 30, Line 28, "255±35m" should be --255±35µg--.

Column 33, Line 28, "(Thermo Fisher, 121411)" should be --(Thermo Fisher I21411)--.

Signed and Sealed this
Ninth Day of September, 2025

Coke Morgan Stewart
*Acting Director of the United States Patent and Trademark Office*

SEQUENCE LISTING

<160> NUMBER OF SEQ ID NOS: 31

<210> SEQ ID NO 1
<211> LENGTH: 200
<212> TYPE: PRT
<213> ORGANISM: Artificial Sequence
<220> FEATURE:
<223> OTHER INFORMATION: Synthetic- VLR11

<400> SEQUENCE: 1

```
Ala Cys Pro Ser Gln Cys Ser Cys Ser Gly Thr Glu Val Arg Cys Glu
1               5                  10                  15

Ser Arg Ser Leu Ala Ser Val Pro Ala Gly Ile Pro Thr Thr Thr Arg
            20                  25                  30

Arg Leu His Leu His Arg Asn Gln Leu Thr Lys Leu Glu Pro Gly Val
        35                  40                  45

Phe Asp Ser Leu Thr Gln Leu Thr Tyr Leu Asn Leu Gly Gly Asn Gln
    50                  55                  60

Leu Thr Ala Leu Pro Val Gly Val Phe Asp Lys Leu Thr Asn Leu Lys
65                  70                  75                  80

Glu Leu Lys Leu Tyr Ser Asn Gln Leu Gln Ala Leu Ser Glu Gly Leu
                85                  90                  95

Phe Asp Arg Leu Gly Lys Leu Gln His Leu Asp Leu Ser Lys Asn Gln
            100                 105                 110

Leu Lys Ser Ile Pro His Gly Ala Phe Asp Arg Leu Ser Ser Leu Thr
        115                 120                 125

His Ala Tyr Leu Phe Gly Asn Pro Trp Asp Cys Glu Cys Arg Asp Ile
    130                 135                 140
```

```
Met Tyr Leu Arg Asn Trp Val Ala Asp His Thr Ser Ile Val Met Arg
145                 150                 155                 160

Trp Asp Gly Lys Ala Val Asn Asp Pro Asp Ser Ala Lys Cys Ala Gly
            165                 170                 175

Thr Asn Thr Pro Val Arg Ala Val Thr Glu Ala Ser Thr Ser Pro Ser
        180                 185                 190

Lys Cys Pro Gly Tyr Val Ala Thr
        195                 200

<210> SEQ ID NO 2
<211> LENGTH: 200
<212> TYPE: PRT
<213> ORGANISM: Artificial Sequence
<220> FEATURE:
<223> OTHER INFORMATION: Synthetic- VLR30

<400> SEQUENCE: 2

Ala Cys Pro Ser Gln Cys Ser Cys Ser Gly Thr Thr Val Asp Cys Ser
1               5                   10                  15

Gly Lys Ser Leu Ala Ser Val Pro Thr Gly Ile Pro Thr Thr Thr Gln
            20                  25                  30

Ile Leu Arg Leu Tyr Arg Asn Gln Ile Thr Lys Leu Glu Pro Gly Val
        35                  40                  45

Phe Asp Ser Leu Thr Gln Leu Thr Tyr Leu Asn Leu Gly Gly Asn Gln
50                  55                  60

Leu Thr Ala Leu Pro Val Gly Val Phe Asp Lys Leu Thr Asn Leu Lys
65                  70                  75                  80

Glu Leu Lys Leu Tyr Ser Asn Gln Leu Gln Ala Leu Ser Glu Gly Leu
                85                  90                  95

Phe Asp Arg Leu Gly Lys Leu Gln His Leu Asp Leu Ser Lys Asn Gln
            100                 105                 110

Leu Lys Ser Ile Pro His Gly Ala Phe Asp Arg Leu Ser Ser Leu Thr
        115                 120                 125

His Ala Tyr Leu Phe Gly Asn Pro Trp Asp Cys Glu Cys Arg Asp Ile
130                 135                 140

Met Tyr Leu Arg Asn Trp Val Ala Asp His Thr Ser Ile Val Met Arg
145                 150                 155                 160

Trp Asp Gly Lys Ala Val Asn Asp Pro Asp Ser Ala Lys Cys Ala Gly
            165                 170                 175

Thr Asn Thr Pro Val Arg Ala Val Thr Glu Ala Ser Thr Ser Pro Ser
        180                 185                 190

Lys Cys Pro Gly Tyr Val Ala Thr
        195                 200

<210> SEQ ID NO 3
<211> LENGTH: 200
<212> TYPE: PRT
<213> ORGANISM: Artificial Sequence
<220> FEATURE:
<223> OTHER INFORMATION: Synthetic- VLR46

<400> SEQUENCE: 3

Ala Cys Pro Ser Gln Cys Ser Cys Ser Gly Thr Thr Val Asp Cys Ser
1               5                   10                  15

Gly Lys Ser Leu Ala Ser Val Pro Thr Gly Ile Pro Thr Thr Thr Arg
            20                  25                  30

Trp Leu His Leu His Arg Asn Gln Leu Thr Lys Leu Glu Pro Gly Val
```

```
                35                  40                  45
Phe Asp Ser Leu Thr Gln Leu Thr Tyr Leu Asn Leu Gly Gly Asn Gln
 50                  55                  60

Leu Thr Ala Leu Pro Val Gly Val Phe Asp Lys Leu Thr Asn Leu Lys
 65                  70                  75                  80

Glu Leu Lys Leu Tyr Ser Asn Gln Leu Gln Ala Leu Ser Glu Gly Leu
                 85                  90                  95

Phe Asp Arg Leu Gly Lys Leu Gln His Leu Asp Leu Ser Lys Asn Gln
                100                 105                 110

Leu Lys Ser Ile Pro His Gly Ala Phe Asp Arg Leu Ser Ser Leu Thr
                115                 120                 125

His Ala Tyr Leu Phe Gly Asn Pro Trp Asp Cys Glu Cys Arg Asp Ile
            130                 135                 140

Met Tyr Leu Arg Asn Trp Val Ala Asp His Thr Ser Ile Val Met Arg
145                 150                 155                 160

Trp Asp Gly Lys Ala Val Asn Asp Pro Asp Ser Ala Lys Cys Ala Gly
                165                 170                 175

Thr Asn Thr Pro Val Arg Ala Val Thr Glu Ala Ser Thr Ser Pro Ser
                180                 185                 190

Lys Cys Pro Gly Tyr Val Ala Thr
                195                 200

<210> SEQ ID NO 4
<211> LENGTH: 200
<212> TYPE: PRT
<213> ORGANISM: Artificial Sequence
<220> FEATURE:
<223> OTHER INFORMATION: Synthetic- generic VLR11
<220> FEATURE:
<221> NAME/KEY: misc_feature
<222> LOCATION: (1)..(11)
<223> OTHER INFORMATION: Xaa can be any naturally occurring amino acid
<220> FEATURE:
<221> NAME/KEY: misc_feature
<222> LOCATION: (26)..(31)
<223> OTHER INFORMATION: Xaa can be any naturally occurring amino acid
<220> FEATURE:
<221> NAME/KEY: misc_feature
<222> LOCATION: (39)..(56)
<223> OTHER INFORMATION: Xaa can be any naturally occurring amino acid
<220> FEATURE:
<221> NAME/KEY: misc_feature
<222> LOCATION: (63)..(80)
<223> OTHER INFORMATION: Xaa can be any naturally occurring amino acid
<220> FEATURE:
<221> NAME/KEY: misc_feature
<222> LOCATION: (87)..(104)
<223> OTHER INFORMATION: Xaa can be any naturally occurring amino acid
<220> FEATURE:
<221> NAME/KEY: misc_feature
<222> LOCATION: (111)..(128)
<223> OTHER INFORMATION: Xaa can be any naturally occurring amino acid
<220> FEATURE:
<221> NAME/KEY: misc_feature
<222> LOCATION: (135)..(155)
<223> OTHER INFORMATION: Xaa can be any naturally occurring amino acid
<220> FEATURE:
<221> NAME/KEY: misc_feature
<222> LOCATION: (174)..(200)
<223> OTHER INFORMATION: Xaa can be any naturally occurring amino acid

<400> SEQUENCE: 4

Xaa Xaa Xaa Xaa Xaa Xaa Xaa Xaa Xaa Xaa Glu Val Arg Cys Glu
 1               5                  10                  15

Ser Arg Ser Leu Ala Ser Val Pro Ala Xaa Xaa Xaa Xaa Xaa Xaa Arg
                 20                  25                  30
```

-continued

```
Arg Leu His Leu His Arg Xaa Xaa Xaa Xaa Xaa Xaa Xaa Xaa Xaa
        35                  40                  45

Xaa Xaa Xaa Xaa Xaa Xaa Xaa Tyr Leu Asn Leu Gly Gly Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Glu Leu Lys Leu Tyr Ser Xaa Xaa Xaa Xaa Xaa Xaa Xaa Xaa Xaa
                85                  90                  95

Xaa Xaa Xaa Xaa Xaa Xaa Xaa His Leu Asp Leu Ser Lys Xaa Xaa
            100                 105                 110

Xaa Xaa Xaa Xaa Xaa Xaa Xaa Xaa Xaa Xaa Xaa Xaa Xaa Xaa Xaa
        115                 120                 125

His Ala Tyr Leu Phe Gly Xaa Xaa Xaa Xaa Xaa Xaa Xaa Xaa Xaa
    130                 135                 140

Xaa Xaa Xaa Xaa Xaa Xaa Xaa Xaa Xaa Xaa Ser Ile Val Met Arg
145                 150                 155                 160

Trp Asp Gly Lys Ala Val Asn Asp Pro Asp Ser Ala Lys Xaa Xaa Xaa
                165                 170                 175

Xaa Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa
        195                 200
```

<210> SEQ ID NO 5
<211> LENGTH: 14
<212> TYPE: PRT
<213> ORGANISM: Artificial Sequence
<220> FEATURE:
<223> OTHER INFORMATION: Synthetic- Antigen-binding fragment of VLR11

<400> SEQUENCE: 5

```
Glu Val Arg Cys Glu Ser Arg Ser Leu Ala Ser Val Pro Ala
1               5                   10
```

<210> SEQ ID NO 6
<211> LENGTH: 7
<212> TYPE: PRT
<213> ORGANISM: Artificial Sequence
<220> FEATURE:
<223> OTHER INFORMATION: Synthetic- Antigen-binding fragment of VLR11

<400> SEQUENCE: 6

```
Arg Arg Leu His Leu His Arg
1               5
```

<210> SEQ ID NO 7
<211> LENGTH: 6
<212> TYPE: PRT
<213> ORGANISM: Artificial Sequence
<220> FEATURE:
<223> OTHER INFORMATION: Synthetic- Antigen-binding fragment of VLR11,
      VLR30, and VLR46

<400> SEQUENCE: 7

```
Tyr Leu Asn Leu Gly Gly
1               5
```

<210> SEQ ID NO 8
<211> LENGTH: 6
<212> TYPE: PRT
<213> ORGANISM: Artificial Sequence

```
<220> FEATURE:
<223> OTHER INFORMATION: Synthetic- Antigen-binding fragment of VLR11,
      VLR30, and VLR46

<400> SEQUENCE: 8

Glu Leu Lys Leu Tyr Ser
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic- Antigen-binding fragment of VLR11,
      VLR30, and VLR46

<400> SEQUENCE: 9

His Leu Asp Leu Ser Lys
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic- Antigen-binding fragment of VLR11,
      VLR30, and VLR46

<400> SEQUENCE: 10

His Ala Tyr Leu Phe Gly
1               5

<210> SEQ ID NO 11
<211> LENGTH: 18
<212> TYPE: PRT
<213> ORGANISM: Artificial Sequence
<220> FEATURE:
<223> OTHER INFORMATION: Synthetic- Antigen-binding fragment of VLR11,
      VLR30, and VLR46

<400> SEQUENCE: 11

Ser Ile Val Met Arg Trp Asp Gly Lys Ala Val Asn Asp Pro Asp Ser
1               5                   10                  15

Ala Lys

<210> SEQ ID NO 12
<211> LENGTH: 200
<212> TYPE: PRT
<213> ORGANISM: Artificial Sequence
<220> FEATURE:
<223> OTHER INFORMATION: Synthetic- generic VLR30
<220> FEATURE:
<221> NAME/KEY: misc_feature
<222> LOCATION: (1)..(11)
<223> OTHER INFORMATION: Xaa can be any naturally occurring amino acid
<220> FEATURE:
<221> NAME/KEY: misc_feature
<222> LOCATION: (26)..(31)
<223> OTHER INFORMATION: Xaa can be any naturally occurring amino acid
<220> FEATURE:
<221> NAME/KEY: misc_feature
<222> LOCATION: (42)..(56)
<223> OTHER INFORMATION: Xaa can be any naturally occurring amino acid
<220> FEATURE:
<221> NAME/KEY: misc_feature
<222> LOCATION: (63)..(80)
<223> OTHER INFORMATION: Xaa can be any naturally occurring amino acid
<220> FEATURE:
<221> NAME/KEY: misc_feature
<222> LOCATION: (87)..(104)
```

```
<223> OTHER INFORMATION: Xaa can be any naturally occurring amino acid
<220> FEATURE:
<221> NAME/KEY: misc_feature
<222> LOCATION: (111)..(128)
<223> OTHER INFORMATION: Xaa can be any naturally occurring amino acid
<220> FEATURE:
<221> NAME/KEY: misc_feature
<222> LOCATION: (135)..(155)
<223> OTHER INFORMATION: Xaa can be any naturally occurring amino acid
<220> FEATURE:
<221> NAME/KEY: misc_feature
<222> LOCATION: (174)..(200)
<223> OTHER INFORMATION: Xaa can be any naturally occurring amino acid

<400> SEQUENCE: 12

Xaa Xaa Xaa Xaa Xaa Xaa Xaa Xaa Xaa Xaa Xaa Thr Val Asp Cys Ser
 1               5                  10                  15

Gly Lys Ser Leu Ala Ser Val Pro Thr Xaa Xaa Xaa Xaa Xaa Xaa Gln
            20                  25                  30

Ile Leu Arg Leu Tyr Arg Asn Gln Ile Xaa Xaa Xaa Xaa Xaa Xaa Xaa
        35                  40                  45

Xaa Xaa Xaa Xaa Xaa Xaa Xaa Xaa Tyr Leu Asn Leu Gly Gly Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Glu Leu Lys Leu Tyr Ser Xaa Xaa Xaa Xaa Xaa Xaa Xaa Xaa Xaa Xaa
                85                  90                  95

Xaa Xaa Xaa Xaa Xaa Xaa Xaa His Leu Asp Leu Ser Lys Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

His Ala Tyr Leu Phe Gly Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Ser Ile Val Met Arg
145                 150                 155                 160

Trp Asp Gly Lys Ala Val Asn Asp Pro Asp Ser Ala Lys Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa
        195                 200

<210> SEQ ID NO 13
<211> LENGTH: 14
<212> TYPE: PRT
<213> ORGANISM: Artificial Sequence
<220> FEATURE:
<223> OTHER INFORMATION: Synthetic- Antigen-binding fragment of VLR30

<400> SEQUENCE: 13

Thr Val Asp Cys Ser Gly Lys Ser Leu Ala Ser Val Pro Thr
 1               5                  10

<210> SEQ ID NO 14
<211> LENGTH: 10
<212> TYPE: PRT
<213> ORGANISM: Artificial Sequence
<220> FEATURE:
<223> OTHER INFORMATION: Synthetic- Antigen-binding fragment of VLR30

<400> SEQUENCE: 14

Gln Ile Leu Arg Leu Tyr Arg Asn Gln Ile
```

<210> SEQ ID NO 15
<211> LENGTH: 200
<212> TYPE: PRT
<213> ORGANISM: Artificial Sequence
<220> FEATURE:
<223> OTHER INFORMATION: Synthetic- generic VLR46
<220> FEATURE:
<221> NAME/KEY: misc_feature
<222> LOCATION: (1)..(11)
<223> OTHER INFORMATION: Xaa can be any naturally occurring amino acid
<220> FEATURE:
<221> NAME/KEY: misc_feature
<222> LOCATION: (26)..(31)
<223> OTHER INFORMATION: Xaa can be any naturally occurring amino acid
<220> FEATURE:
<221> NAME/KEY: misc_feature
<222> LOCATION: (39)..(56)
<223> OTHER INFORMATION: Xaa can be any naturally occurring amino acid
<220> FEATURE:
<221> NAME/KEY: misc_feature
<222> LOCATION: (63)..(80)
<223> OTHER INFORMATION: Xaa can be any naturally occurring amino acid
<220> FEATURE:
<221> NAME/KEY: misc_feature
<222> LOCATION: (87)..(104)
<223> OTHER INFORMATION: Xaa can be any naturally occurring amino acid
<220> FEATURE:
<221> NAME/KEY: misc_feature
<222> LOCATION: (111)..(128)
<223> OTHER INFORMATION: Xaa can be any naturally occurring amino acid
<220> FEATURE:
<221> NAME/KEY: misc_feature
<222> LOCATION: (135)..(155)
<223> OTHER INFORMATION: Xaa can be any naturally occurring amino acid
<220> FEATURE:
<221> NAME/KEY: misc_feature
<222> LOCATION: (174)..(200)
<223> OTHER INFORMATION: Xaa can be any naturally occurring amino acid

<400> SEQUENCE: 15

Xaa Xaa Xaa Xaa Xaa Xaa Xaa Xaa Xaa Xaa Xaa Thr Val Asp Cys Ser
1               5                   10                  15

Gly Lys Ser Leu Ala Ser Val Pro Thr Xaa Xaa Xaa Xaa Xaa Xaa Arg
            20                  25                  30

Trp Leu His Leu His Arg Xaa Xaa Xaa Xaa Xaa Xaa Xaa Xaa Xaa Xaa
        35                  40                  45

Xaa Xaa Xaa Xaa Xaa Xaa Xaa Xaa Tyr Leu Asn Leu Gly Gly Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Glu Leu Lys Leu Tyr Ser Xaa Xaa Xaa Xaa Xaa Xaa Xaa Xaa Xaa Xaa
            85                  90                  95

Xaa Xaa Xaa Xaa Xaa Xaa Xaa His Leu Asp Leu Ser Lys Xaa Xaa Xaa
        100                 105                 110

Xaa Xaa Xaa Xaa Xaa Xaa Xaa Xaa Xaa Xaa Xaa Xaa Xaa Xaa Xaa Xaa
    115                 120                 125

His Ala Tyr Leu Phe Gly Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Ser Ile Val Met Arg
            145                 150                 155                 160

Trp Asp Gly Lys Ala Val Asn Asp Pro Asp Ser Ala Lys Xaa Xaa Xaa
        165                 170                 175

Xaa Xaa Xaa Xaa Xaa Xaa Xaa Xaa Xaa Xaa Xaa Xaa Xaa Xaa Xaa
    180                 185                 190

Xaa Xaa Xaa Xaa Xaa Xaa Xaa Xaa
        195                 200

<210> SEQ ID NO 16
<211> LENGTH: 14
<212> TYPE: PRT
<213> ORGANISM: Artificial Sequence
<220> FEATURE:
<223> OTHER INFORMATION: Synthetic- Antigen-binding fragment of VLR46

<400> SEQUENCE: 16

Thr Val Asp Cys Ser Gly Lys Ser Leu Ala Ser Val Pro Thr
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Synthetic- Antigen-binding fragment of VLR46

<400> SEQUENCE: 17

Arg Trp Leu His Leu His Arg
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic- His tag

<400> SEQUENCE: 18

His His His His His His
1               5

<210> SEQ ID NO 19
<211> LENGTH: 10
<212> TYPE: PRT
<213> ORGANISM: Artificial Sequence
<220> FEATURE:
<223> OTHER INFORMATION: Synthetic- cMyc tag

<400> SEQUENCE: 19

Glu Gln Lys Leu Ile Ser Glu Glu Asp Leu
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Synthetic- FLAG tag

<400> SEQUENCE: 20

Asp Tyr Lys Asp Asp Asp Asp Lys
1               5

<210> SEQ ID NO 21
<211> LENGTH: 14
<212> TYPE: PRT
<213> ORGANISM: Artificial Sequence
<220> FEATURE:
<223> OTHER INFORMATION: Synthetic- V5-tag

<400> SEQUENCE: 21

```
Gly Lys Pro Ile Pro Asn Pro Leu Leu Gly Leu Asp Ser Thr
1               5                   10
```

<210> SEQ ID NO 22
<211> LENGTH: 9
<212> TYPE: PRT
<213> ORGANISM: Artificial Sequence
<220> FEATURE:
<223> OTHER INFORMATION: Synthetic- HA-tag

<400> SEQUENCE: 22

```
Tyr Pro Tyr Asp Val Pro Asp Tyr Ala
1               5
```

<210> SEQ ID NO 23
<211> LENGTH: 18
<212> TYPE: PRT
<213> ORGANISM: Artificial Sequence
<220> FEATURE:
<223> OTHER INFORMATION: Synthetic- NE-tag

<400> SEQUENCE: 23

```
Thr Lys Glu Asn Pro Arg Ser Asn Gln Glu Glu Ser Tyr Asp Asp Asn
1               5                   10                  15

Glu Ser
```

<210> SEQ ID NO 24
<211> LENGTH: 15
<212> TYPE: PRT
<213> ORGANISM: Artificial Sequence
<220> FEATURE:
<223> OTHER INFORMATION: Synthetic- S-tag

<400> SEQUENCE: 24

```
Lys Glu Thr Ala Ala Ala Lys Phe Glu Arg Gln His Met Asp Ser
1               5                   10                  15
```

<210> SEQ ID NO 25
<211> LENGTH: 10
<212> TYPE: PRT
<213> ORGANISM: Artificial Sequence
<220> FEATURE:
<223> OTHER INFORMATION: Synthetic- Ty tag

<400> SEQUENCE: 25

```
Glu Val His Thr Asn Gln Asp Pro Leu Asp
1               5                   10
```

<210> SEQ ID NO 26
<211> LENGTH: 19
<212> TYPE: DNA
<213> ORGANISM: Artificial Sequence
<220> FEATURE:
<223> OTHER INFORMATION: Synthetic- Primer for the first round of
      amplification of the VLRB transcripts

<400> SEQUENCE: 26
ctccgctact cggcctgca                                                19

<210> SEQ ID NO 27
<211> LENGTH: 19
<212> TYPE: DNA
<213> ORGANISM: Artificial Sequence
<220> FEATURE:
<223> OTHER INFORMATION: Synthetic- Primer for the first round of
      amplification of the VLRB transcripts

```
<400> SEQUENCE: 27
ccgccatccc cgacctttg                                                19

<210> SEQ ID NO 28
<211> LENGTH: 17
<212> TYPE: DNA
<213> ORGANISM: Artificial Sequence
<220> FEATURE:
<223> OTHER INFORMATION: Synthetic- Primer for amplification of the VLRB
      antigen-binding domain

<400> SEQUENCE: 28
gcatgtccct cgcagtg                                                  17

<210> SEQ ID NO 29
<211> LENGTH: 19
<212> TYPE: DNA
<213> ORGANISM: Artificial Sequence
<220> FEATURE:
<223> OTHER INFORMATION: Synthetic- Primer for amplification of the VLRB
      antigen-binding domain

<400> SEQUENCE: 29
cgtggtcgta gcaacgtag                                                19

<210> SEQ ID NO 30
<211> LENGTH: 28
<212> TYPE: DNA
<213> ORGANISM: Artificial Sequence
<220> FEATURE:
<223> OTHER INFORMATION: Synthetic- Primer for amplification of VLRB-NT-
      NheI-F

<400> SEQUENCE: 30
gagagctagc tgtccctcgc agtgttcg                                      28

<210> SEQ ID NO 31
<211> LENGTH: 29
<212> TYPE: DNA
<213> ORGANISM: Artificial Sequence
<220> FEATURE:
<223> OTHER INFORMATION: Synthetic- Primer for amplification of VLRB-CT-
      AgeI-R

<400> SEQUENCE: 31
gagaaccggt cgtggtcgta gcaacgtag                                     29
```